United States Patent
Nie et al.

(10) Patent No.: US 9,345,389 B2
(45) Date of Patent: *May 24, 2016

(54) ADDITIONAL SYSTEMS AND METHODS FOR PROVIDING REAL-TIME ANATOMICAL GUIDANCE IN A DIAGNOSTIC OR THERAPEUTIC PROCEDURE

(75) Inventors: Shuming Nie, Atlanta, GA (US); Aaron M. Mohs, Winston Salem, NC (US); Michael C. Mancini, Atlanta, GA (US)

(73) Assignee: EMORY UNIVERSITY, Atlanta, GA (US)

(*) Notice: Subject to any disclaimer, the term of this patent is extended or adjusted under 35 U.S.C. 154(b) by 762 days.

This patent is subject to a terminal disclaimer.

(21) Appl. No.: 13/295,662

(22) Filed: Nov. 14, 2011

(65) Prior Publication Data

US 2012/0123205 A1 May 17, 2012

Related U.S. Application Data

(60) Provisional application No. 61/412,984, filed on Nov. 12, 2010.

(51) Int. Cl.
*A61B 1/04* (2006.01)
*A61B 1/00* (2006.01)
(Continued)

(52) U.S. Cl.
CPC ........... *A61B 1/00174* (2013.01); *A61B 5/0075* (2013.01); *A61B 5/0084* (2013.01); *A61B 5/06* (2013.01); *A61B 18/20* (2013.01);
(Continued)

(58) Field of Classification Search
None
See application file for complete search history.

(56) References Cited

U.S. PATENT DOCUMENTS 5,261,410 A   11/1993   Alfano et al.
6,826,424 B1  11/2004   Zeng et al.
(Continued)

FOREIGN PATENT DOCUMENTS

JP   H09-000497 A   1/1997
JP   11-004898      1/1999
(Continued)

OTHER PUBLICATIONS

Ott, Peter, "Hepatic Elimination of Indocyanine Green with Special Reference to Distribution Kinetics and the Influence of Plasma Protein Binding," Pharmacology & Toxicology, 1998, vol. 83, Suppl. II, pp. 5-48.

(Continued)

*Primary Examiner* — James Kish
*Assistant Examiner* — Serkan Akar
(74) *Attorney, Agent, or Firm* — Sutherland Asbill & Brennan LLP

(57) ABSTRACT

A system and method for intra-operatively providing anatomical guidance in a diagnostic or therapeutic procedure is disclosed. In embodiments, the system includes multiple light sources configured to emit different frequencies, multiple electronic imaging devices to detect various frequencies of reflected, emitted, or scattered light. The system and method incorporate an optical probe is integral to an endoscopic device or a therapeutic laser system, optically coupled to a light source; a display for displaying at least one visual representation of data; and a controller programmed to generate at least one real-time integrated visual representation of an area of interest and to display the real-time visual representation on the display for guidance during the diagnostic or therapeutic procedure.

26 Claims, 39 Drawing Sheets

(51) Int. Cl.
*A61B 5/00* (2006.01)
*A61B 5/06* (2006.01)
*G01J 3/02* (2006.01)
*G01J 3/44* (2006.01)
*A61B 18/20* (2006.01)
*A61B 19/00* (2006.01)
*A61B 17/00* (2006.01)

(52) U.S. Cl.
CPC ........... *A61B19/5225* (2013.01); *G01J 3/0272* (2013.01); *G01J 3/44* (2013.01); *A61B 1/00193* (2013.01); *A61B 5/0086* (2013.01); *A61B 19/5212* (2013.01); *A61B 2017/00061* (2013.01); *A61B 2019/5291* (2013.01)

(56) References Cited

U.S. PATENT DOCUMENTS

| | | | |
|---|---|---|---|
| 6,898,458 | B2 | 5/2005 | Zeng et al. |
| 7,115,841 | B2 | 10/2006 | Zeng et al. |
| 7,190,452 | B2 | 3/2007 | Zeng et al. |
| 7,253,894 | B2 | 8/2007 | Zeng et al. |
| 7,928,392 | B1 | 4/2011 | Heidari |
| 2002/0013531 | A1 | 1/2002 | Hayashi |
| 2002/0062061 | A1 | 5/2002 | Kaneko et al. |
| 2002/0103439 | A1 | 8/2002 | Zeng et al. |
| 2004/0006276 | A1 | 1/2004 | Demos et al. |
| 2008/0051629 | A1 | 2/2008 | Sugiyama et al. |
| 2008/0267472 | A1 | 10/2008 | Demos |
| 2009/0024018 | A1* | 1/2009 | Boyden et al. ............... 600/407 |
| 2010/0067203 | A1 | 3/2010 | Safavi-Naeini et al. |
| 2011/0068268 | A1 | 3/2011 | Heidari |
| 2011/0104071 | A1 | 5/2011 | Lee et al. |
| 2011/0152692 | A1 | 6/2011 | Nie et al. |
| 2011/0253897 | A1 | 10/2011 | Saeedkia et al. |
| 2012/0123205 | A1 | 5/2012 | Nie et al. |

FOREIGN PATENT DOCUMENTS

| | | |
|---|---|---|
| JP | 11-104059 | 4/1999 |
| JP | 2000-206047 A | 7/2000 |
| JP | 2004-089533 A | 3/2004 |
| JP | 2004-520105 A | 7/2004 |
| JP | 2004520105 A | 7/2004 |
| JP | 2004-294099 A | 10/2004 |
| JP | 2006180926 | 7/2006 |
| JP | 2009-125411 A | 6/2009 |
| JP | 2009-133876 A | 6/2009 |
| WO | 02/50518 A2 | 6/2002 |
| WO | 2008/122035 A1 | 10/2008 |
| WO | 2009/028136 A1 | 3/2009 |

OTHER PUBLICATIONS

Parungo, Cherie P., et al., "In Vivo Optical Imaging of Pleural Space Drainage to Lymph Nodes of Prognostic Significance," Annals of Surgical Oncology, vol. 11, No. 12, pp. 1085-1092.
Pleijhuis, R.G., et al., "Near-infrared fluorescence (NIRF) imaging in breast-conserving surgery: Assessing intraoperative techniques in tissue-stimulating breast phantoms," EJSO 37 (2011), pp. 32-39.
Provenzale, James M., et al., "Laser-guided area imaging and point spectroscopy for guidance during surgical resection of tumors," Presentation at the Fitzpatrick Institute for Photonics Annual Meeting, Durham, NC, Oct. 28, 2010.
Qian, X. M., et al., "Single-Molecule and single-nanoparticle SERS: from fundamental mechanisms to biomedical applications," Chem. Soc., Rev., 2008, vol. 37, pp. 912-920.
Qian, X, et al., "In vivo tumor targeting and spectroscopic detection with surface-enhanced Raman nanoparticle tags," Nature Biotechnology, Jan. 2008, vol. 26, No. 1, pp. 83-90.
Qian, Ximei, et al., "Stimuli-Responsive SERS Nanoparticles: Conformational Control of Plasmonic Coupling and Surface Raman Enhancement," J. Am. Chem. Soc., 2009, vol. 131, pp. 7540-7541.
Qian, Ximei, et al., "Surface-Enhanced Raman Nanoparticle Beacons Based on Bioconjugated Gold Nanocrystals and Long Range Plasmonic Coupling," J. Am. Chem. Soc., 2008, vol. 130, pp. 14934-14935.
Ramanujam, Nirmala, et al., "Cervical Precancer Detection Using a Multivariate Statistical Algorithm Based on Laser-Induced Fluorescence Spectra at Multiple Excitation Wavelengths," Photochemistry and Photobiology, 1996, vol. 64, No. 4, pp. 720-735.
Ramina, Ricardo, et al., "Optimizing costs of intraoperative magnetic resonance imaging. A series of 29 glioma cases," Acta Neurochir, 2010, vol. 152, pp. 27-33.
Saxena, Vishal, et al., "Enhanced photo-stability, thermal-stability and aqueous-stability of indocyanine green in polymeric nanoparticulate systems," Journal of Photochemistry and Photobiology B: Biology 74 (2004), pp. 29-38.
Saxena, Vishal, et al., "Polymeric nanoparticulate delivery system for Indocyanine green: Biodistribution in healthy mice," International Journal of Pharmaceutics, 2006, vol. 308, pp. 200-204.
Schomacker, Kevin T., et al., "Ultraviolet Laser-Induced Fluorescence of Colonic Tissue: Basic Biology and Diagnostic Potential," Lasers in Surgery and Medicine, 1992, vol. 12, pp. 63-78.
Schwarz, Richard A., "Noninvasive Evaluation of Oral Lesions Using Depth-sensitive Optical Spectroscopy," Cancer, Apr. 15, 2009, pp. 1669-1679.
Sevick-Muraca, Eva M., et al., "Imaging of Lymph Flow in Breast Cancer Patients after Microdose Administration of a Near-Infrared Fluorophore: Feasibility Study," Radiology, Mar. 2008, vol. 246, No. 3, pp. 734-741.
Sienel, Wulf, et al., "Frequency of local recurrence following segmentectomy of stage 1A non-small cell lung cancer is influenced by segment localisation and width of resection margins—implications for patient selection for segmentectomy," European Journal of Cardio-thoracic Surgery, 2007, vol. 31, pp. 522-528.
Singhal, Sunil, et al., "Nanotechnology Applications in Surgical Oncology," Annu. Rev. Med., 2010, vol. 61, pp. 359-373.
Smith, Andrew M., et al., "A Systematic Examination of Surface Coatings on the Optical and Chemical Properties of Semiconductor Quantum Dots,"Supplementary Material for Phys. Chem., Chem. Phys., 2006.
Smith, Andrew M., et al., "A systematic examination of surface coatings on the optical and chemical properties of semiconductor quantum dots," Phys. Chem., Chem. Phys., 2006, vol. 8, pp. 3895-3903.
Smith, Andrew M., et al., "Bioconjugated quantum dots for in vivo molecular and cellular imaging," Advanced Drug Delivery Reviews, 2008, vol. 60, pp. 1226-1240.
Smith, Andrew M., et al., "Minimizing the Hydrodynamic Size of Quantum Dots with Multifunctional Multidentate Polymer Ligands," J. Am. Chem. Soc., 2008, vol. 130, pp. 11278-11279.
Smith, Andrew M., et al., "Second window for in vivo imaging," Nat Nanotechnol. Nov. 2009, vol. 4, No. 11, pp. 710-711.
Townsend, David W., "A Combined PET/CT Scanner: The Choices," Journal of Nuclear Medicine, vol. 42, No. 3, pp. 533-534.
van der Vorst, Joost R., et al., "Near-Infrared Fluorescence Imaging of Liver Metastases in Rats using Indocyanine Green," Journal of Surgical Research, 2011, pp. 1-6.
Wang, Xu, et al., "Application of Nanotechnology in Cancer Therapy and Imaging," CA Cancer J Clin 2008, vol. 58, pp. 97-110.
Yamashita, Shin-ichi, et al., "Video-assisted thoracoscopic indocyanine green fluorescence imaging system shows sentinel lymph nodes in non-small-cell lung cancer," The Journal of Thoracic and Cardiovascular Surgery, 2010, pp. 1-5.
Yang, Lily, et al., "Molecular Imaging of Pancreatic Cancer in an Animal Model using Targeted Multifunctional Nanoparticles," Imaging and Advanced Technology, 2009, pp. 1514-1525.
Yang, Lily, et al., "Receptor-Targeted Nanoparticles for in vivo Imaging of Breast Cancer," Clin Cancer Res, Jul. 15, 2009, vol. 15, No. 14, pp. 4722-4732.
Yaseen, Mohammad A., et al., "Biodistribution of Encapsulated Indocyanine Green in Healthy Mice," Molecular Pharmaceutics, 2009, vol. 6, No. 5, pp. 1321-1332.

(56) References Cited

OTHER PUBLICATIONS

Zong, Yuda, et al., "Contrast-Enhanced MRI with New Biodegradable Macromolecular Gd(III) Complexes in Tumor-Bearing Mice," Magnetic Resonance in Medicine, 2005, vol. 53, pp. 835-842.

Zong, Yuda, et al., "Effect of size and charge on pharmacokinetics and in vivo MRI contrast enhancement of biodegradable polydisulfide Gd(III) complexes," Journal of Controlled Release, 2006, vol. 112, pp. 350-356.

Agrawal, Amit, et al., "Nanometer-scale mapping and single-molecule detection with color-coded nanoparticle probes," PNAS, Mar. 4, 2008, vol. 105, No. 9, pp. 3298-3303.

Angel, S.M., et al., "Remote Raman Spectroscopy Using Diode Lasers and Fiber-optic Probes," SPIE, vol. 1435, Optical Methods for Ultrasensitive Detection and Analysis: Techniques and Applications, 1991, pp. 72-81.

Carrabba, Michael M., et al., "Compact Raman instrumentation for process and environmental monitoring," SPIE, vol. 1434, Environmental Sensing and Combustion Diagnostics, 1991, pp. 127-134.

Carrabba, Michael M., et al., "The prospect of utilizing surface enhanced Raman spectroscopy (SERS) for bio- and biomedical sensing," SPIE, vol. 1201, Optical Fibers in Medicine V, 1990, pp. 438-446.

DaCosta, Ralph S., et al., "Spectroscopy and fluorescence in esophageal diseases," Best Practice & Research Clinical Gastroenterology, 2006, vol. 20, No. 1, pp. 41-57.

De Grand, Alec M., "An Operational Near-Infrared Fluorescence Imaging System Prototype for Large Animal Surgery," Technology in Cancer Research & Treatment, Dec. 2003, vol. 2, No. 6, pp. 553-562.

de Veld, Diana C., et al., "Clinical study for classification of benign, dysplastic, and malignant oral lesions using autofluorescence spectroscopy," Journal of Biomedical Optics, (Sep./Oct. 2004), vol. 9, No. 5, pp. 940-950.

Draga, Ronald O. P., et al., "In Vivo Bladder Cancer Diagnosis by High-Volume Raman Spectroscopy," Analytical Chemistry, 2010, vol. 82, No. 14, pp. 5993-5999. (Pre-Print).

Dreher, Matthew R., et al., "Tumor Vascular Permeability, Accumulation, and Penetration of Macromolecular Drug Carriers," Journal of the National Cancer Institute, Mar. 1, 2006, vol. 98, No. 5, pp. 335-344.

Feng, Yi, et al., "Characterization of Tumor Angiogenesis with Dynamic Contrast-Enhanced MRI and Biodegradable Macromolecular Contrast Agents in Mice," Magnetic Resonance in Medicine, 2008, vol. 60, pp. 1347-1352.

Gambhir, Sanjiv Sam, "Molecular Imaging of Cancer with Positron Emission Tomography," Nature Reviews/Cancer, Sep. 2002, vol. 2, pp. 683-693.

Gao, Xiaohu, et al., "In vivo cancer targeting and imaging with semiconductor quantum dots," Nature Biotechnology, Aug. 2004, vol. 22, No. 8, pp. 969-976.

Gao, Xiaohu, et al., "In vivo molecular and cellular imaging with quantum dots," Current Opinion in Biotechnology, 2005, vol. 16, pp. 63-72.

Haka, Abigail S., et al., "Diagnosing breast cancer by using Raman spectroscopy," PNAS, Aug. 30, 2005, vol. 102, No. 35, pp. 12371-12376.

Haka, Abigail S., et al., "In vivo Margin Assessment during Partial Mastectomy Breast Surgery using Raman Spectroscopy," Cancer Res, Mar. 15, 2006, vol. 66, No. 6, pp. 3317-3322.

Hanahan, Douglas, et al., The Hallmarks of Cancer, Cell, Jan. 7, 2000, vol. 100, pp. 57-70.

Jain, Rakesh K., "Transport of Molecules, Particles, and Cells in Solid Tumors," Annu. Rev. Biomed. Eng. 1990, vol. 1, pp. 241-263, and pp. C1-C5.

Joshi, Bishnu P., et al., "Exogenous Molecular Probes for Targeted Imaging in Cancer: Focus on Multi-modal Imaging," Cancers, 2010, vol. 2, pp. 1251-1287.

Kairdolf, Brad A., et al., "Hydroxyl-Derivatized Surface Coatings for Minimizing Nonspecific Binding of Nanoparticles," Analytical Chemistry, 2008, vol. 80, No. 8, pp. 3029-3034. (Abstract).

Kairdolf, Brad A., et al., Synthesis, Encapsulation, and Solubilization of Size-Tuned Quantum Dots with Amphiphilic Multidentate Ligands, Journal of the American Chemical Society, 2008, vol. 130, No. 39, pp. 12866-12867. (Abstract).

Kanter, Elizabeth M., et al, "Effect of hormonal variation on Raman spectra for cervical disease detection," American Journal of Obstetrics & Gynecology, May 2009, pp. 512.e1-512.e5.

Kanter, Elizabeth M., et al., "Application of Raman spectroscopy for cervical dysplasia diagnosis," J. Biophoton, 2009, vol. 2, No. 1-2, pp. 81-90.

Karakiewicz, Pierre I., et al., "Prognostic Impact of Positive Surgical Margins in Surgically Treated Prostate Cancer: Multi-Institutional Assessment of 5831 Patients," Urology, 2005, vol. 66, No. 6, pp. 1245-1250.

Karni, Tami, et al., "A device for real-time, intraoperative margin assessment in breast-conservation surgery," The American Journal of Surgery, 2007, vol. 194, pp. 467-473.

Kuvshinoff, Boris, et al., "Distal Margin Requirements After Preoperative Chemoradiotherapy for Distal Rectal Carcinomas: Are < 1 cm Distal Margins Sufficient?" Annals of Surgical Oncology, 2001, vol. 8, No. 2, pp. 163-169.

Li, Shyh-Dar, et al., Pharmacokinetics and Biodistribution of Nanoparticles, Molecular Pharmaceutics, 2008, vol. 5, No. 4, pp. 496-504. (Pre-Print).

Liu, Jian, et al., "Molecular Mapping of Tumor Heterogeneity on Clinical Tissue Specimens with Multiplexed Quantum Dots," ACS Nano, 2010, vol. 4, No. 5, pp. 2755-2765.

Liu, Jian, et al., "Multiplexed Detection and Characterization of Rare Tumor Cells in Hodgkin's Lymphoma with Multicolor Quantum Dots," Anal. Chem., 2010, vol. 82, pp. 6237-6243.

Low, Donald E., et al., "Nd-YAG Laser Photoablation of Sessile Villous and Tubular Adenomas of the Colorectum," Ann. Surg., Dec. 1988, From the Departments of Surgery and Gastroenterology, Virginia Mason Medical Center, Seattle, Washington, pp. 725-732.

Lu, Zheng-Rong, et al., "Polydisulfide Gd(III) chelates as biodegradable macromolecular magnetic resonance imaging contrast agents," International Journal of Nanomedicine, 2006, vol. 1, No. 1, pp. 31-40.

Mancini, Michael C., "Biomedical Instrumentation and Nanotechnology for Image-Guided Cancer Surgery," A Dissertation Presented to the Academic Faculty, Georgia Institute of Technology, Emory University, May 2011.

Mancini, Michael C., et al., "Oxidative Quenching and Degradation of Polymer-Encapsulated Quantum Dots: New Insights into the Long-Term Fate and Toxicity of Nanocrystals in Vivo," J. Am. Chem. Soc., 2008, vol. 130, pp. 10836-10837.

Matsumura, Yasuhiro, et al., "A New Concept for Macromolecular Therapeutics in Cancer Chemotherapy: Mechanism of Tumoritropic Accumulation of Proteins and the Antitumor Agent Smancs," Cancer Research, Dec. 1986, vol. 46, pp. 6387-6392.

Meric, Funda, et al., "Positive Surgical Margins and Ipsilateral Breast Tumor Recurrence Predict Disease-Specific Survival After Breast-Conserving Therapy," Cancer, 2003, vol. 97, p. 926-933.

Minchinton, Andrew I., et al., "Drug penetration in solid tumours," Nature Reviews/Cancer, Aug. 2006, vol. 6, pp. 583-592.

Mishra, Amaresh, et al., "Cyanines during the 1990s: A Review," Chem. Rev. 2000, 100, 1973-2011.

Mo, Jianhua, et al, "High Wavenumber Raman Spectroscopy for in Vivo Detection of Cervical Dysplasia," Anal. Chem., 2009, vol. 81, pp. 8908-8915.

Mohs, Aaron M., "Proton-Resistant Quantum Dots: Stability in Gastrointestinal Fluids and Implications for Oral Delivery of Nanoparticle Agents," Nano Res., (2009), vol. 2, pp. 500-508.

Mohs, Aaron M., et al, "Hand-held Spectroscopic Device for In Vivo and Intraoperative Tumor Detection: Contrast Enhancement, Detection Sensitivity, and Tissue Penetration," Anal. Chem., 2010, vol. 82, pp. 9058-9065.

Mohs, Aaron M., et al., "A handheld spectroscopy device with integrated wide-field imaging for intraoperative, contrast-enhanced tumor detection." Presentation at the Annual Meeting of the Biomedical Engineering Society, Austin, TX, Oct. 2010.

(56) References Cited

OTHER PUBLICATIONS

Mohs, Aaron M., et al., Applications of Nanotechnology to Imaging and Therapy of Brain Tumors, Neuroimag Clin N. Am., 2010, vol. 20, pp. 283-292.

Mohs, Aaron M., et al., "Gadolinium(III)-based blood-pool contrast agents for magnetic resonance imaging: status and clinical potential," Expert Opin. Durg Deliv, 2004, vol. 4, No. 2, pp. 1-16.

Mohs, Aaron M., et al., "Intraoperative detection of fluorescent nanoparticles using a handheld spectroscopic pen device to guide tumor resection," Poster Presentation at the American Association for Cancer Research, Nano in Cancer Meeting, Miami, FL, Jan. 14, 2011.

Mohs, Aaron M., et al., "Modification of Gd-DTPA Cystine Copolymers With PEG-1000 Optimizes Pharmacokinetics and Tissue Retention for Magnetic Resonance Angiography," Magnetic Resonance in Medicine, 2005, vol. 58, pp. 110-118.

Mohs, Aaron M., et al., "PEG-g-poly(GdDTPA-co-I-cystine): A Biodegradable Macromolecular Blood Pool Contrast Agent for MRI Imaging," Bioconjugate Chem., 2004, vol. 15, pp. 1424-1430.

Mohs, Aaron M., et al., "PEG-g-poly(GdDTPA-co-I-cystine): Effect of PEG Chain Length on in Vivo Contrast Enhancement in MRI," Biomacromolecules, 2005, vol. 6, pp. 2305-2311.

Müller, Markus G., et al., "Spectroscopic Detection and Evaluation of Morphologic and Biochemical Changes in Early Human Oral Carcinoma," Cancer, Apr. 1, 2003, vol. 97, No. 7, pp. 1681-1692.

Neoptolemos, John P., et al., "Influence of Resection Margins on Survival for Patients with Pancreatic Cancer Treated by Adjuvant Chemoradiation and/or Chemotherapy in the ESPAC-1 Randomized Controlled Trial," Annals of Surgery, 2001, vol. 234, No. 6, pp. 758-768.

Ngô, Charlotte, et al., "Intraoperative Ultrasound Localization of Nonpalpable Breast Cancers," Annals of Surgical Oncology, 2007, vol. 14, No. 9, pp. 2485-2489.

Jonak, Constanze, et al., "Intradermal Indocyanine Green for In Vivo Fluorescence Laser Scanning Microscopy of Human Skin: A Pilot Study," Plos ONE, Aug. 2011, vol. 6, Issue 8, e23972, pp. 1-10.

PCT International Search Report and Written Opinion for International Application No. PCT/US2014/063923 dated Apr. 24, 2015.

English Translation of Japanese Office Action mailed Sep. 9, 2015 for patent application No. JP 2012-544798.

* cited by examiner

ADDITIONAL SYSTEMS AND METHODS FOR PROVIDING REAL-TIME ANATOMICAL GUIDANCE IN A DIAGNOSTIC OR THERAPEUTIC PROCEDURE

CROSS REFERENCE TO RELATED APPLICATIONS

This application claims the benefit of priority to U.S. Provisional Application No. 61/412,984, filed Nov. 12, 2010, the disclosure of which is incorporated herein by reference in its entirety.

STATEMENT OF FEDERALLY-SPONSORED RESEARCH

This invention was made with government support under Grant No. U54 CA011933 awarded by the National Institutes of Health. The government has certain rights in the invention.

FIELD OF THE DISCLOSURE

The present disclosure generally relates to systems and methods for intra-operatively providing guidance in a diagnostic or therapeutic procedure.

BACKGROUND

In many areas of surgery, there is a need for anatomical guidance and rapid pathology to be provided during a diagnostic or therapeutic procedure. In the area of surgical oncology, for example, there is a need to determine if a tumor has been completely resected, such as by verifying that the margin of resected tumor tissue is clear, without having to wait for pathology to process the resected tissue to verify that there are no remaining signs of cancerous growth in the margin.

Similarly, medical and biomedical practices often involve the visualization of human or other biological tissues as a means of detecting pathology, including the detection of cancer or pre-cancerous lesions. Such practices may include, but are not limited to, physical examination, endoscopic examinations or treatments, or procedures employing other imaging technologies, such as radiography, fluoroscopy, tomography, computerized tomography, magnetic resonance studies, positron emission tomography, or nuclear medical scans. Such imaging systems may detect abnormalities suggestive of pathology like cancer, but lack a real-time, definitive capacity to actually diagnose the presence (or absence) of such pathology in real-time in the tissues examined. Therefore, a heretofore unaddressed need still exists in the art to address the aforementioned deficiencies and inadequacies.

SUMMARY

In one aspect, the present disclosure relates to a system for intra-operatively providing anatomical guidance in a diagnostic or therapeutic procedure. In one embodiment, the system includes a first light source that is configured to emit a beam of visible light to an area of interest of a living subject and a second light source that is configured to emit a beam of near-infrared light to the area of interest. The system also includes a handheld probe that is optically coupled to the second light source, and that includes an optical fiber that is configured to deliver the emitted beam of near-infrared light to illuminate the area of interest. The optical fiber is also configured to collect light that is scattered or light that is emitted from a contrast agent introduced into target tissues in the area of interest, in response to illumination by the second light source. A first electronic imaging device is also included in the system. The first electronic imaging device is optically coupled to the handheld probe and is configured to detect the collected light and to generate a corresponding signal that includes collected light data. The handheld probe is further configured to transmit the collected light to the first electronic imaging device through the optical fiber. The system further includes a second electronic imaging device that is configured to detect visible light that is emitted from the area of interest in response to illumination by the first light source, and to generate a corresponding signal including visible light data. A third electronic imaging device is also included in the system, which is configured to detect near-infrared light having a first predetermined wavelength that is emitted from the area of interest, in response to illumination by the second light source, and which is also configured to generate a corresponding signal including a first set of near-infrared light data. In addition, the system includes a fourth electronic imaging device that is configured to detect near-infrared light having a second predetermined wavelength that is different from the first predetermined wavelength and that is emitted from the area of interest, in response to illumination by the second light source, and the fourth electronic imaging device is also configured to generate a corresponding signal that includes a second set of near-infrared light data. A display for displaying at least one visual representation of data is further included in the system. A speaker for producing at least one auditory representation of the data can be further included in the system if desired. Also, the system includes a controller that is in communication with each of the first light source, second light source, first electronic imaging device, second electronic imaging device, third electronic imaging device, fourth electronic imaging device, display, and speaker. The controller is programmed to generate at least one real-time integrated visual representation of the area of interest from each of the collected light data, visible light data, first set of near-infrared light data, and second set of near-infrared light data, and to display at least one real-time visual representation on the display for guidance during the diagnostic or therapeutic procedure.

In an embodiment, the contrast agent includes a Raman probe and/or a fluorescence probe and the collected light data includes Raman data and/or fluorescence data, respectively. In this embodiment, the integrated visual representation includes a wide-field image of the area of interest that is generated from the visible light data, a laser excitation image of a selected area of the area of interest that is defined within the wide-field image and that is generated from at least one of the generated first set of near-infrared light data and the generated second set of near-infrared light data, and a Raman image generated from the Raman data and/or a fluorescence image generated from the fluorescence data. The Raman image and/or fluorescence image is defined within the wide-field image and the laser excitation image, as an overlay image on the laser excitation image.

In an embodiment, the first electronic imaging device includes a spectrometer and each of the second electronic imaging device, third electronic imaging device, and fourth electronic imaging device includes a CCD or CMOS camera.

In another aspect, the present disclosure relates to an imaging system using integrated bright-field imaging, near-infrared imaging, and Raman imaging and/or fluorescence imaging for intra-operatively evaluating target tissues in an area of interest of a living subject. In one embodiment, the system includes a first light source for delivering a beam of visible light to the area of interest and a second light source for delivering a beam of near-infrared light to the area of interest. The system also includes a Raman and/or fluorescence imaging means that includes a handheld probe optically coupled to the second light source, for delivering the near infrared light to illuminate target tissues of the area of interest, and for collecting scattered light and/or emitted light from a corresponding Raman probe and/or fluorescence probe that is introduced into the target tissues and illuminated by the second light source. The system further includes a first electronic imaging device that is in communication with the handheld probe, for obtaining Raman data and/or fluorescence data from the collected light. In this embodiment, the first electronic imaging device includes a spectrometer. A bright-field imaging means is also included in the system according to this embodiment. The bright-field imaging means includes: an optical port; a system lens including a UV-NIR compact lens and a first achromatic correction lens; a silver mirror; a first shortpass dichroic mirror and a second shortpass dichroic mirror; a neutral density filter; a bandpass filter; a longpass filter; a second achromatic lens, a third achromatic lens, and a fourth achromatic lens; a second electronic imaging device for obtaining visible light data from visible light emitted from the area of interest in response to illumination by the first light source; a third electronic imaging device for obtaining a first set of near-infrared data from light having a first predetermined wavelength that is emitted from the area of interest in response to illumination by the second light source; and a fourth electronic imaging device for obtaining a second set of near infrared data from light having a second predetermined wavelength that is different from the first predetermined wavelength and that is emitted from the area of interest in response to illumination by the second light source. Each of the second electronic imaging device, third electronic imaging device, and fourth electronic imaging device include a CCD or CMOS camera.

In an embodiment, the optical port and the first electronic imaging device define a first optical path between them that includes the silver mirror, the first shortpass dichroic mirror, the second shortpass dichroic mirror, and the second achromatic lens, where the optical port and the second electronic imaging device define a second optical path between them that includes the silver mirror, first shortpass dichroic mirror, second shortpass dichroic mirror, neutral density filter, and third achromatic lens. The optical port and the third electronic imaging device define a third optical path between them that includes the silver mirror, first shortpass dichroic mirror, longpass filter, bandpass filter, and fourth achromatic lens. The system of this embodiment also includes a display for displaying at least one visual representation of data, and a controller in communication with each of the first light source, second light source, first electronic imaging device, second electronic imaging device, third electronic imaging device, fourth electronic imaging device, and display. The controller is programmed for generating in real-time an integrated visual representation of the area of interest from the collected light data, first set of near-infrared data, second set of near-infrared data, and displaying the integrated visual representation on the display, to provide guidance for performing a diagnostic or therapeutic procedure.

In an embodiment, the real-time integrated visual representation of the area of interest includes a wide-field image of the area of interest generated from the visible light data, a laser excitation image of a predetermined area defined within the wide-field image that is generated from the first set of near-infrared data and/or the second set of near-infrared data, and a Raman image and/or fluorescence image that is defined within the laser excitation image and that is generated from corresponding Raman data and/or fluorescence data. The Raman image and/or fluorescence image is an overlay image on the laser excitation image.

In an embodiment, the real-time aural representation of the area of interest includes one of either a tone or a series of "clicks", having a tone with frequency representative of a level of the signal exceeding a predefined threshold level, or having a series of clicks with rate representative of a level of the signal exceeding a predefined threshold level, generated from at least one of a Raman image and a fluorescence image that is generated from a corresponding at least one of the Raman data and fluorescence data. The Raman data and/or fluorescence data is represented by the signal that, when exceeding a predefined threshold level, signifies disease in the target tissues.

In an embodiment, the at least one integrated visual representation of the area of interest includes a wide-field image of the area of interest generated from the visible light data, a laser excitation image of a predetermined area defined within the wide-field image that is generated from at least one of the first set of near-infrared data and the second set of near-infrared data, and at least one of a Raman image and a fluorescence image that is generated from a corresponding at least one of the Raman data and fluorescence data. The laser excitation image is an overlay image on the wide-field image and represents the location of the delivered beam of near-infrared light within the area of interest. The Raman data and/or fluorescence data is represented by a signal that, when exceeding a predefined threshold level, signifies disease in the target tissues.

Further, the Raman image and/or the fluorescence image is a color overlay image on the laser excitation image, having an opacity representative of the level of the signal exceeding the predefined threshold level, and the opacity of the color overlay image decays over time to be progressively more translucent relative to the laser excitation image.

In yet another aspect, the present disclosure relates to a method for intra-operatively providing anatomical guidance in a diagnostic or therapeutic procedure. In one embodiment, the method includes the steps of introducing at least one contrast agent into target tissues in an area of interest of a living subject, and the step of emitting a beam of visible light to the area of interest, using a first light source. The method also includes the step of emitting a beam of near-infrared light to the area of interest, using a second light source, and the step of delivering the emitted beam of near-infrared light to illuminate the area of interest, using an optical fiber of a handheld probe that is optically coupled to the second light source. In addition, the method includes the step of collecting scattered light and/or emitted light from the contrast agent in response to illumination by the second light source, using the optical fiber of the handheld probe. The contrast agent includes a Raman probe and/or a fluorescence probe. Further, the method includes the step of detecting the collected light and generating a corresponding signal that includes collected light data, using a first electronic imaging device that is optically coupled to the optical fiber, where the optical fiber is further configured to deliver the collected light to the first electronic imaging device. The method also includes the step of detecting visible light that is emitted from the area of interest in response to illumination by the first light source and generating a corresponding signal comprising visible light data, using a second electronic imaging device, and the step of detecting near-infrared light having a first predetermined wavelength that is emitted from the area of interest in response to illumination by the second light source and generating a corresponding signal that includes a first set of near-infrared light data, using a third electronic imaging device. Still further, the method includes the step of detecting near-infrared light having a second predetermined wavelength that is different from the first predetermined wavelength and that is emitted from the area of interest in response to illumination by the second light source, and generating a corresponding signal that includes a second set of near-infrared light data, using a fourth electronic imaging device, and the step of generating at least one real-time integrated visual representation of the area of interest from the collected light data, visible light data, first set of near-infrared data, and second set of near-infrared data, using a controller that is in communication with each of the first electronic imaging device, second electronic imaging device, third electronic imaging device, and fourth electronic imaging device.

The method also includes the step of displaying the real-time integrated visual representation generated by the controller, for guidance during a diagnostic or therapeutic procedure, using a display that is in communication with the controller. The method also includes the step of producing a real-time auditory representation generated by the controller, for guidance during a diagnostic or therapeutic procedure, using a speaker that is in communication with the controller.

In an embodiment, the step of generating the real-time integrated visual representation of the area of interest includes the steps of generating a wide-field image of the area of interest from the visible light data, generating a laser excitation image of a selected area of the area of interest that is defined within the wide-field image, from the first set of near-infrared light data and/or the second set of near-infrared light data, and generating a Raman image and/or a fluorescence image from the collected light data that is defined within the wide-field image and the laser excitation image. The Raman image and/or fluorescence image is an overlay image on the laser excitation image.

In an embodiment, the first electronic imaging device includes a spectrometer, and each of the second electronic imaging device, third electronic imaging device, and fourth electronic imaging device includes a CCD or CMOS camera.

In yet another aspect, the present disclosure relates to software stored on a computer-readable medium that is programmed for causing a controller to perform functions for intra-operatively providing anatomical guidance in a diagnostic or therapeutic procedure. In one embodiment, the functions include causing a first light source in communication with the controller to emit a beam of visible light to an area of interest of a living subject, causing a second light source optically coupled to an optical fiber and in communication with the controller to emit a beam of near-infrared light to the area of interest through the optical fiber, and causing the optical fiber of the handheld probe to collect light scattered from a Raman probe and/or light emitted from fluorescence probe, in response to illumination by the second light source. The Raman probe and/or fluorescence probe is introduced into the target tissues in the area of interest. The functions also include causing a first electronic imaging device that is in communication with the controller and the optical fiber to detect the collected light, and causing the first electronic imaging device to generate a signal from the collected light that includes Raman data and/or fluorescence data. Further, the functions include causing a second electronic imaging device that is in communication with the controller to detect visible light that is emitted from the area of interest in response to illumination by the first light source, causing the second electronic imaging device to generate a corresponding signal comprising visible light data, causing a third electronic imaging device that is in communication with the controller to detect near-infrared light having a first predetermined wavelength that is emitted from the area of interest in response to illumination by the second light source, and causing the third electronic imaging device to generate a corresponding signal that includes a first set of near-infrared light data.

In addition, the functions include causing a fourth electronic imaging device that is in communication with the controller to detect near-infrared light having a second predetermined wavelength that is different from the first predetermined wavelength and that is emitted from the area of interest in response to illumination by the second light source, and causing the fourth electronic imaging device to generate a corresponding signal that includes a second set of near-infrared light data. Further, the functions include generating at least one real-time integrated visual representation of the area of interest from the visible light data, first set of near-infrared data, second set of near-infrared data, and from the Raman data and/or fluorescence data, and causing a display in communication with the controller to display the generated real-time integrated visual representation for guidance during a diagnostic or therapeutic procedure.

In an embodiment, the function of generating the real-time integrated visual representation of the area of interest includes the steps of generating a wide-field image of the area of interest from the visible light data, generating a laser excitation image of a selected area of the area of interest that is defined within the wide-field image from the first set near-infrared light data and/or the second set of near-infrared light data, and generating a Raman image from the Raman data and/or a fluorescence image from the fluorescence data, that is defined within the wide-field image and the laser excitation image.

In an embodiment, the Raman image and/or fluorescence image is an overlay image on the laser excitation image. The first electronic imaging device includes a spectrometer, and each of the second electronic imaging device, third electronic imaging device, and fourth electronic imaging device includes a CCD or CMOS camera.

In yet another aspect, the present disclosure relates to a method for intra-operatively identifying disease in target tissues in an area of interest of a living subject, to be resected in a diagnostic or therapeutic procedure. In one embodiment, the method includes the step of introducing a Raman probe and/or a fluorescence probe into the area of interest until the probe has accumulated in the target tissues, the step of preparing the living subject and the area of interest for a diagnostic or therapeutic procedure, and the step of initializing an imaging system for integrated bright-field imaging, near-infrared imaging, and Raman imaging and/or fluorescence imaging. The method also includes the step of beginning the diagnostic or therapeutic procedure in the area of interest, the step of using a first real-time integrated visual representation of the area of interest and the target tissues that is generated by the imaging system to identify a boundary of the target tissues that are diseased, and the step of performing a surgical resection of the identified diseased target tissues within the boundary. Further, the method includes the steps of, after the surgical resection, using a second displayed real-time integrated visual representation of the area of interest and the target tissues, generated by the imaging system, to identify any remaining diseased target tissues within the boundary, and if any remaining diseased target tissues are identified, performing a series of further surgical resections on identified remaining diseased target tissues corresponding to a respective series of real-time integrated visual representations generated by the imaging system, until the area of interest is free from diseased target tissues. Further, the method includes the steps of, after the surgical resection, using a third displayed real-time integrated visual representation of specimen of the surgical resection, generated by the imaging system, to identify diseased target tissues within the specimen of the surgical resection, and if any diseased target tissues are identified, marking the diseased areas with a visual aid such that they can be later analyzed by pathologic practice.

In an embodiment, the imaging system includes a first light source that is configured to emit a beam of visible light to an area of interest of a living subject and a second light source that is configured to emit a beam of near-infrared light to the area of interest. The system also includes a handheld probe that is optically coupled to the second light source, and that includes an optical fiber that is configured to deliver the emitted beam of near-infrared light to illuminate the area of interest and that is also configured to collect light that is scattered or light that is emitted from a contrast agent introduced into target tissues in the area of interest, in response to illumination by the second light source. A first electronic imaging device is also included in the system. The first electronic imaging device is optically coupled to the handheld probe and is configured to detect the collected light and to generate a corresponding signal that includes collected light data. The handheld probe is further configured to transmit the collected light to the first electronic imaging device through the optical fiber. The system further includes a second electronic imaging device that is configured to detect visible light that is emitted from the area of interest in response to illumination by the first light source, and to generate a corresponding signal including visible light data. A third electronic imaging device is also included in the system, which is configured to detect near-infrared light having a first predetermined wavelength that is emitted from the area of interest, in response to illumination by the second light source, and which is also configured to generate a corresponding signal including a first set of near-infrared light data. In addition, the system includes a fourth electronic imaging device that is configured to detect near-infrared light having a second predetermined wavelength that is different from the first predetermined wavelength, and that is emitted from the area of interest in response to illumination by the second light source. The fourth electronic imaging device is also configured to generate a corresponding signal that includes a second set of near-infrared light data. A display for displaying at least one visual representation of data is further included in the system. Also, the system can include a controller that is in communication with each of the first light source, second light source, first electronic imaging device, second electronic imaging device, third electronic imaging device, fourth electronic imaging device, display, and speaker. The controller is programmed to generate at least one real-time integrated visual representation of the area of interest from each of the collected light data, visible light data, first set of near-infrared light data, and second set of near-infrared light data, and to display the at least one real-time visual representation on the display for guidance during the diagnostic or therapeutic procedure, and to emit through the speaker an auditory representation of one set of near-infrared light data for guidance during the diagnostic or therapeutic procedure.

In an embodiment of the method, each of the steps of identifying diseased target tissues from the displayed visual representation includes identifying visual representations of the emitted laser excitation light and visual representations of the collected light data that are displayed in a selected area of the visual representation.

In one embodiment, the step of identifying the boundary of the target tissues that are diseased and the step of identifying any remaining diseased target tissues within the boundary includes identifying visual representations of the first set of near-infrared light data, second set of near-infrared light data, and collected light data that are displayed in a selected area of the integrated visual representation. The visual representation of the first set of near-infrared data and second set of near-infrared data is a laser excitation image that represents the location of the delivered beam of near-infrared light within the area of interest, and that is displayed as a color overlay image on the wide-field image.

The signal representing the collected light data that is generated by the first electronic imaging device, when exceeding a predetermined threshold level, signifies disease in the target tissues. The visual representation of the collected light data is a color overlay image on the laser excitation image, having an opacity representative of the level of the signal exceeding the predefined threshold level. The opacity of the color overlay image that represents the collected light data decays over time to be progressively more translucent relative to the laser excitation image. The auditory representation of the collected light data can be one of either a tone or a series of "clicks", for example, having a tone with frequency representative of the level of the signal exceeding the predefined threshold level, or having a series of clicks with rate representative of the level of the signal exceeding the predefined threshold level.

Yet further embodiments include devices and methods of manufacture and use for the imaging system using integrated bright-field imaging, near-infrared imaging, and Raman imaging and/or fluorescence imaging for evaluating target tissues as described herein in real-time combination with an optical system, including, but not limited to, endoscopes, colonoscopes, microscopes, surgical microscopes, arthroscopes, laparoscopes thoracoscopes, mediastinan endoscopes, hysteroscopes, cyctoscopes, ureteroscopes, stereomicroscopes, colposcopes, fiber-optical systems, and rigid optical systems.

Still embodiments include devices and methods of manufacture and use for the imaging system using integrated bright-field imaging, near-infrared imaging, and Raman imaging and/or fluorescence imaging for evaluating target tissues as described herein in real-time combination for concurrent use with therapeutic laser systems.

These and other aspects of the disclosure will become apparent from the following description of the preferred embodiments, taken in conjunction with the following drawings, although variations and modifications therein may be affected without departing from the spirit and scope of the novel concepts of the disclosure. Aspects of this disclosure are provided in US Patent Application Publication No. US2011/0152692 and WO 2011/084528, and in U.S. Provisional Application No. 61/412,984, all of which are incorporated herein by reference in their entireties.

BRIEF DESCRIPTION OF THE DRAWINGS

The accompanying drawings illustrate one or more embodiments and together with the written description, serve to explain the principles of this disclosure. Wherever possible, the same reference numbers are used throughout the drawings to refer to the same or like elements of an embodiment, and wherein the following illustrations are provided.

DETAILED DESCRIPTION

Figure 1A:
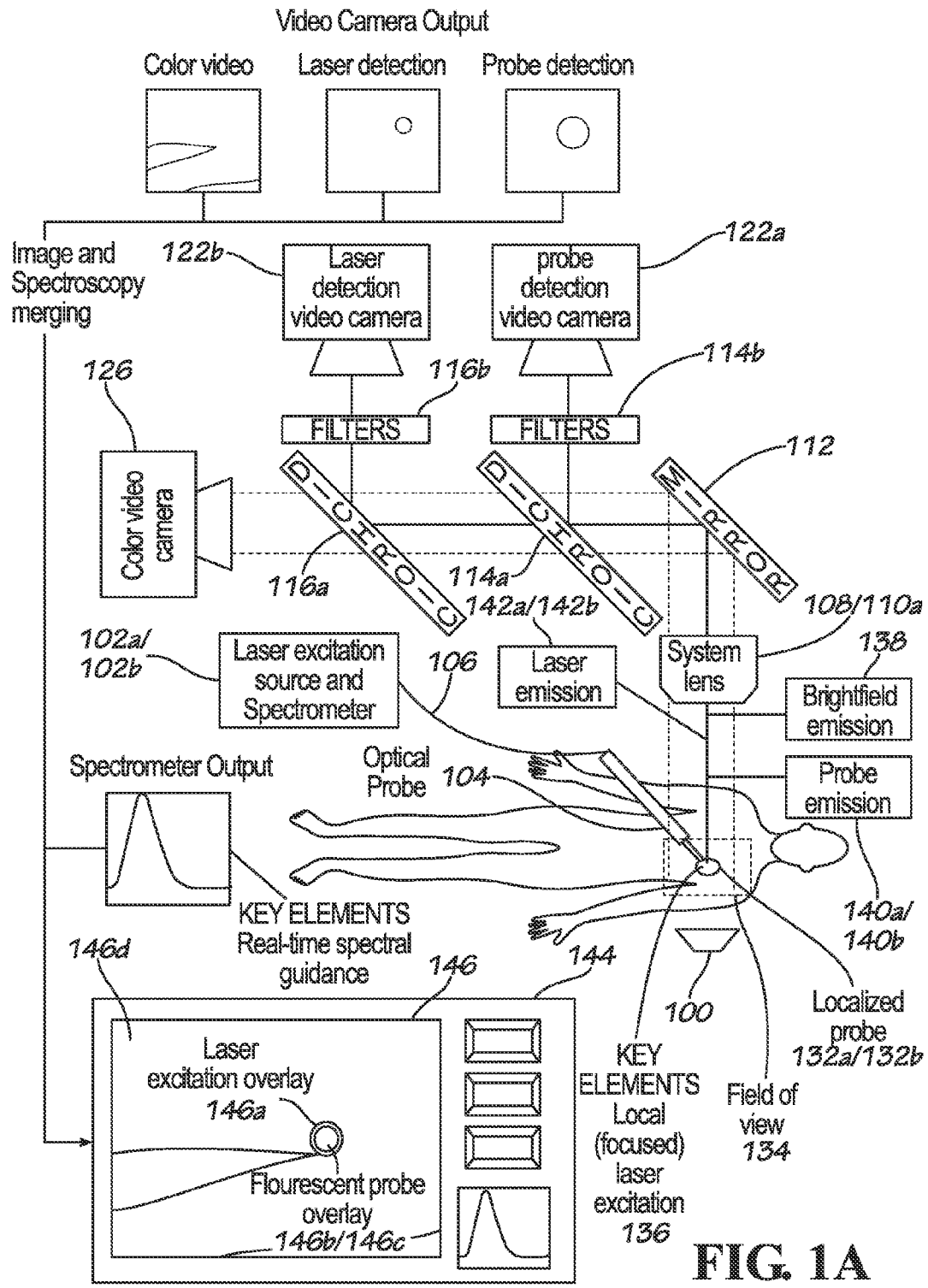
FIG. 1A shows schematically a system for intra-operatively providing anatomical guidance in a diagnostic or therapeutic procedure, using a hand-held optical probe, according to an embodiment. As disclosed, the optical probe can be integral to an endoscopic device or a therapeutic laser system.

The materials, compositions, articles, devices, and methods described herein may be understood more readily by reference to the following detailed description of specific aspects of the disclosed subject matter, and methods and the Examples included therein and to the Figures and their previous and following description.

The following examples are intended as illustrative only because numerous modifications and variations therein will be apparent to those skilled in the art. Various embodiments are now described in detail. Referring to the drawings, like numbers indicate like components throughout the views. As used in the description herein and throughout the claims that follow, the meaning of "a", "an", and "the" includes plural reference unless the context clearly dictates otherwise. Also, as used in the description herein and throughout the claims that follow, the meaning of "in" includes "in" and "on" unless the context clearly dictates otherwise.

As used herein, the terms, "diagnostic procedure" or "therapeutic procedure," encompass any medical or surgical procedure that involves the visualization of tissue surfaces or interior or exterior structures of a subject. These medical or surgical procedures may include but are not limited to, physical examination, open surgical, minimally invasive surgical, endoscopy, colonoscopy, colposcopy, bronchoscopy, thoracoscopy, laryngoscopy, laparoscopy, arthroscopy, cystoscopy, ureteroscopy, in-vivo or ex-vivo microscopy. Further, as used herein, the terms "intra-operatively" and "intra-operative" shall mean during the course of or within the context of any such diagnostic or therapeutic procedure.

The description will be made as to the embodiments in conjunction with the accompanying drawings in the figures.

Figure 1B:
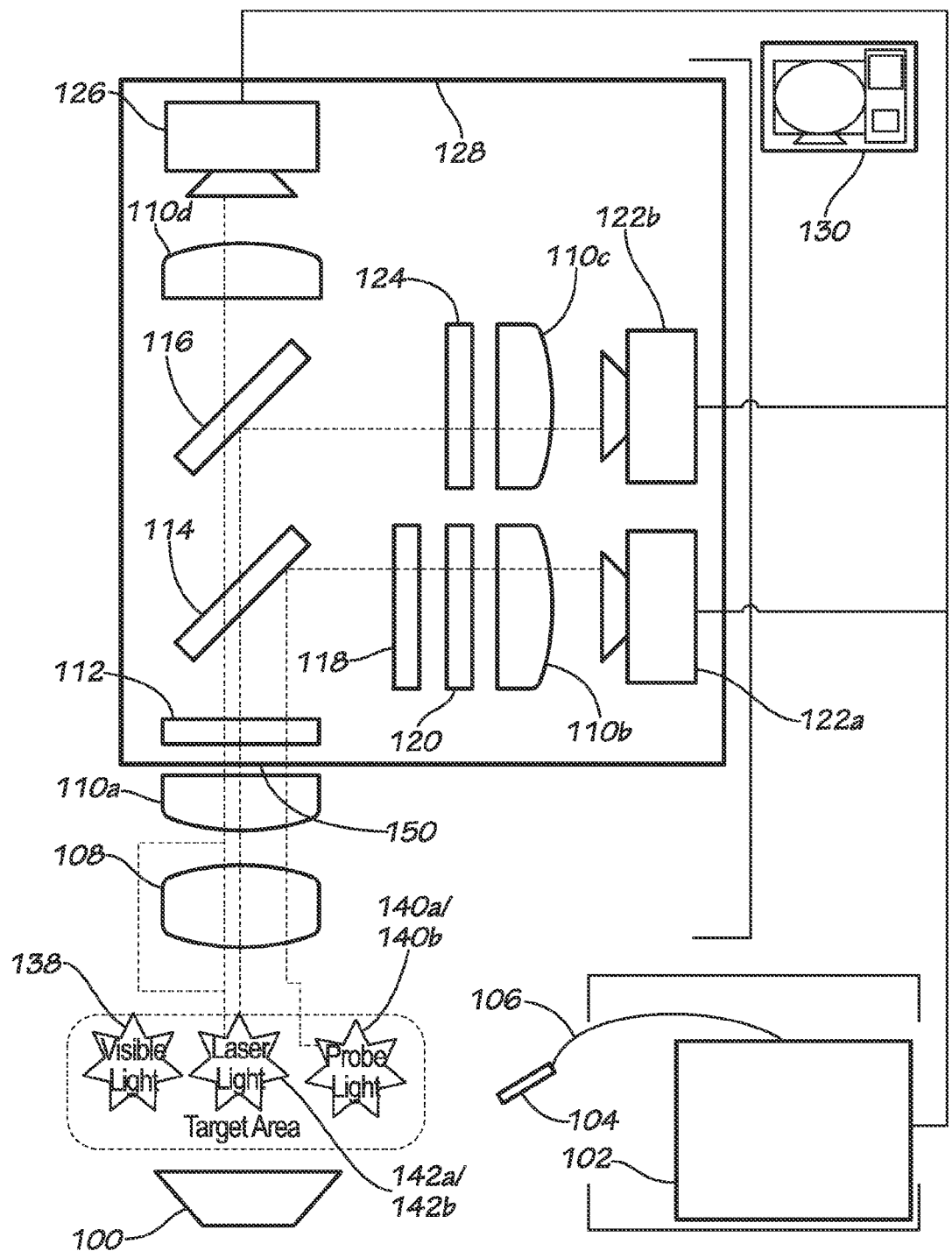
FIG. 1B shows schematically another view of the system according to the embodiment shown in FIG. 1A.

Now referring to FIGS. 1A and 1B, in one aspect, the present disclosure relates to a system for intra-operatively providing anatomical guidance in a diagnostic or therapeutic procedure. With reference to FIGS. 1A and 1B, Chart 1 provides a typical parts list for the fundamental systems and methods for providing read-time anatomical guidance in a diagnostic or therapeutic procedure.

The system may include a first light source 100 that is configured to emit a beam of visible light to an area of interest 134 of a living subject, and a second light source 102a that is configured to emit a beam of near-infrared light to the area of interest 134. The system may also include a handheld probe 104. The handheld probe 104 may be optically coupled to the second light source 102a and may include an optical fiber 106 configured to deliver the emitted beam of near-infrared light to illuminate the area of interest 134. The optical fiber 106 may also be configured to collect light that is scattered 140a and/or or light that is emitted 140b from a contrast agent 132a/132b introduced into target tissues in the area of interest 134, in response to illumination by the second light source 102a.

The first electronic imaging device 102b may be optically coupled to the handheld probe 104 and may be configured to detect the collected light 140a/140b and to generate a corresponding signal that includes collected light data. The handheld probe 104 may be further configured to transmit the collected light 140a/140b to the first electronic imaging device 102b through the optical fiber 106.

The second electronic imaging device 126 may be configured to detect visible light 138 that is emitted from the area of interest 134 in response to illumination by the first light source 100, and to generate a corresponding signal that includes visible light data. The third electronic imaging device 122a may be configured to detect near-infrared light 142a having a first predetermined wavelength that is emitted from the area of interest 134, in response to illumination by the second light source 102a and may also be configured to generate a corresponding signal that includes a first set of near-infrared light data. The fourth electronic imaging device 122b may be configured to detect near-infrared light 142b having a second predetermined wavelength that is different from the first predetermined wavelength and that is emitted from the area of interest 134, in response to illumination by the second light source 102a. The fourth electronic imaging device 122b may also be configured to generate a corresponding signal that includes a second set of near-infrared light data.

The system may also include a display 144 for displaying at least one visual representation of data. Also, the system may include a controller 130 that is in communication with each of the first light source 100, the second light source 102a, the first electronic imaging device 102b, the second electronic imaging device 126, the third electronic imaging device 122a, the fourth electronic imaging device 122b, and the display 144. The controller 130 may be programmed to generate at least one real-time integrated visual representation 146 of the area of interest 134 from each of the collected light data, visible light data, first set of near-infrared light data, and second set of near-infrared light data, and to display the visual representation on the display 144 for guidance during the diagnostic or therapeutic procedure.

In some embodiments, the contrast agent 132a/132b may include a Raman probe 132a and/or a fluorescence probe 132b and the collected light data may include Raman data and/or fluorescence data, respectively. The integrated visual representation 146 may include a widefield image 146d of the area of interest 134 that is generated from the visible light data, and a laser excitation image 146a of a selected area of the area of interest 134 that is defined within the wide-field image 146d. The laser excitation image 146a may be generated from at least one of the generated first set of near-infrared light data and the generated second set of near-infrared light data, and from a Raman image 146b generated from the Raman data and/or a fluorescence image 146c generated from the fluorescence data. The Raman image 146b and/or fluorescence image 146c may be defined within the wide-field image 146d and the laser excitation image 146a, as an overlay image on the laser excitation image 146a.

The first electronic imaging device 102b may include a spectrometer and each of the second electronic imaging device 126, third electronic imaging device 122a, and fourth electronic imaging device 122b may include a CCD or CMOS camera.

In another aspect, the disclosure relates to an imaging system using integrated bright-field imaging, near-infrared imaging, and Raman imaging and/or fluorescence imaging, for intra-operatively evaluating target tissues in an area of interest 134 of a living subject. The system may include a first light source 100 for delivering a beam of visible light to the area of interest 134 and a second light source 102a for delivering a beam of near-infrared light to the area of interest 134. The system may also include a Raman imaging means and/or fluorescence imaging means that may include a handheld probe 104 optically coupled to the second light source 102a, for delivering the near infrared light to illuminate target tissues of the area of interest 134, and for collecting scattered light 140a and/or emitted light 140b from a corresponding Raman probe 132a and/or fluorescence probe 132b that is introduced into the target tissues and illuminated by the second light source 102a. The system may further include a first electronic imaging device 102b that is in communication with the handheld probe 104, for obtaining Raman data and/or fluorescence data from the collected light 140a/140b. The first electronic imaging device 102b may include a spectrometer.

A bright-field imaging means may also be included in the system. The bright-field imaging means may include: an optical port 150; a system lens 108/110a that may include a UV-NIR compact lens 108 and a first achromatic correction lens 110a; a silver mirror 112; a first dichroic mirror 114a and a second dichroic mirror 116a; a first shortpass filter 114b and a second shortpass filter 116b; a neutral density filter 124; a bandpass filter 120; a longpass filter 118; a second achromatic lens 110b, a third achromatic lens 110c, and a fourth achromatic lens 110d; a second electronic imaging device 126 for obtaining visible light data from visible light 138 emitted from the area of interest 134 in response to illumination by the first light source 100; a third electronic imaging device 122a for obtaining a first set of near-infrared data from light 142a having a first predetermined wavelength that is emitted from the area of interest 134 in response to illumination by the second light source 102a; and a fourth electronic imaging device 122b for obtaining a second set of near infrared data from light 142b having a second predetermined wavelength that is different from the first predetermined wavelength and that is emitted from the area of interest 134 in response to illumination by the second light source 102a. Each of the second electronic imaging device 126, third electronic imaging device 122a, and fourth electronic imaging device 122b may include a CCD or CMOS camera.

In some embodiments, the optical port 150 and the first second electronic imaging device 102b may define a first optical path between them that includes the silver mirror 112, the first dichroic mirror 114a, the second dichroic mirror 116a, and the second achromatic lens 110b. The optical port 150 and the fourth electronic imaging device 126 may define a second optical path between them that includes the silver mirror 112, first dichroic mirror 114a, second dichroic mirror 116a, neutral density filter 124, and third achromatic lens 110c. The optical port 150 and the third electronic imaging device 122a may define a third optical path between them that includes the silver mirror 112, first dichroic mirror 114a, longpass filter 118, bandpass filter 120, and fourth achromatic lens 110d. The system may also include the display 144 for displaying at least one visual representation 146 of data, and the controller 130 in communication with each of the first light source 100, second light source 102a, first electronic imaging device 102b, second electronic imaging device 126, third electronic imaging device 122a, fourth electronic imaging device 122b, and display 144.

The controller may be any controller now known or later developed. For example, the controller may be, but is not limited to, a central processing unit, a processor, or a microprocessor. The controller may be coupled directly or indirectly to memory elements. The controller may also be a central processing unit or a processor of a machine, such as a conventional or general-purpose computer, that is capable of executing machine-executable instructions. The computer may also include a random-access memory (RAM), a read-only memory (ROM), and I/O devices to which the controller may be coupled. The controller 130 may be programmed to generate in real-time an integrated visual representation 146 of the area of interest 134 from the collected light data, visible light data, first set of near-infrared data, and second set of near-infrared data. The controller 130 may also be programmed to display the integrated visual representation 146 on the display 144, to provide guidance for performing a diagnostic or therapeutic procedure.

In some embodiments, the real-time integrated visual representation 146 of the area of interest 134 may include a wide-field image 146d of the area of interest 134 that is generated from the visible light data, a laser excitation image 146a of a predetermined area defined within the wide-field image 146d that is generated from the first set of near-infrared data and/or the second set of near-infrared data, and a Raman image 146b and/or fluorescence image 146c that is defined within the laser excitation image 146a and that is generated from corresponding Raman data and/or fluorescence data. The Raman image 146b and/or fluorescence image 146c may be an overlay image on the laser excitation image 146a.

In yet another aspect, the present disclosure relates to a method for intra-operatively providing anatomical guidance in a diagnostic or therapeutic procedure. The method may include the steps of introducing at least one contrast agent 132a/132b into target tissues in an area of interest 134 of a living subject, and the step of emitting a beam of visible light to the area of interest 134, using a first light source 100. The method may also include the step of emitting a beam of near-infrared light to the area of interest 134, using a second light source 102a, and the step of delivering the emitted beam of near-infrared light to illuminate the area of interest 134, using an optical fiber 106 of a handheld probe 104 that is optically coupled to the second light source 102a. In addition, the method may include the step of collecting scattered light 140a and/or emitted light 140b from the contrast agent 132a/132b in response to illumination by the second light source 102a, using the optical fiber 106 of the handheld probe 104. The contrast agent 132a/132b may include a Raman probe 132a and/or fluorescence probe 132b. Further, the method may include the step of detecting the collected light 140a/140b and generating a corresponding signal that includes collected light data, using a first electronic imaging device 102b optically coupled to the optical fiber 106. The optical fiber 106 may be further configured to deliver the collected light 140a/140b to the first electronic imaging device 102b.

The method may also include the steps of detecting visible light 138 that is emitted from the area of interest 134 in response to illumination by the first light source 100 and generating a corresponding signal that includes visible light data, using a second electronic imaging device 126. Further, the method may also include the steps of detecting near-infrared light 142a having a first predetermined wavelength that is emitted from the area of interest 134 in response to illumination by the second light source 102a and generating a corresponding signal that includes a first set of near-infrared light data, using a third electronic imaging device 122a. Still further, the method may include the steps of detecting near-infrared light 142*b* having a second predetermined wavelength that is different from the first predetermined wavelength and that is emitted from the area of interest 134 in response to illumination by the second light source, and generating a corresponding signal including a second set of near-infrared light data, using a fourth electronic imaging device 122*b*. In addition, the method may include the step of generating at least one real-time integrated visual representation 146 of the area of interest 134 from the collected light data, visible light data, first set of near-infrared data, and second set of near-infrared data, using a controller 130 that is in communication with each of the first electronic imaging device 102*b*, second electronic imaging device 126, third electronic imaging device 122*a*, and fourth electronic imaging device 122*b*. The method may further include the step of displaying the real-time integrated visual representation 146 generated by the controller 130, for guidance during a diagnostic or therapeutic procedure, using a display 144 that is in communication with the controller 130.

The step of generating the real-time integrated visual representation 146 of the area of interest 134 may include the steps of generating a wide-field image 146*d* of the area of interest 134 from the visible light data, generating a laser excitation image 146*a* of a selected area of the area of interest 134 that is defined within the wide-field image 146*d*, from the first set of near-infrared light data and/or the second set of near-infrared light data, and generating a Raman image 140*a* and/or a fluorescence image 140*b* from the collected light data, that is defined within the wide-field image 146*d* and the laser excitation image 146*a*. The Raman image 140*a* and/or fluorescence image 140*b* may be an overlay image on the laser excitation image 146*a*.

In some embodiments, one or more contrast agents may be selected for desired tissue responses to allow for a multiplexed system that can simultaneously identify and display fluorescence in differing types of tissues or pathology. Thus, by selecting the appropriate contrast agent, a user could simultaneously and in real-time screen a targeted tissue for various types of cancer or other cellular pathologies.

In further embodiments, the first electronic imaging device 102*b* may include a spectrometer, and each of the second electronic imaging device 126, third electronic imaging device 122*a*, and fourth electronic imaging device 122*b* may include a CCD or CMOS camera.

In yet another aspect, the present disclosure relates to software stored on a computer-readable medium programmed for causing the controller 130 to perform functions for intraoperatively providing anatomical guidance in a diagnostic or therapeutic procedure. A computer-readable medium may be any computer-readable medium now known or later developed. For example, the computer-readable medium may be any apparatus that may include, store, communicate, propagate, or transport the program for use by or in connection with the controller. The computer-readable medium may be electronic, magnetic, optical, electromagnetic, or infrared. Examples of a computer-readable medium may include, but are not limited to, a removable computer diskette, RAM, ROM, a rigid magnetic disk and an optical disk, such as a compact disk-read only memory (CD-ROM), compact disk-read/write (CD-R/W), and DVD.

The functions may include causing a first light source 100 in communication with the controller 130 to emit a beam of visible light to an area of interest 134 of a living subject, causing a second light source 102*a* that is optically coupled to an optical fiber 106 and in communication with the controller 130 to emit a beam of near-infrared light to the area of interest 134 through the optical fiber 106, and causing the optical fiber 106 of the handheld probe 104 to collect light scattered 140*a* from a Raman probe and/or light emitted 140*b* from a fluorescence probe, in response to illumination by the second light source 102*a*. The Raman probe 132*a* and/or fluorescence probe 132*b* may be introduced into the target tissues in the area of interest 134. The functions may also include causing a first electronic imaging device 102*b* that is in communication with the controller 130 and the optical fiber 106 to detect the collected light 140*a*/140*b*, and causing the first electronic imaging device 102*b* to generate a signal from the collected light 140*a*/140*b* that includes Raman data and/or fluorescence data. Further, the functions may include causing a second electronic imaging device 126 that is in communication with the controller 130 to detect visible light 138 that is emitted from the area of interest 134 in response to illumination by the first light source 100, causing the second electronic imaging device 126 to generate a corresponding signal comprising visible light data, causing a third electronic imaging device 122*a* that is in communication with the controller 130 to detect near-infrared light 142*a* having a first predetermined wavelength that is emitted from the area of interest 134 in response to illumination by the second light source 102*a*, and causing the third electronic imaging device 122*a* to generate a corresponding signal that includes a first set of near-infrared light data. In addition, the functions may include causing a fourth electronic imaging device 122*b* that is in communication with the controller 130 to detect near-infrared light 142*b* having a second predetermined wavelength that is different from the first predetermined wavelength and that is emitted from the area of interest 134 in response to illumination by the second light source 102*a*, and causing the fourth electronic imaging device 122*b* to generate a corresponding signal that includes a second set of near-infrared light data. Also, the functions may include generating at least one real-time integrated visual representation 146 of the area of interest 134 from the visible light data, first set of near-infrared data, second set of near-infrared data, and from the Raman data and/or fluorescence data, and causing a display 144 in communication with the controller 130 to display 144 the generated real-time integrated visual representation 146 for guidance during a diagnostic or therapeutic procedure.

In some embodiments, the function of generating the real-time integrated visual representation 146 of the area of interest 134 may include the steps of generating a wide-field image 146*d* of the area of interest 134 from the visible light data, generating a laser excitation image 146*a* of a selected area of the area of interest 134 that is defined within the wide-field image 146*d* from the first set near-infrared light data and/or the second set of near-infrared light data, and generating a Raman image 146*b* from the Raman data and/or a fluorescence image 146*c* from the fluorescence data, that is defined within the wide-field image 146*d* and the laser excitation image 146*a*.

In further embodiments, the Raman image 146*b* and/or fluorescence image 146*c* may be an overlay image on the laser excitation image 146*a*. The first electronic imaging device 102*b* may include a spectrometer, and each of the second electronic imaging device 126, third electronic imaging device 122*a*, and fourth electronic imaging device 122*b* may include a CCD or CMOS camera.

While Chart 1 provides a typical parts list for the fundamental systems and methods for providing read-time anatomical guidance in a diagnostic or therapeutic procedure, additional parts may be required for incorporating this fundamental system into an optical probe integral to an endoscopic device or a therapeutic laser system. For example, the optical probe is integral to an endoscopic device selected from an endoscope, a colonoscope, a microscope, a surgical microscope, an arthroscope, a laparoscope, a thoracoscope, a mediastinan endoscope, a hysteroscope, a cyctoscope, a ureteroscope, a stereomicroscope, a colposcope, a fiber-optical system, or a rigid optical systems. This disclosure provides for both borescope type devices and for video endoscope type endoscopic devices.

Figure 2:
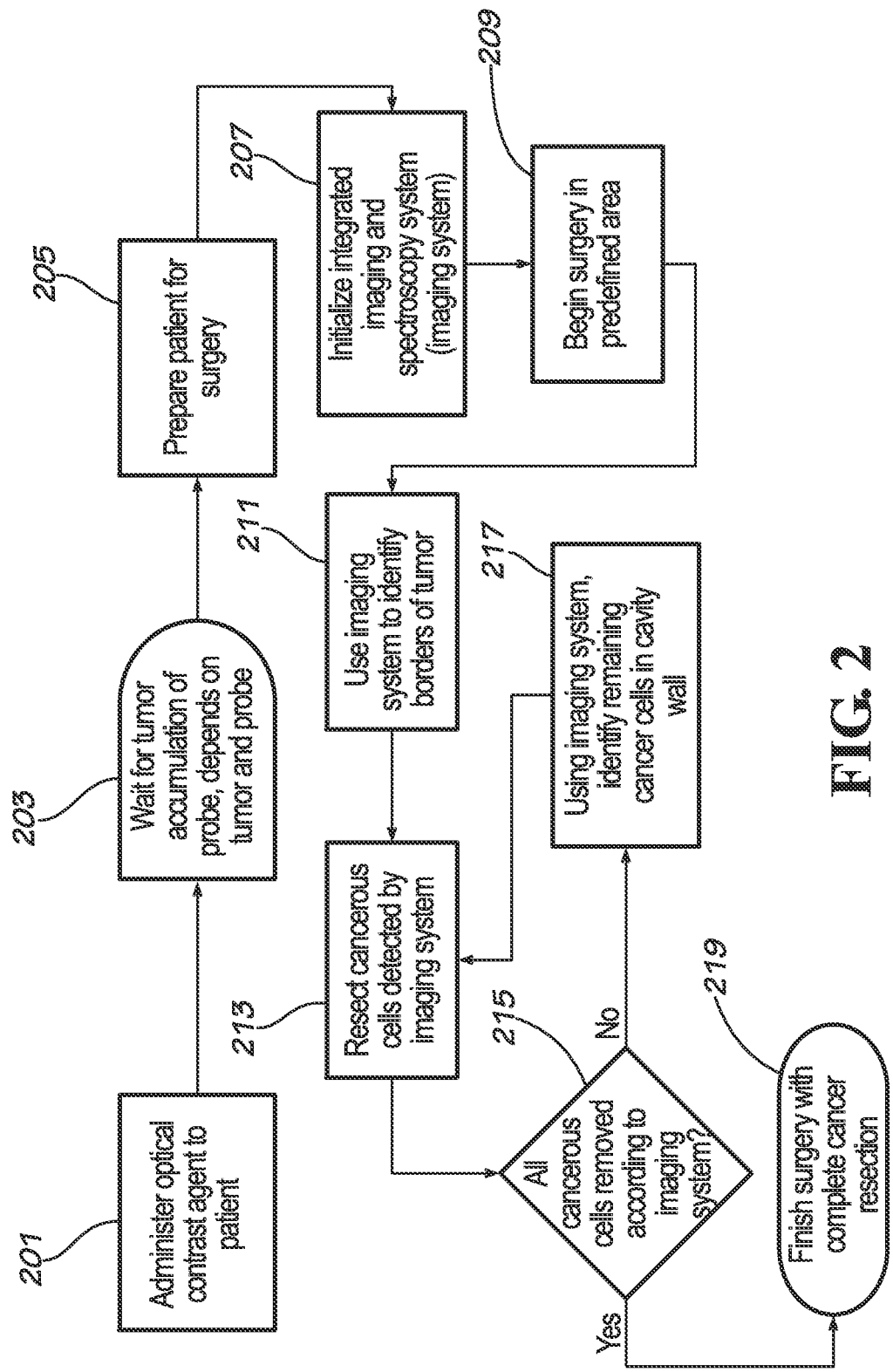
FIG. 2 is a flow chart illustrating the steps of a method for intra-operatively providing anatomical guidance in a diagnostic or therapeutic procedure, using the system according to the disclosed embodiment shown in FIGS. 1A and 1B.

Now referring also to FIG. 2, in yet another aspect, the present disclosure relates to a method for intra-operatively identifying disease in target tissues in an area of interest 134 of a living subject, to be resected in a diagnostic or therapeutic procedure. In one embodiment, the method may include the step 201 of introducing an optical contrast to the living subject, the step 203 of introducing a Raman probe and/or a fluorescence probe into the area of interest 134 until the probe has accumulated in the target tissues, the step 205 of preparing the living subject and the area of interest 134 for a diagnostic or therapeutic procedure, and the step 207 of initializing an imaging system for integrated bright-field imaging, near-infrared imaging, and Raman imaging and/or fluorescence imaging. The method may also include the step 209 of beginning the diagnostic or therapeutic procedure in the area of interest 134, the step 211 of using a first real-time integrated visual representation of the area of interest 134 and the target tissues, generated by the imaging system, to identify a boundary of the target tissues that are diseased, and the step 213 of performing a surgical resection of the identified diseased target tissues within the boundary.

Further, the method may include the step 215 to determine whether all of the cancerous cells have been removed. If it is determined that there are remaining cancerous cells, the method may further include the step 217 of, after the surgical resection, using a second displayed real-time integrated visual representation of the area of interest 134 and the target tissues, generated by the imaging system, to identify any remaining diseased target tissues within the boundary, and the repeat of step 213 of, performing a surgical resection of the identified diseased target tissues within the boundary. The method may include a series of further surgical resections on identified remaining diseased target tissues corresponding to a respective series of real-time integrated visual representations generated by the imaging system, until the area of interest 134 is free from diseased target tissues.

In an embodiment, the imaging system may include a first light source 100 that is configured to emit a beam of visible light to an area of interest 134 of a living subject and a second light source 102a that is configured to emit a beam of near-infrared light to the area of interest 134. The system may also include a handheld probe 104 that is optically coupled to the second light source 102a, and that includes an optical fiber 106 that is configured to deliver the emitted beam of near-infrared light to illuminate the area of interest 134. The optical fiber 106 may also be configured to collect light 140a that is scattered or light 140b that is emitted from a contrast agent 132a/132b introduced into target tissues in the area of interest 134, in response to illumination by the second light source 102a. A first electronic imaging device 102b may also be included in the system. The first electronic imaging device 102b may be optically coupled to the handheld probe 104 and may be configured to detect the collected light 140a/140b and to generate a corresponding signal that includes collected light data. The handheld probe 104 may be further configured to transmit the collected light 140a/140b to the first electronic imaging device 102b through the optical fiber 106. The system may further include a second electronic imaging device 126 that is configured to detect visible light 138 that is emitted from the area of interest 134 in response to illumination by the first light source 100, and to generate a corresponding signal including visible light data. A third electronic imaging device 122a may also be included in the system, which is configured to detect near-infrared light 142a having a first predetermined wavelength that is emitted from the area of interest 134 in response to illumination by the second light source 102a, and which is also configured to generate a corresponding signal including a first set of near-infrared light data. In addition, the system may include a fourth electronic imaging device 122b that is configured to detect near-infrared light 142b having a second predetermined wavelength that is different from the first predetermined wavelength and that is emitted from the area of interest 134, in response to illumination by the second light source 102a. The fourth electronic imaging device 122b may also be configured to generate a corresponding signal that includes a second set of near-infrared light data.

A display 144 for displaying at least one visual representation 146 of data may be further included in the system. Also, the system may include a controller 130 that is in communication with each of the first light source 100, second light source 102a, first electronic imaging device 102b, second electronic imaging device 126, third electronic imaging device 122a, fourth electronic imaging device 122b, and display 144. The controller 130 may be programmed to generate at least one real-time integrated visual representation 146 of the area of interest 134 from each of the collected light data, visible light data, first set of near-infrared light data, and second set of near-infrared light data, and to display the real-time visual representation 146 on the display 144 for guidance during the diagnostic or therapeutic procedure.

In some embodiments, each of the steps of identifying diseased target tissues from the displayed real-time integrated visual representation 146 may include identifying visual representations 146a of the emitted laser excitation light 142a/142b and visual representations 146b/146c of the collected light data displayed in a selected area of the integrated visual representation 146.

While the present disclosure describes a system for intra-operatively providing anatomical guidance in a diagnostic or therapeutic procedure which incorporates a handheld probe optically coupled to the second light source and comprising an optical fiber configured to deliver the emitted beam of near-infrared light to illuminate the area of interest and configured to collect light that is scattered or emitted from a contrast agent introduced into target tissues in the area of interest, this disclosure also provides for incorporating these functions and relevant structures into instruments, probes, and devices that are not necessarily handheld in the manner disclosed in U.S. Patent Application Publication No. 2011/0152692. These latter instruments, probes, and devices encompass and provide more complex integrated functions and additional functions and features that afford advantages in a range of diagnostic or therapeutic procedures.

For example, embodiments may include devices and methods of manufacture and use for the imaging system using integrated bright-field imaging, near-infrared imaging, and Raman imaging and/or fluorescence imaging for evaluating target tissues as described herein in real-time combination with a receiving optical system, including, but not limited to, endoscopes, colonoscopes, microscopes, surgical microscopes, arthroscopes, laparoscopes thoracoscopes, mediastinan endoscopes, hysteroscopes, cyctoscopes, ureteroscopes, stereomicroscopes, colposcopes, fiber-optical systems, and rigid optical systems.

The manner in which these systems can be integrated for providing real-time anatomical guidance in diagnostic and/or therapeutic procedures can utilize those methods and systems that incorporate a borescope or fiberscope type inspection device. Alternatively, the manner in which these systems can be integrated for providing real-time anatomical guidance in diagnostic and/or therapeutic procedures can utilize those methods and systems that incorporate a video endoscope or video borescope type inspection device. In this aspect, integration utilizes the structure and function of each type device and method to both provide real-time imaging.

In the borescope or fiberscope embodiments, the borescope includes a rigid or flexible tube that functions primarily as a conduit for optical information transfer between a proximal site that incorporates electronic imaging devices, light sources, and the like, to and from a distal site at the distal site that includes the necessary or desired optical elements such as lenses, mirrors, filters, or combinations of various optical elements to both deliver and collect light. The promixal and distal sites of the device are linked by, for example, a relay optical system and/or optical fibers used for illumination of the remote object and collecting the reflected, emitted, scattered, Raman, and/or fluorescence data. The linking system can includes a bundle of optical fibers which divide the image into pixels, in the manner of a fiberscope, which can provide desirable flexibility to the device in remote cavities. Thus, the disclosed first electronic imaging device that includes a spectrometer and each of the second electronic imaging device, third electronic imaging device, and fourth electronic imaging device that include a CCD or CMOS camera can be used in the analysis of the collected light data as described herein.

Alternatively, in the video endoscope or video borescope type embodiments, the video endoscope includes a rigid or flexible tube that functions primarily as a conduit for electrical information transfer between a proximal site that incorporates the computational elements and functions to and from a distal site at the distal site that includes electronic imaging devices, light sources, and the like, as well as the necessary or desired optical elements such as lenses, mirrors, filters, or combinations of various optical elements to both deliver and collect light at the distal location. Thus, the video endoscope can be a type of "inspection camera", that uses a miniature electronic, video, and optical components at the end of the flexible tube. Because the more complex optical waveguide structure of the endoscope is replaced with a less expensive electrical cable, video endoscopes are generally less costly and potentially provide enhanced resolution.

Either the borescope (fiberscope) type embodiment or the video endoscope (video borescope) type devices and methods of manufacture and use can be used for the imaging system using integrated bright-field imaging, near-infrared imaging, and Raman imaging and/or fluorescence imaging for evaluating target tissues as described herein in real-time combination with a receiving optical system such as endoscopes, colonoscopes, microscopes, surgical microscopes, arthroscopes, laparoscopes thoracoscopes, mediastinan endoscopes, hysteroscopes, cyctoscopes, ureteroscopes, stereomicroscopes, colposcopes, fiber-optical systems, and rigid optical systems, and the like.

Intelligent Focus

If an adjustable focus lens is installed in the imaging system, an autofocus feature generally is desirable. When the handheld probe is not in use, the system may autofocus using existing methods (e.g. by assessing the level of contrast in a scene). When the handheld probe is in use, the system autofocuses using the laser light emitted by the handheld probe as a guide. The system actuates the motorized focus, and determines the in-focus position based on the position of the motorized focus that either: (1) maximizes the contrast between the laser area and the surroundings, or, (2) minimizes the laser spot size. The method selected depends on the emission profile of the laser, a known quantity. Method 1 is more suitable if the emission profile is a "top-hat" (tracking the laser spot size is a feature already present in the software). Method 2 is more suitable if the emission profile is "Gaussian". In both cases, the software optimizes the lens focus to best match the known laser emission profile. The transition between autofocus based on existing methods and autofocus based on the activation state of the laser and does not require explicit user triggering. Examples of conventional autofocus methods are provided in U.S. Pat. Nos. 5,530,514, 7,058,294, and 7,362,353.

Intelligent Zoom

If the handheld probe is slowly scanned in an area, the imaging system software magnifies the area in which the handheld probe is being used. The additional magnification is activated when the speed of scanning and the size of the area in which scanning occurs are both in a predefined range, and requires no explicit user trigger. When the speed of scanning or area in which the scanning occur fall outsize the predefined range, or when the handheld probe laser is turned off for a predefined period of time, the additional magnification is disabled. The amount of magnification is dependent on both the speed of scanning and the size of the area in which scanning occurs. The additional magnification is achieved digitally by displaying the magnification region-of-interest (ROI) in the same area as the full display. The magnification ROI can be based on the size of the area in which scanning occurs or can be based on the quadrant that bounds the area in which the scanning activity takes place. There can be multiple "layers" of zoom, so that if magnification has been triggered and the scanning activity of the handheld probe is still within the predefined triggering range, the system can increase magnification further. The speed of scanning and size of the area in which the scanning occur are tracked by the imaging system using the laser-tracking camera.

Intelligent Spectroscopy Acquisition and Display

The integration time of the handheld probe spectrometer can be positively correlated to the speed of scanning the probe as follows. The faster the probe is scanned, the shorter the integration time (1); the slower the probe is scanned, the longer the integration time (2). The integration time is set to the intended operator objective: (1) rapid scanning of a large area to find an area to interrogate in detail, or (2) slow scanning of a small area for detailed examination. The "binning" (i.e., the electronic sensor resolution) of the spectrometer is also adjusted to the desired functionality, either with higher binning factors in the case of (1) leading to lower spectral resolution but better sensitivity, or lower binning factors in the case of (2) leading to increased spectral resolution but lesser sensitivity. The power of the laser is positively correlated to the area of laser excitation, so that the irradiance (power per unit area) is maintained constant. The system is able to alert the user, either visually through the system display, or audibly through the system speaker, if the user is holding the probe too close or too far from interrogation area. The determination of "too close" or "too far" is made by comparing the laser excitation area with predetermined minimum and maximum threshold values. The integration time and binning level adjustments are made by the system based on collected data and predefined threshold values for the desired behaviors, and require no explicit user intervention.

The laser power may be automatically adjusted based on the "dwell time" of the laser in the target area. As the laser interrogates an area, it causes photobleaching of the fluorophore in that volume of excitation. The photobleaching rate is in part a factor of the fluorophore used and the laser irradiance. The system can automatically adjust the laser power based on the dwell time, so that when the dwell time for a predefined area exceeds a predefined value, the system attenuates the laser power to a predefined lesser level. The laser power is returned to a previous greater level when the laser exits the area that triggered the attenuation event. There can be multiple levels of laser attenuation. The speed of scanning and size of the laser area is tracked by the imaging system using the laser tracking camera. The attenuation level of the laser power is made by the system based on collected data and predefined threshold values for the desired behaviors, and requires no explicit user intervention. The integration time and binning of the spectrometer, and the gain and binning of the NIR probe camera may also be each increased when the system is using increased laser attenuation to compensate for the lower irradiance of the attenuated laser.

Some of these features are also applicable to the widefield camera system. Thus, when the probe scanning speed exceeds a threshold value, the greater the gain and binning in the NIR probe camera. Similarly, when the probe scanning speed falls below another threshold value, the lower the gain and binning in the NIR probe camera. The scanning speed of the probe is known from the laser-tracking camera. In both cases, adjustments to the gain and binning of the NIR probe camera are made by the system based on collected data and predefined threshold values for the behavior triggers, and require no explicit user intervention.

The laser excitation area can be used to normalize the overlay display of the NIR probe camera, so that a large laser area causes the (virtual) NIR probe display gain to be increased (compensating for lower laser irradiance), and a smaller laser area causes the (virtual) NIR probe display gain to be decreased (compensating for higher laser irradiance). In both cases, the normalization of the overlay display is automatically handled by the system, and requires no explicit user intervention.

Fast Virtual Phosphorescence

When the user elects to use the VP (virtual phosphorescence) filter, an accumulation buffer is initialized. As each new frame is acquired by the NIR camera process, the accumulation buffer is multiplied by a decaying exponential function. The decay constant is user set, and is defined by the amount of time the user would like the display to persist. The decay constant is found by solving the equation $$I(t) = I(0) \cdot e^{-D \cdot t},$$

where I is the pixel intensity in the frame, I(t) is the new pixel intensity at the given time index, e is the base of the natural logarithms, D is the decay constant, and t is the time index. The equation is solved for D and parameterized for the decay time $\tau=t$, using 255 and 1 as the values for $I(0)$ (assuming an 8-bit sensor) and $I(\tau)$, respectively, $$D(\tau) = -\frac{\ln[I(\tau)/I(0)]}{\tau} = -\frac{\ln[1/255]}{\tau}$$

Applying the decay (aging the accumulation buffer) is then done by multiplying every pixel in the accumulation buffer by $$I(s+1) = I(s) \cdot \exp(-D(\tau) \cdot \Delta s)$$

where s is discrete time (between frames), I(s+1) and I(s) are respectively the new and old values of the intensity at the given pixel, exp( ) is the exponential function, $D(\tau)$ is the decay constant calculated in Eq. (4), and $\Delta s$ is the time between frames (i.e., frame interval).

The decay constant can be user set, or it can be automatically set to a predefined value based on the intended activity of the user as determined by the imaging system software. For example, a slow decay is useful when rapidly scanning a large area, whereas a fast decay is useful while interrogating a small area. The intended user activity is determined by the speed of scanning the probe and does not require explicit user input to be determined.

While there have been shown several and alternate embodiments of the present disclosure, it is to be understood that certain changes can be made as would be known to one skilled in the art without departing from the underlying scope of the disclosure as is discussed and set forth above. Furthermore, the embodiments described above are only intended to illustrate the principles of the disclosure and are not intended to limit the scope of the disclosure to the disclosed elements.

Exemplary Aspects and Embodiments

Without intending to limit the scope of the disclosure, exemplary systems and methods according to the embodiments of the present disclosure are provided below.

In one aspect, there is provided a system for intra-operatively providing anatomical guidance in a diagnostic or therapeutic procedure, comprising:
(a) a first light source configured to emit a beam of visible light to an area of interest of a living subject;
(b) a second light source configured to emit a beam of near-infrared light to the area of interest;
(c) an optical probe, which can be integral to an endoscopic device or a therapeutic laser system, optically coupled to the second light source, comprising an optical fiber configured to deliver the emitted beam of near-infrared light to illuminate the area of interest and configured to collect light that is scattered or emitted from a contrast agent introduced into target tissues in the area of interest, in response to illumination by the second light source;
(d) a first electronic imaging device optically coupled to the optical probe and configured to detect the collected light and to generate a corresponding signal that comprises collected light data, and wherein the optical probe is further configured to transmit the collected light to the first electronic imaging device through the optical fiber;
(e) a second electronic imaging device configured to detect visible light that is emitted from the area of interest in response to illumination by the first light source and to generate a corresponding signal comprising visible light data;
(f) a third electronic imaging device configured to detect near-infrared light having a first predetermined wavelength that is emitted from the area of interest in response to illumination by the second light source and to generate a corresponding signal comprising a first set of near-infrared light data;
(g) a fourth electronic imaging device configured to detect near-infrared light having a second predetermined wavelength that is different from the first predetermined wavelength and that is emitted from the area of interest in response to illumination by the second light source, and to generate a corresponding signal comprising a second set of near-infrared light data;
(h) a display for displaying at least one visual representation of data; and
(i) a controller in communication with each of the first light source, second light source, first electronic imaging device, second electronic imaging device, third electronic imaging device, fourth electronic imaging device, and display, and programmed to generate at least one real-time integrated visual representation of the area of interest from each of the collected light data, visible light data, first set of near-infrared light data, and second set of near-infrared light data and to display the at least one real-time visual representation on the display, for guidance during the diagnostic or therapeutic procedure.

A further aspect of this disclosure provides for an imaging system using integrated bright-field imaging, near-infrared imaging, and at least one of Raman imaging and fluorescence imaging for intra-operatively evaluating target tissues in an area of interest of a living subject, comprising:
- (a) a first light source for delivering a beam of visible light to the area of interest and a second light source for delivering a beam of near-infrared light to the area of interest;
- (b) a Raman and fluorescence imaging means, comprising:
  - (i) a optical probe optically coupled to the second light source for delivering the near infrared light to illuminate target tissues of the area of interest and for collecting at least one of scattered light and emitted light from a corresponding at least one of a Raman probe and a fluorescence probe that is introduced into the target tissues and illuminated by the second light source, the optical probe integral to an endoscopic device; and
  - (ii) a first electronic imaging device in communication with the optical probe for obtaining at least one of Raman data from the collected scattered light and fluorescence data from the collected emitted light, respectively; and
- (c) a bright-field imaging means, comprising:
  - (i) a second electronic imaging device for obtaining visible light data from visible light emitted from the area of interest in response to illumination by the first light source;
  - (ii) a third electronic imaging device for obtaining a first set of near-infrared data from light having a first predetermined wavelength that is emitted from the area of interest in response to illumination by the second light source; and
  - (iii) a fourth electronic imaging device for obtaining a second set of near infrared data from light having a second predetermined wavelength that is different from the first predetermined wavelength and that is emitted from the area of interest in response to illumination by the second light source.

In an additional aspect, the bright-field imaging means of the imaging system disclosed above (section c) can further comprise:
- (iv) an optical port;
- (v) a system lens comprising a UV-NIR compact lens and a first focusing lens group;
- (vi) a trichroic prism;
- (vii) a first laser attenuating filter;
- (viii) a bandpass filter;
- (ix) a second laser attenuating filter;
- (x) a second focusing lens group, a third focusing lens group, and a fourth focusing lens group;
  - wherein the optical port and the first electronic imaging device define a first optical path therebetween having the trichroic prism and the second focusing lens group, wherein the optical port and the second electronic imaging device define a second optical path therebetween having the trichroic prism, first laser attenuating filter, and third focusing lens group, and wherein the optical port and the third electronic imaging device define a third optical path therebetween having the trichroic prism, the second laser attenuating filter, bandpass filter, and fourth focusing lens group.

By way of example, and in a further aspect, the bright-field imaging means of the imaging system disclosed above (section c) can further comprise:
- (iv) an optical port;
- (v) a system lens comprising a UV-NIR compact lens and a first collimating or focusing lens group;
- (vi) a silver mirror;
- (vii) a first dichroic mirror and a second dichroic mirror;
- (viii) a first shortpass filter or dichroic mirror and a second shortpass filter or dichroic mirror;
- (ix) a neutral density filter;
- (x) a bandpass filter;
- (xi) a longpass or notch filter; and
- (xii) a second focusing lens group, a third focusing lens group, and a fourth focusing lens group;
  - wherein the optical port and the first electronic imaging device define a first optical path therebetween having the silver mirror, the first dichroic mirror, the second dichroic mirror, and the second focusing lens group; wherein the optical port and the second electronic imaging device define a second optical path therebetween having the silver mirror, first dichroic mirror, second dichroic mirror, neutral density filter, and third focusing lens group, and wherein the optical port and the third electronic imaging device define a third optical path therebetween having the silver mirror, first dichroic mirror, longpass or notch filter, bandpass filter, and fourth focusing lens group.

According to a further aspect, there is provided a method for intra-operatively providing anatomical guidance in a diagnostic or therapeutic procedure, comprising the steps of:
- (a) introducing at least one contrast agent into target tissues in an area of interest of a living subject;
- (b) emitting a beam of visible light to the area of interest, using a first light source;
- (c) emitting a beam of near-infrared light to the area of interest, using a second light source;
- (d) delivering the emitted beam of near-infrared light to illuminate the area of interest, using an optical fiber of a optical probe that is optically coupled to the second light source;
- (e) collecting at least one of scattered light and emitted light from the contrast agent in response to illumination by the second light source, using the optical fiber of the optical probe, wherein the contrast agent comprises at least one of a Raman probe and a fluorescence probe;
- (f) detecting the collected light and generating a corresponding signal that comprises collected light data, using a first electronic imaging device that is optically coupled to the optical fiber, and wherein the optical fiber is further configured to deliver the collected light to the first electronic imaging device;
- (g) detecting visible light that is emitted from the area of interest in response to illumination by the first light source and generating a corresponding signal comprising visible light data, using a second electronic imaging device;
- (h) detecting near-infrared light having a first predetermined wavelength that is emitted from the area of interest in response to illumination by the second light source and generating a corresponding signal comprising a first set of near-infrared light data, using a third electronic imaging device;

(i) detecting near-infrared light having a second predetermined wavelength that is different from the first predetermined wavelength and that is emitted from the area of interest in response to illumination by the second light source and generating a corresponding signal comprising a second set of near-infrared light data, using a fourth electronic imaging device;

(j) generating at least one real-time integrated visual representation of the area of interest from the collected light data, visible light data, first set of near-infrared data, and second set of near-infrared data, using a controller in communication with each of the first electronic imaging device, second electronic imaging device, third electronic imaging device, and fourth electronic imaging device; and (k) displaying the at least one real-time integrated visual representation generated by the controller, for guidance during a diagnostic or therapeutic procedure, using a display in communication with the controller.

The present disclosure also provides for a computer-readable medium having stored thereon computer-executable instructions which can effect the disclosed method. For example, an additional aspect of this disclosure provides for a computer-readable medium having stored thereon computer-executable instructions which, when executed by a controller, cause a computer to perform the disclosed functions and operations for intra-operatively providing anatomical guidance in a surgical procedure.

EXAMPLES

Without intent to limit the scope of the disclosure, exemplary systems and methods and their related results according to the embodiments of the present disclosure are provided below. Note that titles or subtitles may be used in the examples for convenience of a reader, which in no way should limit the scope of this disclosure. Further, these examples are not intended to be inclusive of all aspects of the subject matter disclosed herein, but rather to illustrate representative methods and results. These examples are not intended to exclude equivalents and variations of the present disclosure which are apparent to one skilled in the art.

Example 1

Exemplary System and Handheld Spectroscopic Pen Device

This Example relates to the handheld spectroscopic pen device utilizing exogenous contrast agents for in vivo and intra-operative cancer detection. These principles are applicable when integrating the optical probe into an endoscopic device such as an endoscope, a colonoscope, a microscope, a surgical microscope, an arthroscope, a laparoscope, a thoracoscope, a mediastinan endoscope, a hysteroscope, a cyctoscope, a ureteroscope, a stereomicroscope, a colposcope, a fiber-optical system, or a rigid optical systems.

As provided in this example, the handheld spectroscopic pen device and near-infrared contrast agents are used for intra-operative detection of malignant tumors, based on wavelength-resolved measurements of fluorescence and surface-enhanced Raman scattering (SERS) signals. The handheld spectroscopic pen device utilizes a near-infrared diode laser (emitting at 785 nm) coupled to a compact head unit for light excitation and collection. This pen-shaped device removes silica Raman peaks from the fiber optics and attenuates the reflected excitation light, allowing for sensitive analysis of both fluorescence and Raman signals. Its overall performance has been evaluated by using a fluorescent contrast agent (indocyanine green, or "ICG") as well as an SERS contrast agent (pegylated colloidal gold). Under in vitro conditions, the detection limits are approximately $2\text{-}5\times10^{-11}$ M for the indocyanine dye and $0.5\text{-}1\times10^{-13}$ M for the SERS contrast agent. Ex vivo tissue penetration data show attenuated but resolvable fluorescence and Raman signals when the contrast agents are buried 5-10 mm deep in fresh animal tissues. In vivo studies using mice bearing bioluminescent 4T1 breast tumors further demonstrate that the tumor borders can be precisely detected preoperatively and intra-operatively, and that the contrast signals are strongly correlated with tumor bioluminescence. After surgery, the handheld spectroscopic pen device permits further evaluation of both positive and negative tumor margins around the surgical cavity, raising new potential for real-time tumor detection and image-guided surgery.

Previous work with fiberoptic devices for fluorescence and Raman measurements has not examined their suitability for measuring exogenous contrast agents during surgical procedures. In the present disclosure according to this Example, an integrated fiberoptic spectroscopic system is stably aligned and calibrated and is thus well suited for robust surgical use. One aspect of this design is that a rigid pen-sized fiber-optic unit can be used by a surgeon as a handheld device to detect small tumors and other lesions in real time during surgery. To address the issue of tumor heterogeneity, it is demonstrated that this spectroscopic system can be combined with injected contrast agents for intra-operative cancer detection and tumor margin delineation. As a result, much higher detection sensitivity and more consistent tumor signals are achieved than in previous studies that relied on native fluorescence or normal Raman scattering.

Reagents

Ultrapure water (18.2 MΩ) was used throughout the studies according to this Example. Indocyanine green (ICG), 3,3'-diethylthiatricarbocyanine iodide (DTTC), 2,2,2-tribromoethanol, tertiary amyl alcohol, and bovine serum albumin (BSA, 98%) were purchased from Sigma-Aldrich (St. Louis, Mo.). Citrate-stabilized gold colloids (60 nm diameter) at a concentration of $2.6\times10^{10}$ particles/mL were obtained from Ted Pella, Inc. (Redding, Calif.). Dulbecco's Modified Eagle's Medium (DMEM) (4.5 g/L glucose, 4.00 mM L-glutamine), fetal bovine serum (FBS), antibiotic/antimycotic solution, and phosphate buffered saline (PBS) were purchased from Thermo Scientific HyClone (Logan, Utah). XenoLight RediJect D-luciferin subtrate was purchased from Caliper Life Sciences (Hopkinton, Mass.). All reagents were used as purchased without further purification.

Handheld Spectroscopic Pen Device

A RamanProbe sampling head and connecting fiberoptics were purchased from InPhotonics (Norwood, Mass.). The cylindrical stainless steel sampling head (diameter 1.3 mm, length 10 cm) was integrated with a 5 m two-fiber cable, one for laser excitation and the other for light collection. The sampling head and fiber cable were coupled via an FC connector to a spectrometer designed by Delta Nu (Laramie, Wyo.). The combined sampling head and spectrometer system has a wavelength range of 800-930 nm with 0.6 nm spectral resolution for fluorescence measurement, and a Raman shift range of 200-2000 $cm^{-1}$ with 8 $cm^{-1}$ resolution for Raman measurement. Laser excitation was provided by a continuous-wave 200 mW diode laser emitting at 785 nm.

The handheld spectroscopic pen device was compared to a standard Raman spectrometer (Inspector, 785 nm excitation, 120 mW laser power, 0.6 nm resolution) (DeltaNu, Laramie, Wyo.) to check for wavenumber accuracy across the entire spectral range. A Raman scattering spectra from polystyrene was acquired over 5 s from both the handheld spectroscopic pen device and the commercial Raman spectrometer to determine the spectral accuracy of the handheld device. The sensitivity of the handheld spectroscopic pen device to detect ICG and SERS contrast agents was also determined. ICG was diluted in BSA solution to concentrations ranging from 25 nM to 50 pM. SERS nanoparticles were diluted in Milli-Q water to a concentration of 0.2-37.6 pM. Nanoparticle solutions of different concentrations were transferred (200 μL) into 96 well half-volume black microplates. The handheld spectroscopic pen device was fixed 10 mm above and centered over each well of the microplate. Signal collection times for each concentration ranged from 0.1 to 10 s. The relationship between the integrated signal intensity and the contrast agent concentration was statically analyzed with a linear regression model including calculated 95% confidence intervals. The statistical analyses were performed using Origin 6.1 software.

Nanoparticle Contrast Agents

Stock ICG solution was first dissolved in DMSO, and then diluted in aqueous solution containing the albumin protein (40 mg/mL, similar to the blood protein concentration). Under this condition, the ICG molecules quickly bound to albumin molecules, resulting in ICG-albumin complexes with a hydrodynamic size of 4-6 nm (diameter). The use of albumin also prevented ICG aggregation and fluorescence quenching. Spectrally encoded and PEG-stabilized SERS nanoparticles were prepared according to Qian, Nie, and coworkers. Briefly, aqueous diethylthiatricarbocyanine (DTTC) solution (4 μM) was added dropwise to a gold nanoparticle solution. The optimal SERS signals were detected when approximately $2\times10^4$ DTTC molecules were bound to each 60 nm gold particle. The particles were stabilized by the addition of a thiol-PEG solution (10 μM) and then purified by centrifugation.

Tissue Penetration Depth Measurement

Porcine tissues used for ex vivo studies were obtained from the Animal and Dairy Science Department at the University of Georgia (Athens, Ga.). Fluorescence and Raman spectra of porcine fat, liver, and lung were collected over 5-10 s. These tissues were chosen for both their relevance to disease processes and for their optical properties. To determine the depth at which the handheld spectroscopic pen device can detect fluorescent dyes or SERS nanoparticles in various organs, an 8 mm$^3$ section of the tissue was loaded with 20 μL, of either 650 nM ICG or 300 pM SERS nanoparticle solution. Next, thinly sliced sections of the corresponding tissues were laid on top of the contrast agent-loaded specimen. After each tissue section was applied, fluorescent or Raman spectra were collected over 0.1-10 s with the handheld spectroscopic pen device. A distance of 1 cm was maintained between the handheld spectroscopic pen device tip and the top tissue layer, in order to simulate the handheld spectroscopic pen device position during surgical use. A layer of plastic wrap was placed in between the contrast agent loaded tissue and subsequent tissue layers to prevent diffusion of contrast agents into the unlabeled tissue slices. Spectra were scaled as needed or desired to correct for different integration times and then integrated to obtain the reported signal intensity.

In Vivo and Intra-Operative Measurements

All in vivo murine studies were performed under an approved protocol by the Emory University IACUC. The mouse mammary carcinoma cell line 4T1, which stably expresses a firefly luciferase gene, was obtained from Dr. Lily Yang at Emory University (Atlanta, Ga.). 4T1 cells were cultured in DMEM containing 10% FBS and 1× antibiotic/antimycotic agent. Prior to injection into mice, the cells were washed two times with PBS and diluted in sterile PBS to a final concentration of $2\times10^7$ cells/mL. Mammary tumors were inoculated into nude mice by the subcutaneous administration of $2\times10^6$ 4T1 cells into the mouse flank. Once the tumors were approximately 4 mm in diameter, ICG was administered intravenously (i.v.) via a tail vein at a dose of 357 μg/kg. After 24 h, mice were anesthetized by intraperitoneal (i.p.) injection of a 2.5% solution of tribromoethanol (350 mg/kg). Tumor-bearing mice undergoing bioluminescence imaging were administered i.p. 100 μL, of a luciferin solution (30 mg/mL). Bioluminescent images were acquired on a Kodak In-Vivo FX Imaging System from Carestream Molecular Imaging (Rochester, N.Y.). Corresponding bright-field images were taken for anatomical reference of the bioluminescence signal. A series of spectra were acquired on tumor-bearing mice using the handheld spectroscopic pen device. First, the position of the handheld spectroscopic pen device was fixed to about 1-2 cm above the location of the acquisition area on the mouse. Spectra were collected in 1 s and were obtained from several locations, including directly over the center of the tumor and the peritumoral region. After the spectra were acquired, the integrated signal intensity was calculated. The signal intensity was compared to both the bright-field anatomical location and the bioluminescence signal.

Handheld Spectroscopic Pen Device Design and Performance.

Figure 3:
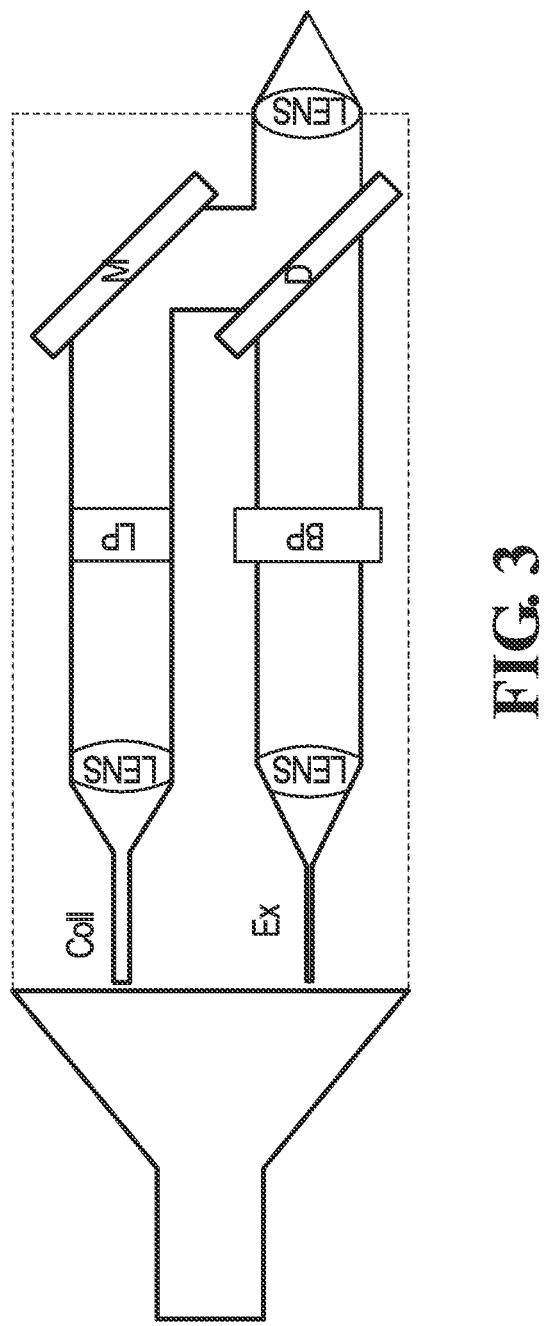
FIG. 3 schematically shows optical beam paths of an optical device such as the handheld spectroscopic pen device in operation, according to one embodiment of the present invention.
Figure 4:
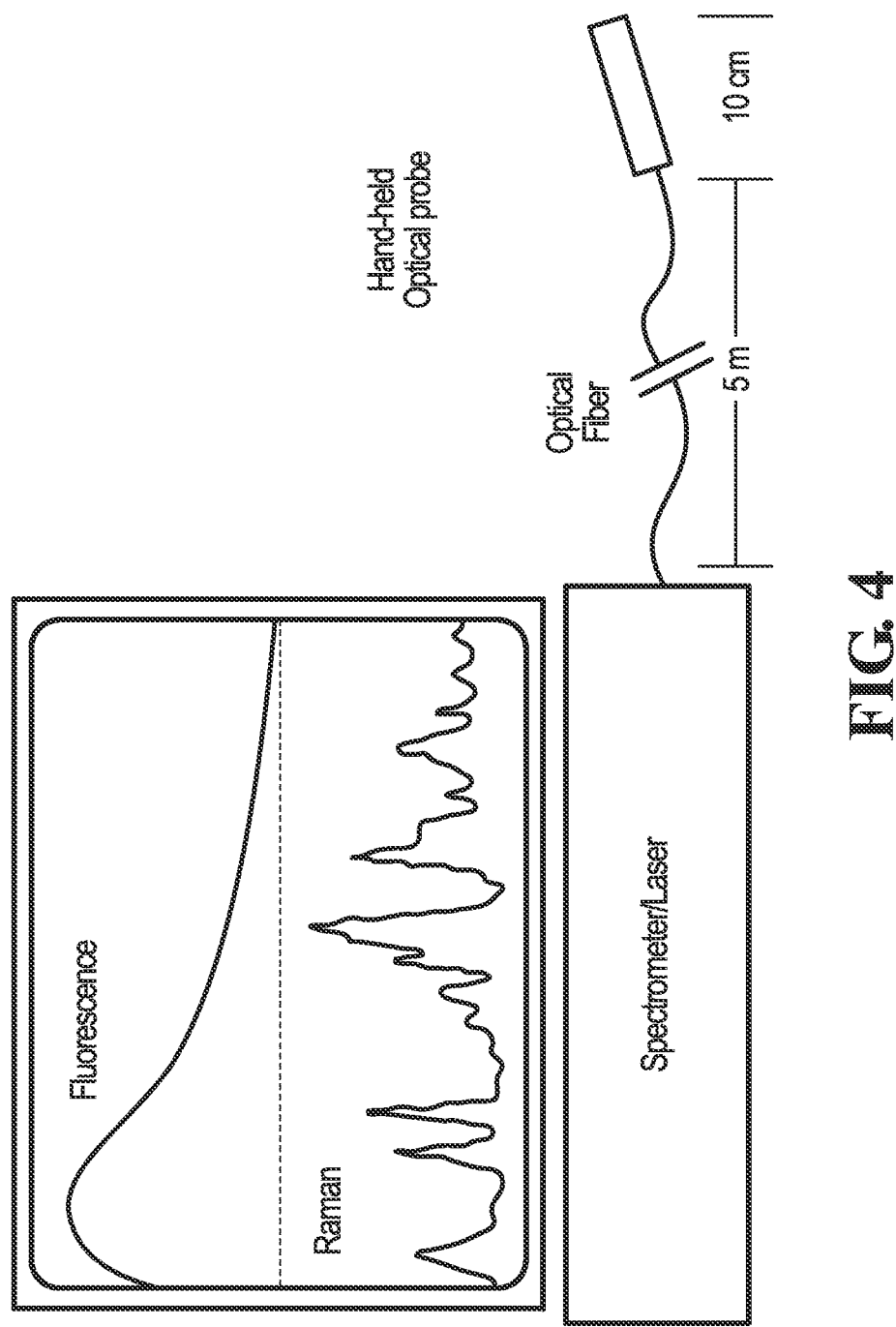
FIG. 4 schematically shows a system for wavelength-resolved fluorescence and Raman measurements, according to one embodiment of the present disclosure.
Figure 5:
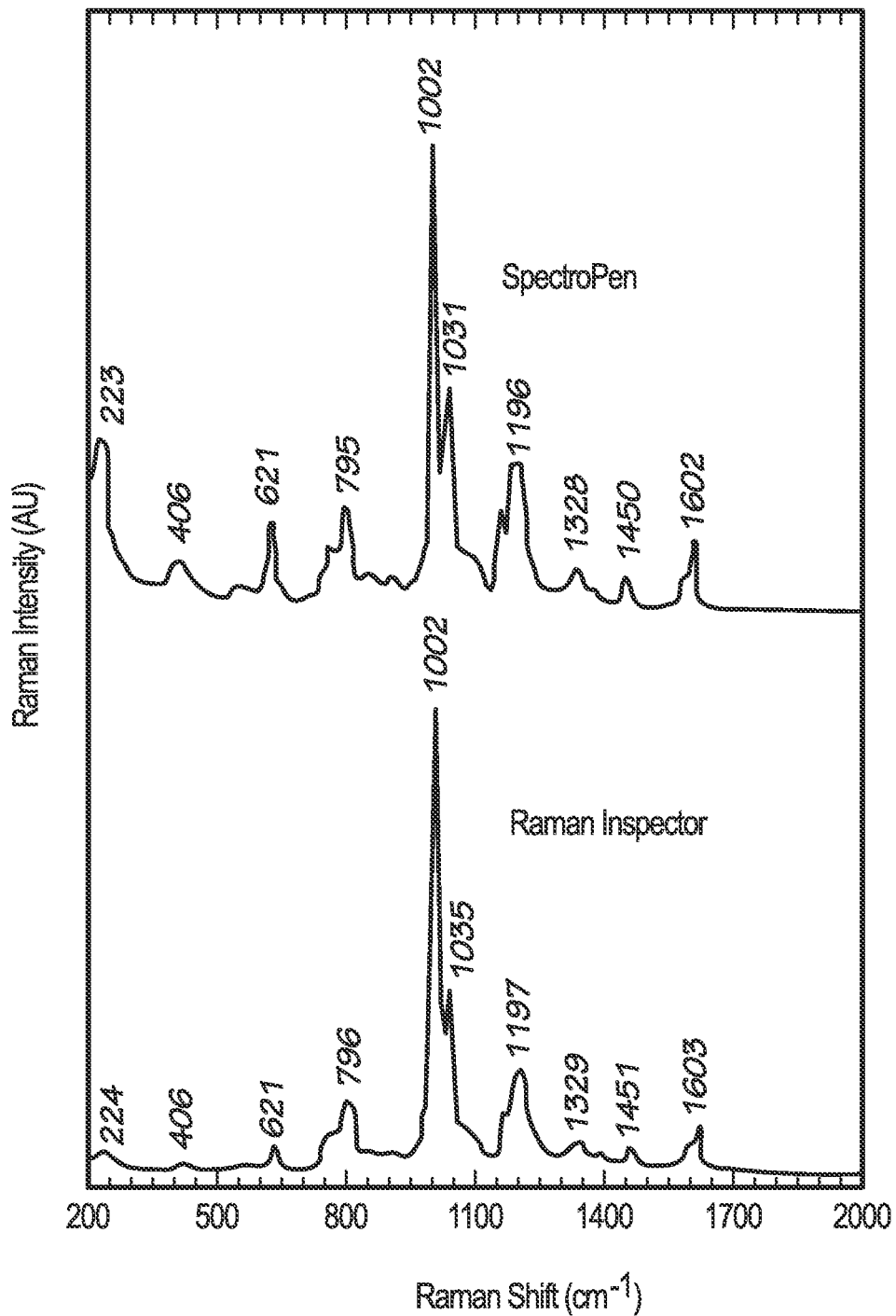
FIG. 5 illustrates Raman spectra obtained for a standard sample (polystyrene), according to one embodiment of the present disclosure.

The handheld spectroscopic pen device connects a handheld sampling head, via a fiberoptic cable, to a spectrometer that can record fluorescence and Raman signals. The ability to resolve NIR fluorescent and Raman signals from background tissue arises from the optical filtering that takes place in the handheld portion of the device, as illustrated in FIGS. 3 and 4. FIG. 3 schematically shows optical beam paths of a handheld spectroscopic pen device, with excitation light provided from a 785 nm laser diode (200 mW output), and having an excitation fiber ("Ex"), collection fiber ("Coll."), band-pass filter ("BP"), long pass filter ("LP"), dichroic filter ("D"), and reflective mirror ("M"). As shown, the laser light is transmitted through the excitation fiber into the pen. A first lens collimates the excitation light. Wavelength selectivity is provided by a band-pass filter. Excitation light is then focused onto the sample of interest. Backscattered light is collected through the same lens. A dichroic mirror and a long pass filter attenuate Rayleigh scattering by a factor of $10^8$ in the collection fiber. Thus, only Stokes-shifted light is transmitted to the spectrometer. Silica Raman bands arising from the optical fibers are attenuated by physical filtering in both the excitation and emission optical paths. The device's overall performance was evaluated by comparing the polystyrene Raman spectra obtained with the handheld spectroscopic pen device and a standard Raman spectrometer (see FIG. 5). The results show well matched Raman signals between the two spectrometers and also with the literature spectra of polystyrene. The differences in peak positions (wavenumbers) are less than 0.5% across the entire range of 200-2000 cm$^{-1}$.

Detection Sensitivity and Dynamic Range

Figure 6A:
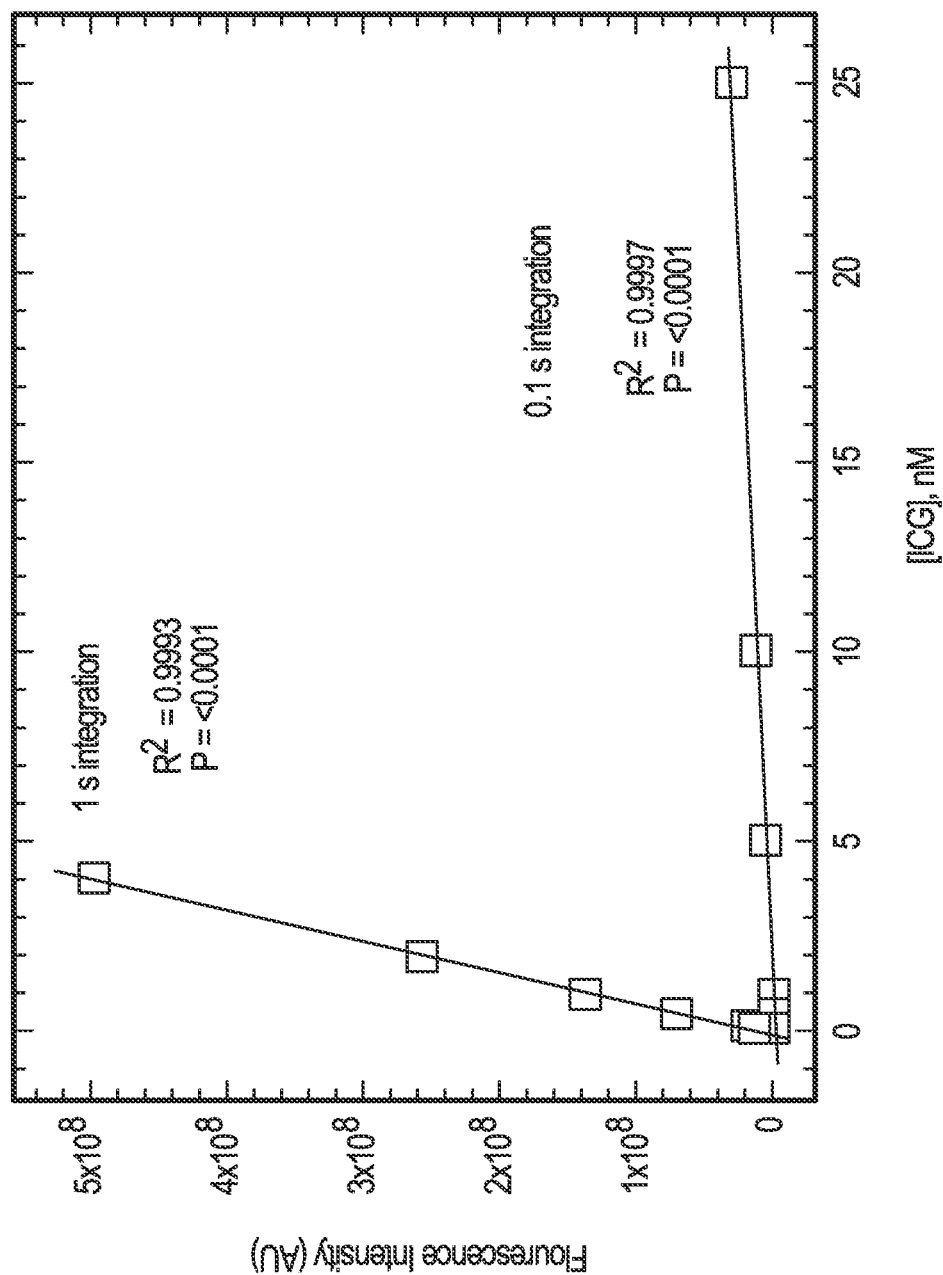
FIG. 6A illustrates fluorescence spectra obtained for various concentrations of contrast agents, according to one embodiment of the present disclosure.
Figure 6B:
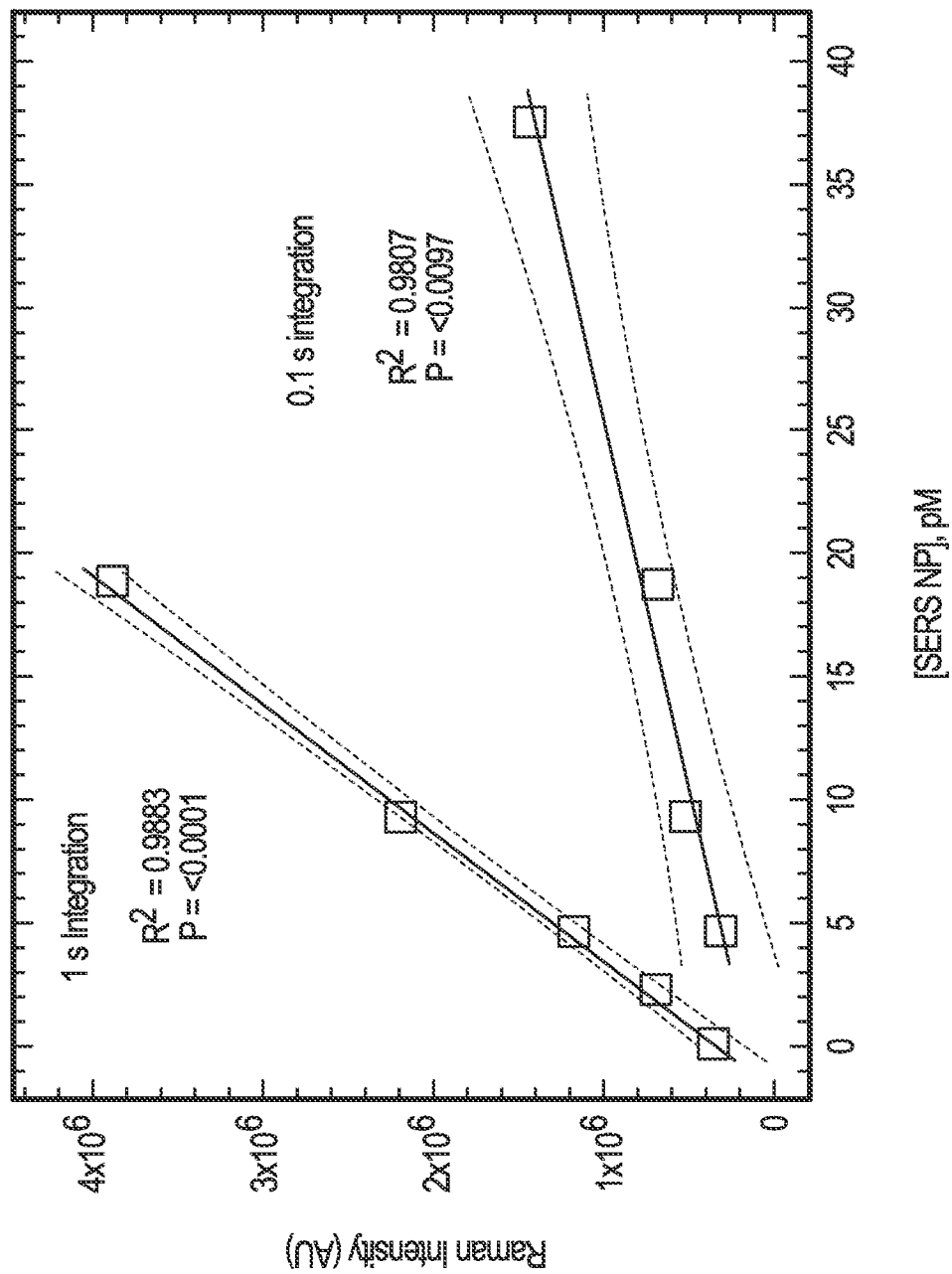
FIG. 6B illustrates Raman spectra obtained for various concentrations of contrast agents, according to one embodiment of the present disclosure.

As depicted in FIG. 4, the handheld spectroscopic pen device allows for sensitive detection of both fluorescent and SERS contrast agents. A linear relationship is found between the recorded signal intensity and contrast agent concentration. FIGS. 6A and 6B show the linear regression model fit to the integrated intensity versus concentration curves. The linear regression model is shown as a blue line with 95% confidence intervals shown as dashed red lines. $R^2$ is the fit coefficient of the linear regression model, and has a value of 1 for perfect fits. The P-values indicate that the slopes of the linear regression are significantly different than zero. Further examination shows a narrow 95% CI band (red dashed lines) indicating that the regression fit is very close to the "true" fit for both ICG and SERS contrast agents. The minimum spectrally resolvable concentrations (that is, limits of detection) are $2$-$5 \times 10^{-11}$ M for ICG and $0.5$-$1 \times 10^{-13}$ M for the SERS agent. The Raman reporter dye (diethylthiatricarbocyanine) used here is in resonance with the excitation wavelength at 785 nm, so the phenomenon should be called surface-enhanced resonance Raman scattering (SERRS). Also, the SERRS nanoparticles are 40-50 fold more sensitive than ICG under the above-mentioned experimental conditions, primarily because of the poor optical properties of ICG (less than 2% quantum yield and fluorescence quenching induced by aggregation). The maximum detectable concentration is determined by detector signal saturation, the analog-to-digital converter (16 bits, $2^{16}$=65,536), and the data integration time. That is, for low contrast signals, the integration time should be increased in order to improve the signal-to-noise ratio, whereas for high contrast signals, the integration time should be reduced to avoid detector saturation (which will allow high-speed acquisition of tumor contrast signals). The dynamic range is then defined by the low and high limits in which the contrast signal intensity is linear with its concentration. For both fluorescence and Raman measurements, the handheld spectroscopic pen device provides a 50-60 fold dynamic range. Accordingly, weak tumor-margin signals that are 50-60 fold lower than the central tumor signals can be measured simultaneously without adjusting the data acquisition parameters, as further discussed below.

Spectral Discrimination and Tissue Penetration Depth

An objective of intra-operative use of the handheld spectroscopic pen device is detection of tumor foci at the margins of the tumor mass, thereby minimizing the risk of positive margins. In practice, a real-time detection system according to aspects of the exemplary embodiment disclosed in this Example allows the surgeon to remove tumor tissue that might have gone undetected, saving the patient from repeated surgery and potentially improving survival. Sensitive tumor detection is based on the use of albumin-bound ICG or SERS nanoparticles as contrast agents. As discussed in more detail later, the main mechanism is believed to be "passive tumor targeting" in which nanoparticles are accumulated and retained in the tumor interstitial space mainly through the enhanced permeability and retention (EPR) effect.

The ability of the handheld spectroscopic pen device to differentiate contrast agent signals from the autofluorescence and Raman scattering of major tissue/organ types (i.e. fat, liver and lung) was first examined. FIG. 4 shows representative spectra of pure ICG, animal fat, and a mixture of ICG and animal fat (ICG in fat). At 785 nm excitation, ICG has a fluorescence peak at 816 nm, while fat has a background fluorescence peak at 805 nm plus resolvable Raman signals at 862, 1070, 1297, 1439, and 1652 $cm^{-1}$ (corresponding to 842, 857, 874, 885, and 902 nm in wavelength, respectively). ICG buried in fat has identifiable contributions of both ICG and fat (e.g., ICG fluorescence at 816 nm and the fat Raman peaks at 874 and 885 nm).

Figure 7A:
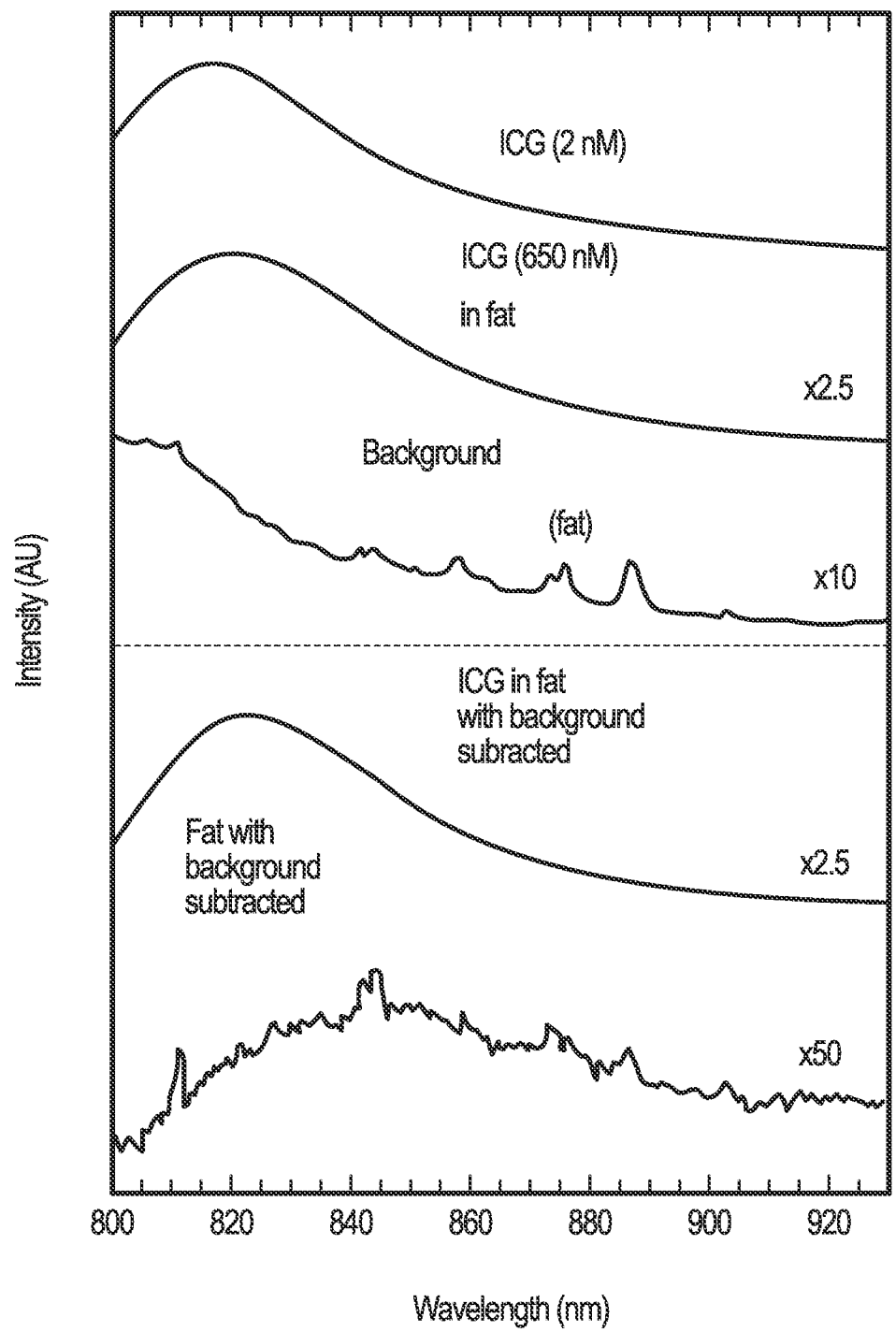
FIG. 7A illustrates fluorescence spectra obtained before background signal subtraction (upper panel) and after background signal subtraction (lower panel), according to one embodiment of the present disclosure.
Figure 7B:
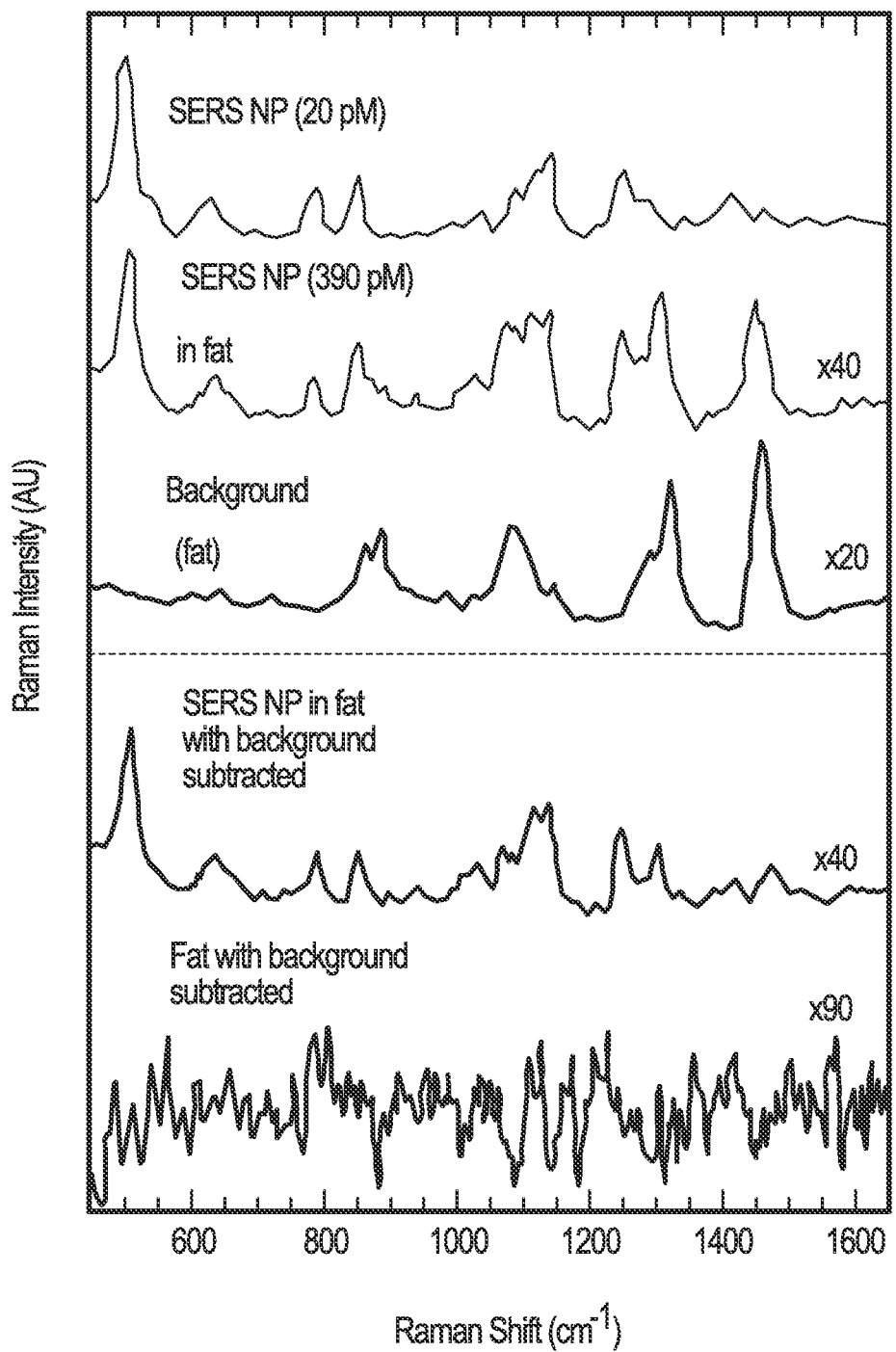
FIG. 7B illustrates Raman spectra obtained before background signal subtraction (upper panel) and after background signal subtraction (lower panel), according to one embodiment of the present disclosure.

FIG. 7A illustrates fluorescence spectra of pure ICG, animal fat, and a mixture of ICG and animal fat before background subtraction (upper panel) and after background subtraction (lower panel). FIG. 7B illustrates Raman spectra of pure SERS nanoparticles, animal fat, and a mixture of SERS nanoparticles and animal fat before background subtraction (upper panel) and after background subtraction (lower panel). All spectra were taken with the handheld spectroscopic pen device positioned 1 cm above the top layer of tissue. Spectra were acquired over 0.1-10 s. The background was obtained by averaging four different spectra obtained from control tissues, and was subtracted from the contrast-enhanced spectra or from single background measurements. Signal intensities relative to that of pure ICG or SERS samples are indicated by scaling factors. The Raman reporter dye was diethylthiatricarbocyanine (DTTC).

Figure 8:
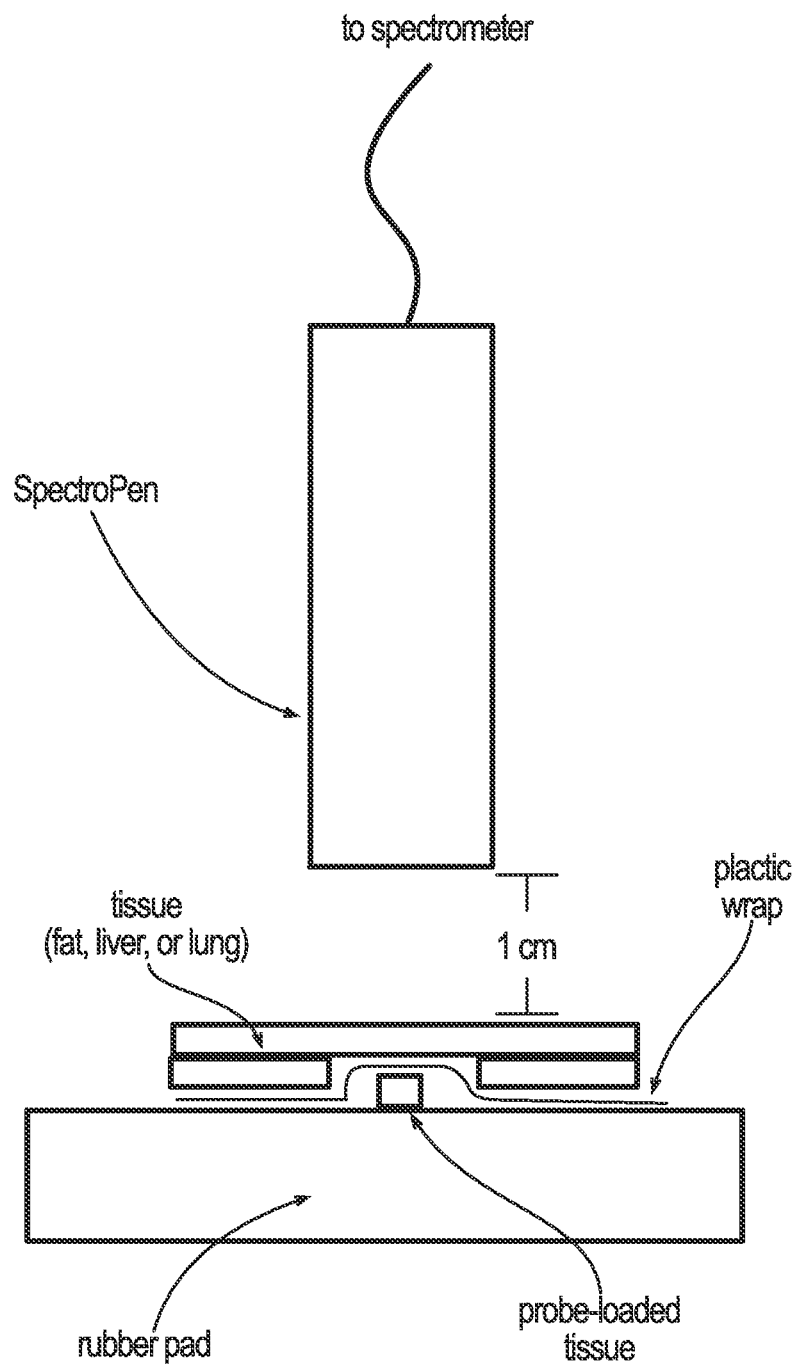
FIG. 8 schematically shows a system for performing tissue penetration depth studies of near-infrared fluorescent and SERS contrast agents, according to one embodiment of the present disclosure.

As shown in FIG. 7A (lower panel), the background signal of fat can be accurately subtracted, allowing nearly pure ICG contrast signals. Similarly, the data in FIG. 7B (upper and lower panels) show that the background Raman spectrum can be subtracted to reveal predominantly the SERS contrast signals. As noted, the ability to detect deeper satellite residual tumors adjacent to the primary tumor can be important for complete tumor resection and improving patient outcome. To simulate this surgical scenario, the ability of the handheld spectroscopic pen device to detect optical contrast agents below the surface of fat, liver, and lung tissues was examined, by placing contrast agent loaded tissue specimens below 1-2 mm sections of unlabeled tissue (FIG. 8). FIG. 8 schematically shows a system for performing tissue penetration depth studies of near-infrared fluorescent and SERS contrast agents.

Figure 9A:
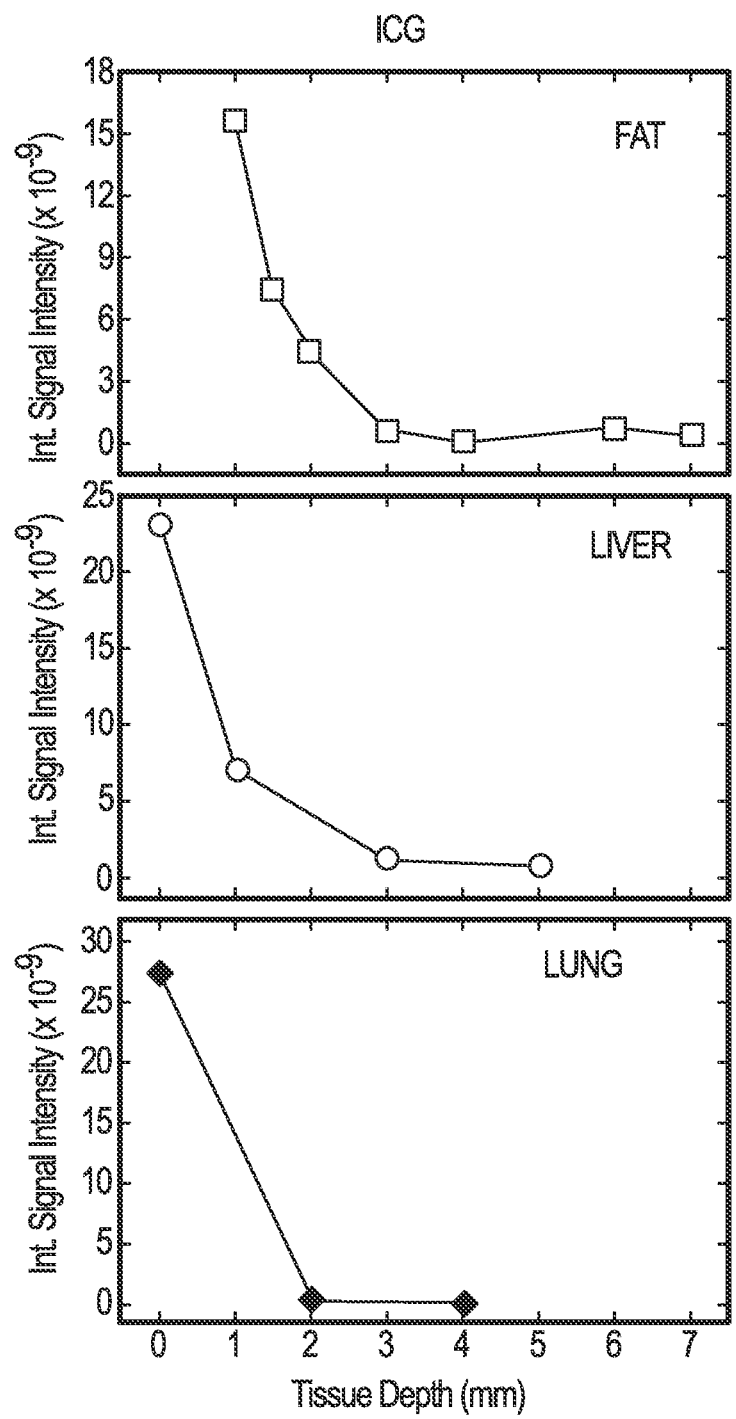
FIG. 9A illustrates indocyanine green (ICG) signals as a function of placement depth of contrast agents in fresh fat, liver, and lung tissue, according to one embodiment of the present disclosure.
Figure 9B:
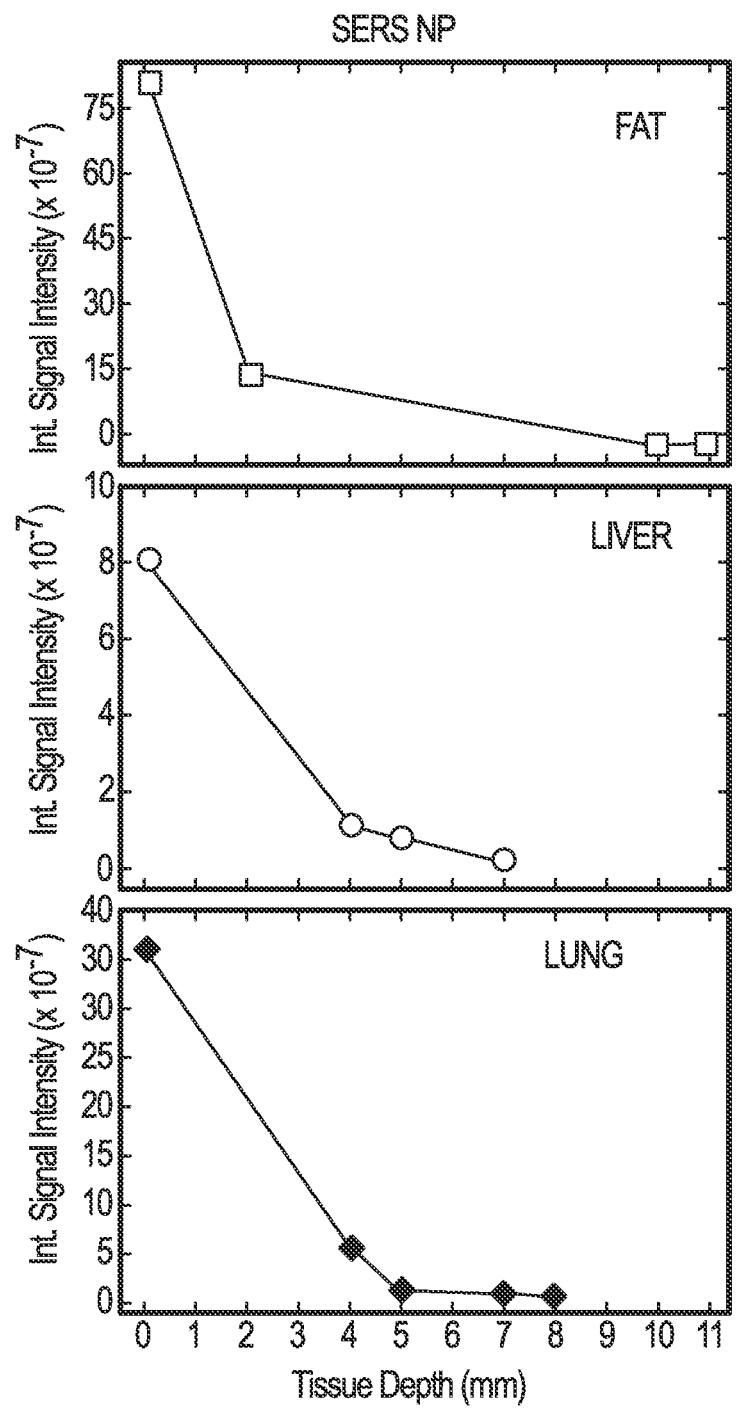
FIG. 9B illustrates SERS signals as a function of placement depth of contrast agents in fresh fat, liver, and lung tissue, according to one embodiment of the present disclosure.

FIGS. 9A and 9B show the relationship between signal intensity and the depth of ICG or SERS agents deeply placed in ex vivo tissues. As suggested from light scattering, the contrast signal intensity decreased almost exponentially with tissue thickness. ICG can be detected more deeply in fat than other tissues because fat does not scatter the excitation light as strongly as lung and liver. This finding has potentially pertinent applications in lipomatous (fat-rich) tissues such as breast and some other soft tissues. In addition, lung and liver have more intense autofluorescence with NIR excitation (likely due to porphyrins and related chromophores in these highly vascularized organs), which compromises the ability to distinguish ICG emission from native autofluorescence. In comparison, SERS nanoparticles give rise to sharp spectral peaks that are distinct from the broad background, allowing accurate extraction of weak SERS signals under high-attenuation and scattering conditions. Thus, weaker SERS signals can be detected and resolved at a greater tissue depth in comparison with ICG fluorescence. The penetration depth can be further improved by positioning the fiberoptic tip closer to the tissue surface (almost in contact).

In Vivo and Intra-Operative Tumor Detection

Figure 10A:
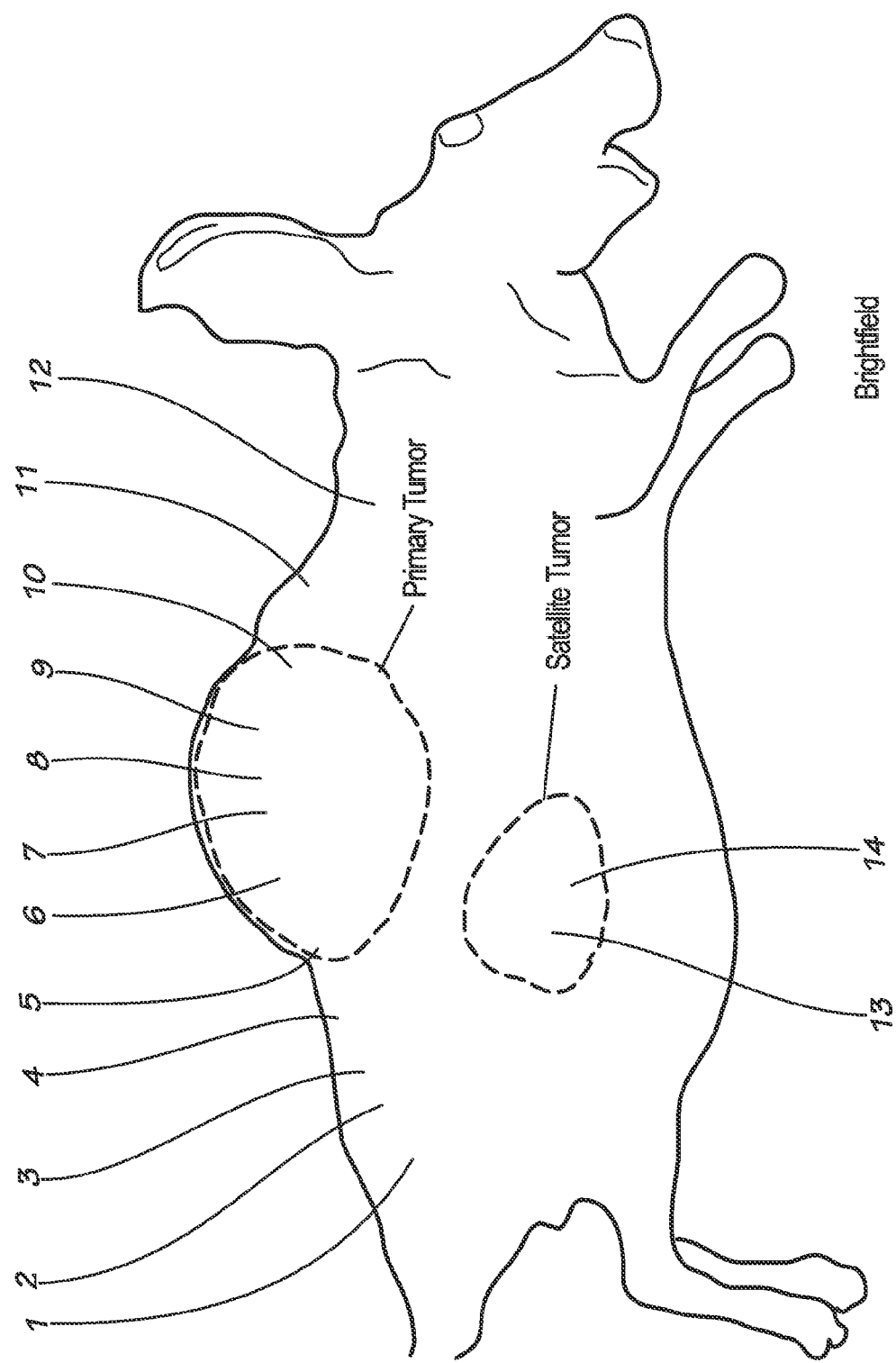
FIG. 10A shows a bright-field image identifying anatomical locations of a primary tumor and two satellite nodules (dashed circles), according to one embodiment of the present disclosure.
Figure 10B:
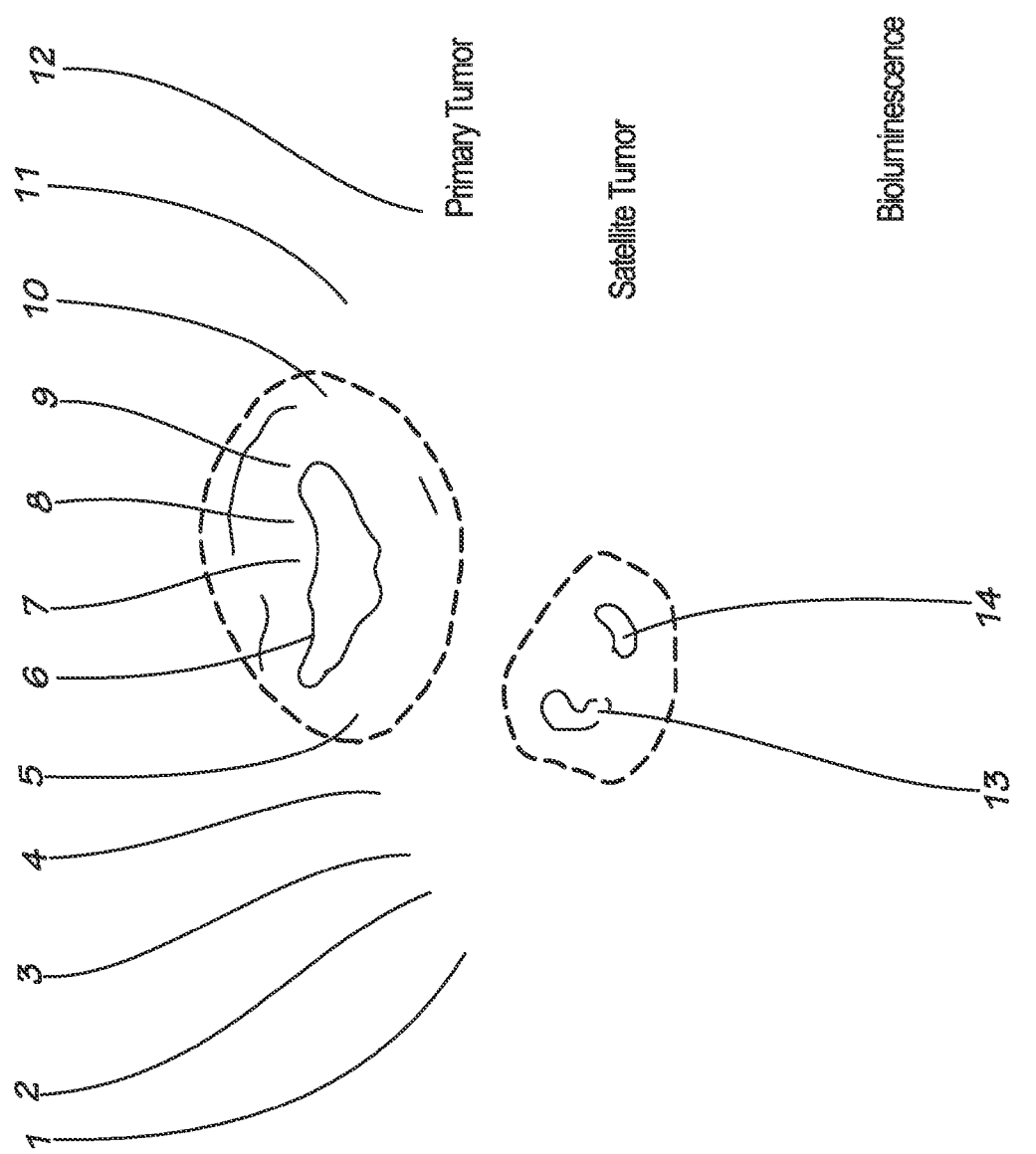
FIG. 10B shows a bioluminescence image of a mouse, identifying the primary and satellite tumors (red signals), according to one embodiment of the present disclosure.

In vivo investigations were conducted to test the ability of the handheld spectroscopic pen device to detect intratumoral deposition of ICG after intravenous infusion. This contrast agent has been approved by the U.S. Food and Drug Administration (FDA) and is indicated for various uses in humans, such as for determining cardiac output, hepatic function and liver blood flow, and for ophthalmic angiography. To assess degree of tumor contrast enhancement using ICG, mice were used in which 4T1 tumor cells ($2 \times 10^6$ in number) were subcutaneously injected 18 days prior to imaging. The tumor cells were genetically engineered to express the firefly luciferase gene; intravenous injection of luciferin after tumor development causes these cells to emit bioluminescent light and allows one to determine the precise location of tumors using bioluminescence imaging. Thus, ICG contrast enhancement can be correlated with simultaneous bioluminescence imaging to determine whether ICG contrast enhancement (if any) originated from tumor sites. On day 17 after tumor cell inoculation, ICG was intravenously infused into the mice using a dose of 357 µg/kg, which is the equivalent dose used for human use, and then imaged the mice using the handheld spectroscopic pen device 24 h later. Using bioluminescence imaging, a dominant tumor site was identified, along with two satellite tumor sites along the track of the needle used for inoculation of tumor cells (FIGS. 10A and 10B). A set of 14 spectra was obtained from the mouse using the handheld spectroscopic pen device.

Specifically, FIG. 10A shows a bright-field image identifying the anatomical locations of a primary 4T1 breast tumor and two satellite nodules (dashed circles). The specific locations for measurement using a handheld spectroscopic pen device are indicated by numbers 1-12 for the primary tumor and 13-14 for the satellite nodules. FIG. 10B shows a bioluminescence image of the mouse, identifying the primary and satellite tumors (red signals).

Figure 11:
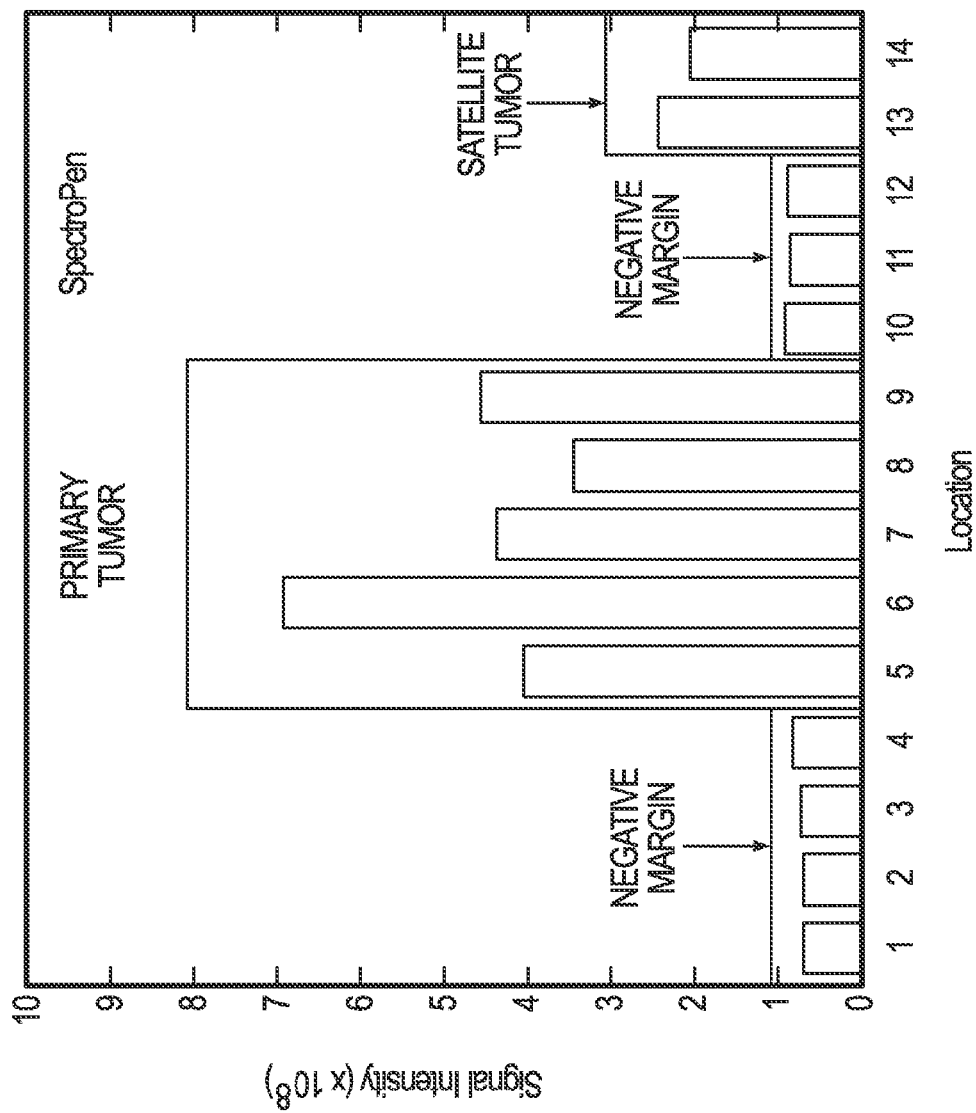
FIG. 11 illustrates indocyanine green (ICG) signal intensities detected at various locations identified in FIGS. 10A and 10B.

FIG. 11 highlights the high degree of ICG contrast enhancement in the tumors as compared to the surrounding tissues. The intense ICG signals at locations 5-9, 13, and 14 are indeed correlated with the presence of tumor as determined by bioluminescence. The integrated signal intensities from the tumor areas are nearly 10 times more intense than the signals obtained from normal regions. Spectra collected from the adjacent edges (less than 2 mm from the tumor) are still 5-6 times stronger than that of the more remote areas, providing excellent delineation of the tumor. After surgical removal of the tumors, bioluminescence imaging shows that the excised tumors are bright and the surgical cavity is dark (see FIGS. 12A and 12B).

Figure 12A:
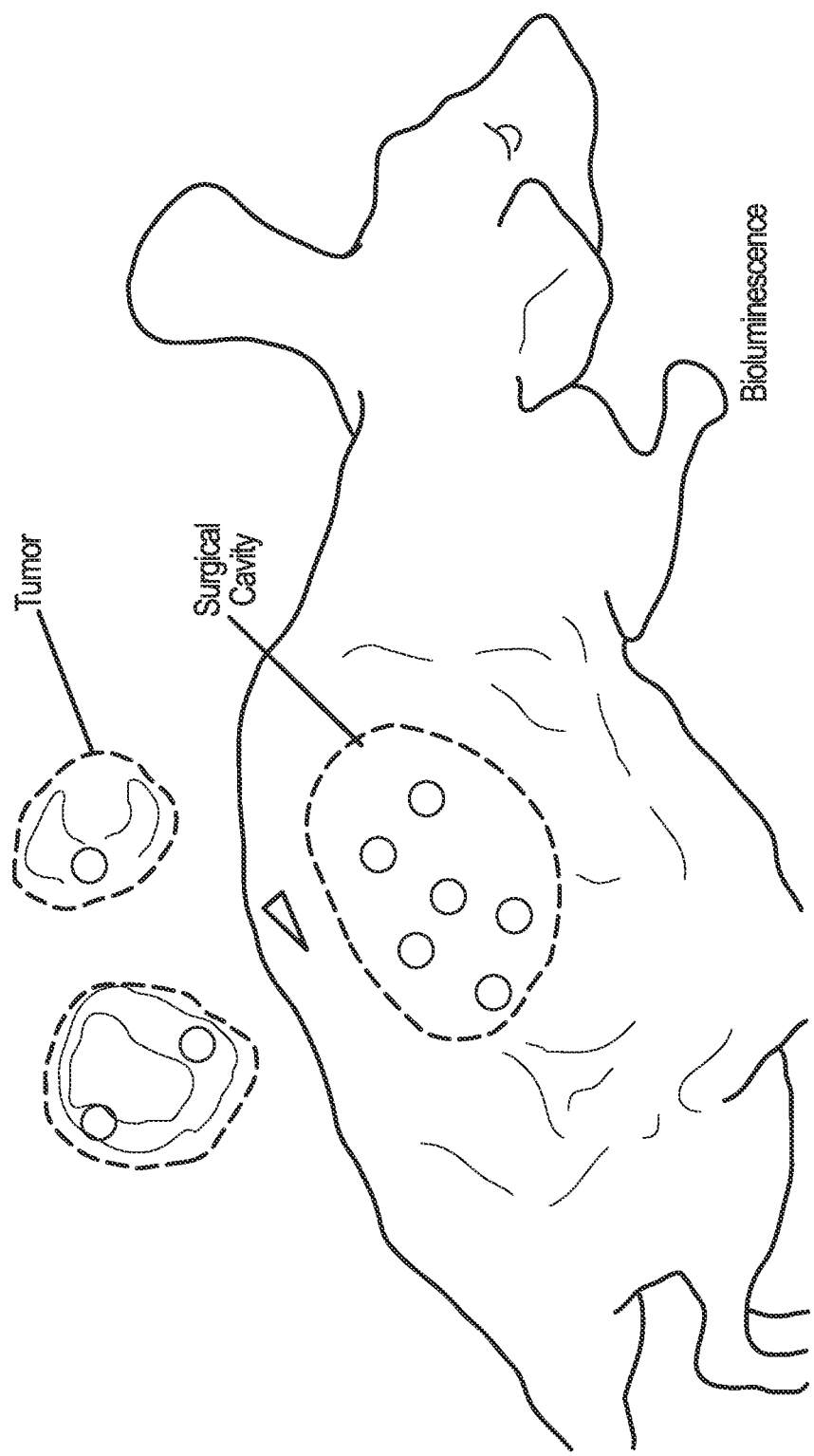
FIG. 12A shows a bright-field image identifying a resected tumor (yellow dashed lines) and surgical cavity (cyan dashed line), obtained by detection of positive and negative tumor margins, with a region having a residual tumor along the margin of the cavity, as detected by its signal intensity, according to one embodiment of the present disclosure.
Figure 12B:
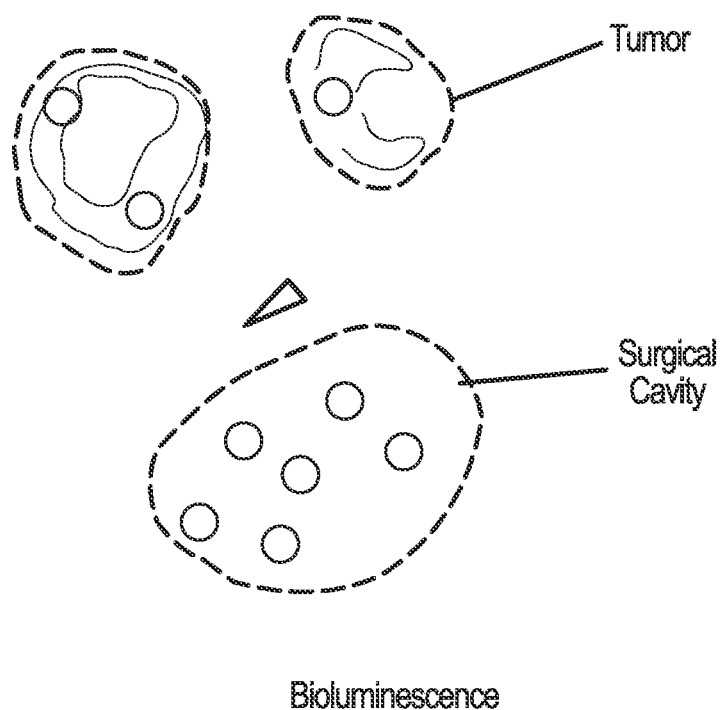
FIG. 12B shows a bioluminescent image identifying a resected tumor (yellow dashed lines) and the surgical cavity (cyan dashed line), where spectra obtained within the excised tumor are shown in red, those in the surgical cavity are shown in cyan, and one on the margin of the surgical cavity is shown by a white arrowhead, according to one embodiment of the present disclosure.

Specifically, FIGS. 12A and 12B show bright-field images (FIG. 12A) and bioluminescent images identifying positive and negative tumor margins detected using a handheld spectrometer pen device, including a resected tumor (yellow dashed lines) and the surgical cavity (cyan dashed line). Spectra obtained within the excised tumor are shown in red, those in the surgical cavity are shown in cyan, and one on the margin of the surgical cavity is shown by a white arrowhead. As seen on the bioluminescence image, there was a region with residual tumor along the margin of the cavity.

Figure 13:
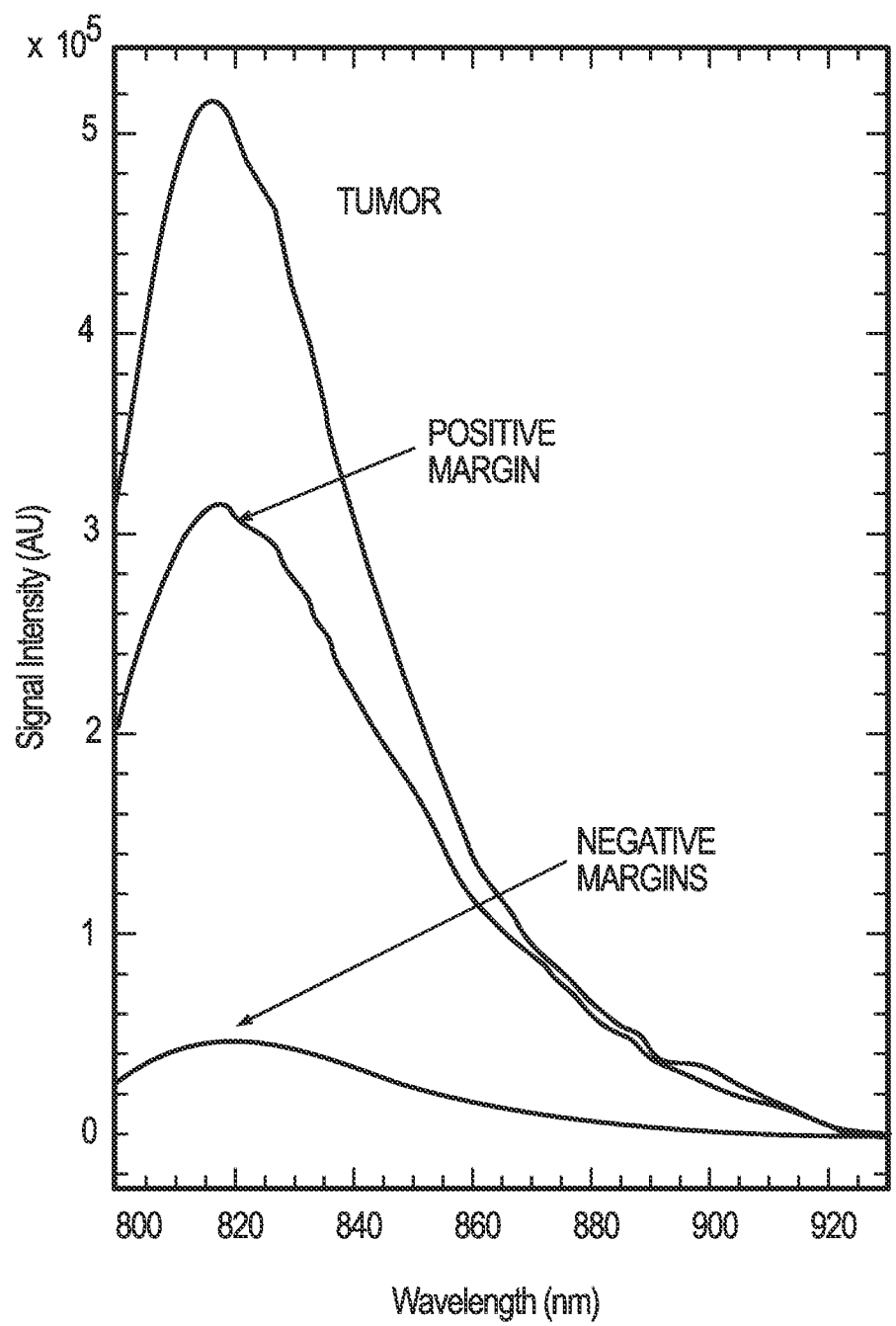
FIG. 13 illustrates averaged spectra from tumors and positive and negative margins, according to one embodiment of the present disclosure.

Referring to FIG. 13, spectra recorded by the handheld spectroscopic pen device indicate 10-fold stronger signals for the excised tumors as compared to the cavity, which is consistent with the contrast ratio of tumor to healthy tissue found within the living animal (see FIG. 11).

There was a very small area of bioluminescence remaining at the margin of the cavity, corresponding to a positive surgical margin, that was not seen by visual inspection alone. Reexamination of this area with the handheld spectroscopic pen device revealed an ICG signal that was 5 times stronger than for adjacent tissue, again consistent with the contrast ratios recorded from noninvasive imaging. The ability to obtain a strong ICG signal from tumor, remove the tumor as guided by the handheld spectroscopic pen device, and obtain real-time pathology about the margin status of both excised tissue and the remaining tumor cavity, all constitute useful features for image-guided surgery.

Results indicate that the observed ICG contrast between tumor and normal tissues is very clear and strong, even though no tumor-targeting ligands are used in this work. Previous oncology studies utilizing ICG are mainly directed toward sentinel lymph node detection. These studies rely on direct intratumoral or peritumoral injections of ICG rather than the intravenous route of administration as used in the study according to the present Example. After intravenous administration, ICG is known to bind to the hydrophobic pockets of serum proteins, especially albumin and lipoproteins. Thus, through protein binding, ICG takes on nanometer scale dimensions, with a hydrodynamic size of 6-8 nm diameter. The strong tumor enhancement comes from the enhanced permeability and retention (EPR) effect, in which macromolecules or nanoparticles preferentially accumulate in tumor due to the abnormal neovasculature with large fenestrations and poor lymphatic drainage characteristic of tumors. More advanced nanoparticle formulations of ICG have been reported to facilitate longer circulation of ICG and increased tumor accumulation for diagnostic and photothermal applications. Also, targeted contrast agents can be developed by conjugating SERS and other nanoparticles to peptides, monoclonal antibodies, and small-molecule ligands for molecular recognition of antigens or receptors on the surface of tumor cells.

In summary, according to this Example, a handheld spectroscopic device was constructed and the use of two near-infrared contrast agents for in vivo and intra-operative tumor detection has been shown. Under in vitro conditions, the handheld device provides a detection limit of $2\text{-}5\times10^{-11}$ M for ICG and a detection limit of $0.5\text{-}1\times10^{-13}$ M for SERS. The tissue penetration depth is about 5-10 mm depending on the tissue's optical properties and the ability to resolve weak contrast signals. In addition, in vivo studies were carried out by using mouse models bearing bioluminescent 4T1 breast tumors. The results indicate that the tumor borders can be precisely detected preoperatively and intra-operatively, resulting in real-time detection of both positive and negative tumor margins around the surgical cavity. In comparing the two types of near-infrared contrast agents, SERS nanoparticles (60-80 nm) provide rich spectroscopic information (sharp spectral features), but are much larger than the ICG-albumin complexes (4-6 nm). Accordingly, the SERS agent may be better suited for mapping blood vessels and tumor boundaries/peripheries (for delineating tumor margins), whereas ICG-albumin may be better suited for tumor penetration and rapid clearance.

Example 2

Exemplary Integrated Imaging and Spectroscopy System

This Example relates to an integrated imaging and spectroscopy system for image-guided surgery. According to one embodiment, the system is configured to detect the signal from a fluorescent or Raman-active probe introduced into a patient and localized to a disease area of interest (e.g. a tumor). A surgeon using this system may totally remove a diseased area and verify that the diseased area was successfully and entirely removed.

According to one embodiment of the present Example, a multi-modal imaging system comprises a wide-area imaging system that is configured for imaging in the visible and near-infrared light ranges (400-1000 nm), and a narrow-beam combination fiberoptic laser light excitation source (633 nm or 785 nm) and spectroscopy detector. The wide-area imaging system has one lens and three cameras: one color camera to detect and record visible light (400-610 nm, what a user sees with the unaided eye); one black and white camera to detect the light from the laser excitation source (633 nm or 785 nm); and one black and white camera to detect the light emitted from a probe (e.g. 850 nm). Physical optical filters (bandpass for emission selectivity, laser line/notch to block laser excitation light on all but the "laser camera," and dichroic mirrors to split the desired light among the three cameras) are used to split the light collected from a single lens into the three individual cameras and to provide specificity for the desired wavelengths of light to reach each camera. The system is used alongside fluorescent (e.g. indocyanine green dye, quantum dot) or surface-enhanced Raman scattering (SERS) probes injected into the subject and accumulated by passive or active targeting to an area corresponding with diseased tissue. When in use, the information from the cameras is processed by a computer and displayed such that the user may see the visual field; an overlay onto the image of the visual field shows the position of the laser illumination and the light illumination of the probe (if present). A computer uses image processing to enhance the image of the visual field, making it easier to distinguish the position of the probe in relation to the surrounding tissue. Simultaneously, the fiber-optic laser illumination and spectroscopy detector displays a spectrum of the light emitted from the area illuminated by the laser light. The spectroscopy system is operative to detect the fluorescence emission and Raman light scattering of both native tissue and the introduced probes.

Example 3

Exemplary Method for Condensing Spectrograph Information

This example relates to a method for condensing spectrograph information recorded by a "Raman pen" spectrometer onto a wide-field video display (see also the system according to Example 2, above), also referred to as "virtual phosphorescence". According to one embodiment, the virtual phosphorescence display mode is a way to overlay information recorded continuously from a Raman pen spectrometer onto a wide-field image. Data recorded from the spectrometer is a spectrum (the intensity of light at a given wavelength). For fluorescence probes, data is analyzed in a simple area-under-the-curve (AUC) method (ratio of integrated fluorescence to minimum/background); for Raman scattering probes (and optionally for fluorescence probes), a computationally more complex deconvolution method is used (match known spectra to the recorded spectra via optimization). A positive signal is assumed when the fluorescence AUC ratio is over a predetermined threshold or when the AUC ratio of the spectra obtained through deconvolution are over a predetermined threshold. In both cases, the predetermined threshold is at least 3 standard deviations above the background signal level, and corresponds to a significant amount of fluorescent or Raman probe in the sample area of the spectrometer.

When a positive signal is recorded, a false color overlay is placed on the wide-field image at the location of a laser excitation source when the signal was recorded (the location is detected by the camera dedicated for laser tracking) the overlay decays over time. That is, initially the overlay will be bright, but over the course of seconds the overlay will become progressively more translucent (and so appear dimmer). The decay time is user-selectable, so for very static conditions, such as when the surgical area is being swept by the Raman pen to locate tumor boundaries, a longer decay time (e.g. 5 seconds) is used to indicate where positive signals are recorded. For dynamic conditions, such as when a surgeon is actively cutting tissue under image guidance, the decay time is short (e.g. 1 second) to accurately indicate where positive tumors are recorded.

Example 4

Imaging and Spectroscopy Systems Integrated with Endoscopes, Colonoscopes, Colposcopes, "Fiber-Optical Systems", or "Rigid Optical Systems"

This example describes endoscopes, colonoscopes, colposcopes, "fiber-optical systems" (fiberscopes), and "rigid optical systems" (borescopes) which record images from the remote end of a tube that may be flexible or rigid. Generally, such devices are divided into two classes: fiberscopes/borescopes and video endoscopes. Fiberscopes use a "coherent" fiber optic bundle (the position of each fiber is the same at each end of the bundle) to collect light at the remote end and transfer it to the local end. In contrast, borescopes use a series of relay lenses and (sometimes) glass cylinders to relay an image from the remote end to the local end. In both cases, light from the remote end is transferred to the local end for viewing. Video endoscopes place a camera sensor directly at the remote end and electronically transmit the image to a receiver (e.g., a television). Terms such as "endoscope", "endoscopic device", and the like are used herein as general terms that encompasses any such device, examples of which include those named for an intended purpose. Thus, a colonoscope is for inspecting the bowels, a colposcope for inspecting the cervix/vagina, and similar devices, are all encompassed in this example. The inner workings of the endoscope are the same across applications, although specific applications can have enhancing features.

Regardless of endoscope type, a key differentiating feature is that a miniaturized electronic device or "mini-Spectropen" is either used in the working channel of the endoscope device or integrated into the endoscope device. This scope provides point excitation of fluorescence or Raman. It also has a spectroscopic return that provides spectroscopy information of the point excitation area.

Coupling to Fiberscopes (Fiber-Optical Systems) or Borescopes (Rigid Optical Systems)

Coupling the widefield camera system to a fiberscope or borescope, utilizes an optomechanical coupler. One mechanical function of the coupler is to attach the widefield camera system to the eyepiece of the fiberscope or borescope. Another mechanical function of the coupler is to hold the optical part of the coupler so that the distance between the local end of the fiberscope or borescope, the optical coupler, and the entrance of widefield camera system is constant. The optical component of the coupler is also held centered and untilted with respect to the optical axis. The optical coupler is one or many optical elements (e.g., a lens) that transfers light from the local end of the fiberscope or borescope to the entrance of the widefield camera system. The widefield camera system may be configured to accept collimated light of a specified diameter or focal light of a specified focal length and numerical aperture. The optical coupler configuration matches that of the widefield camera system. Thus, if the system expects collimated light, the coupler collimates the divergent light emitted by the fiberscope bundle or borescope relay lens system with the needed diameter; if the system expects focal light, the coupler relays light emitted by the fiberscope bundle or borescope relay lens system with the necessary or desired focal length and numerical aperture.

Examples of fiberscopes or borescopes with digital camera attachments include those integrated in video endoscopes. Integrating a widefield camera system with a video endoscope utilizes a system that is miniaturized such that it can fit within the tip of a video endoscope. Integration can be carried out, for example, by using very small camera sensors with a multichannel prism (for example, a miniaturized 3CCD camera). Another method of integration is to use a single CCD with integrated spectral filtering. Multispectral capabilities for the single CCD could be granted through use of a multispectral mosaic filter (similar to a Bayer filter used with color sensors) or a vertically stacked sensor (such as those of Foveon, Inc./Sigma Corp.) designed for multispectral applications. For both strategies, the video endoscope will have the same imaging capabilities (30 fps video, multispectral) as the "large" widefield camera system.

Figure 14:
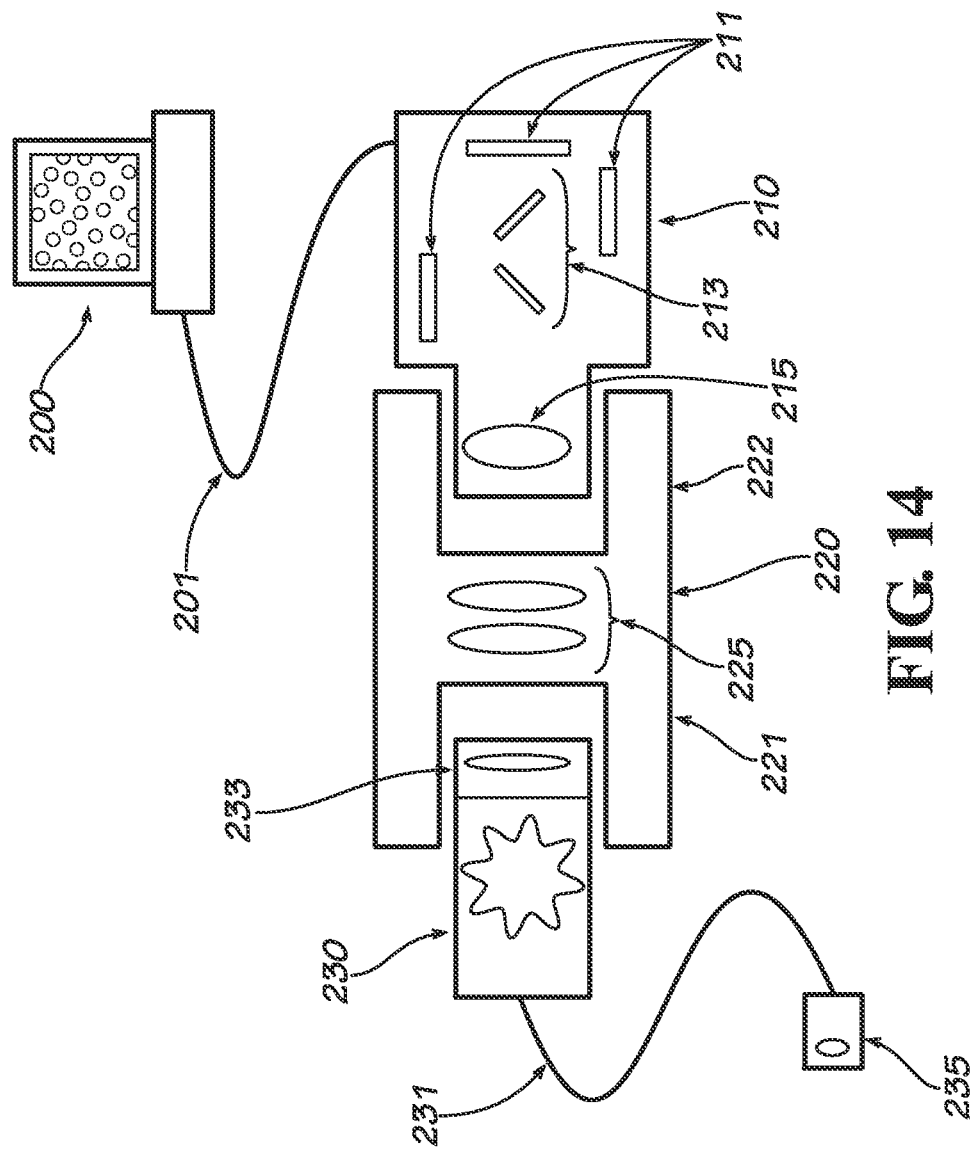
FIG. 14 illustrates one method of coupling the widefield camera system to a fiberscope or borescope, utilizing, for example, an optomechanical coupler.
Figure 15:
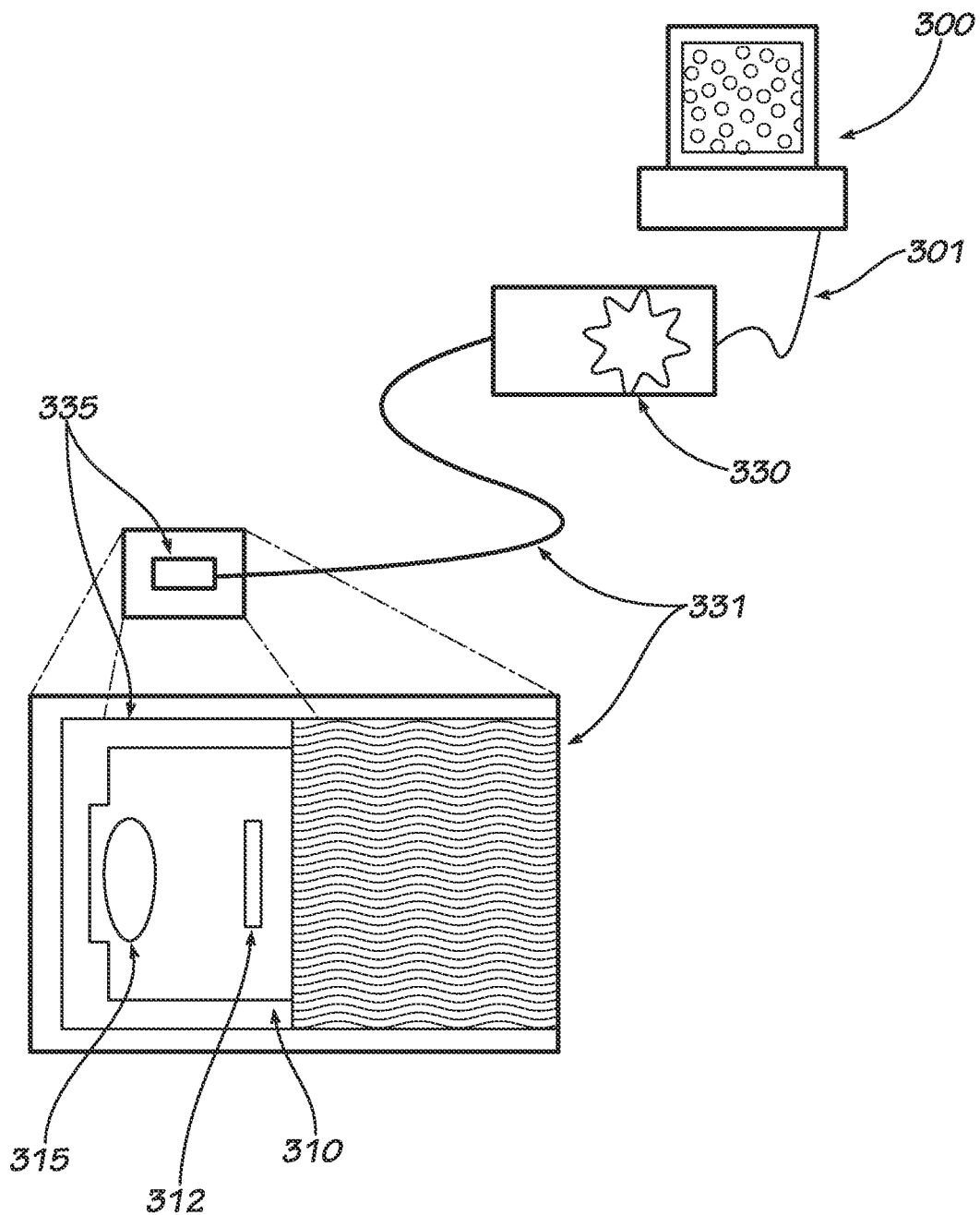
FIGS. 15 and 16 illustrate methods and embodiments for integrating a widefield camera system with a video endoscope utilizing a miniaturized system such that it can fit within the tip of a video endoscope and incorporating, for example, a multispectral camera sensor in a video endoscope.
Figure 16:
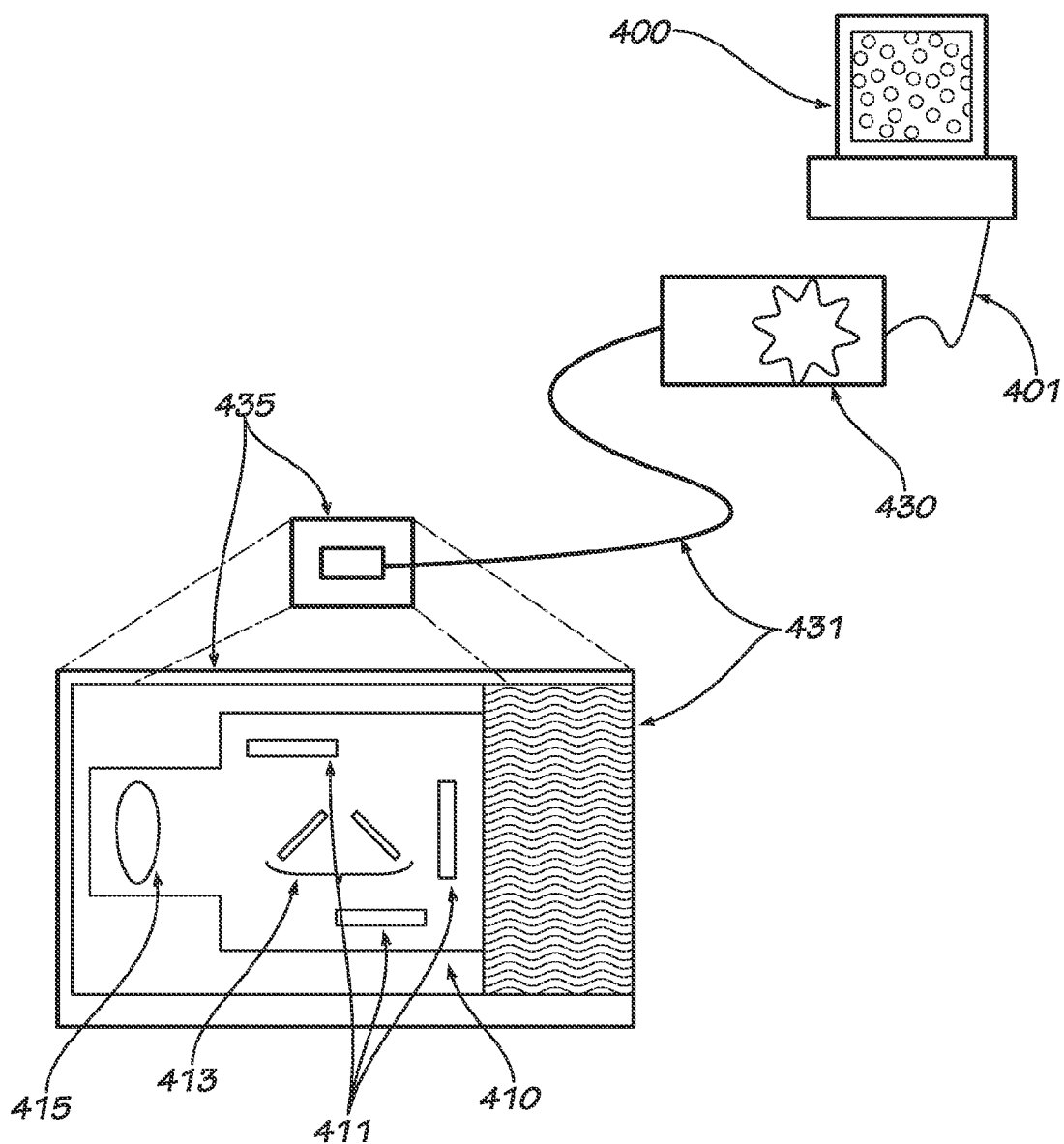

These principles and aspects are exemplified in the embodiments shown in FIGS. 14-16 and the list of figure elements provided in Chart 2. For example, FIG. 14 illustrates one method of coupling the widefield camera system to a fiberscope or borescope, utilizing, for example, an optomechanical coupler. FIGS. 15 and 16 illustrate methods and embodiments for integrating a widefield camera system with a video endoscope utilizing a miniaturized system such that it can fit within the tip of a video endoscope and incorporating, for example, a multispectral camera sensor in a video endoscope.

Example 5

Imaging and Spectroscopy Systems for Image-Guided Surgery Integral with Therapeutic Laser Systems This example illustrates surgical laser systems (e.g., carbon dioxide, argon, neodynium yttrium aluminum garnet) used in oncology for surface ablation of cancerous lesions, photocoagulation of cancerous lesions, and activation of photodynamic therapy agents. The present system integrates with therapeutic laser systems at a mechanical level by addition of the therapeutic laser to the local excitation and spectroscopy system (the "Spectropen box"). To this integrated system, additional software for control of the ablation functions can be added. The therapeutic laser could be used in open surgery, minimally-invasive surgery (i.e., endoscopic procedures), robotic surgery, and in drug-eluting devices and the like.

Hardware Modifications to Support Therapeutic Lasers

A therapeutic laser uses greater energies than the laser used for imaging and spectroscopy; therefore the imaging instrumentation generally is protected from the higher power laser emissions. The protection can be in the form of optical notch filters to reject only laser light or a physical shutter to block all light. In the case of a shutter, it is automatically triggered to block light only when the therapeutic laser is active. The integration of a therapeutic laser into the local excitation and spectroscopy system (the "Spectropen box") can be carried out by optically coupling the therapeutic laser into the system through standard optical elements (e.g., lenses, mirrors, prisms, and dichroics).

Software Additions to Support Therapeutic Lasers

Integrating therapeutic laser capabilities into the imaging system can allow the imaging system to precisely guide when and where the therapeutic laser action occurs, rather than the hands of a surgeon. The imaging laser and the imaging system is used to locate the position of the handheld probe within the patient (a function already done in the imaging system software). When the imaging system detects contrast agent in an amount indicative of tumor presence (a function already done in the imaging system software), it releases an interlock on the therapeutic laser. Typically, this interlock is one of a plurality of such safety devices, for example, a safety interlock that is disengaged only if a key if physically turned to the "on" position, or a safety interlock that is disengaged only if the handheld probe is pointed in a downward direction. All interlocks (hardware and software) typically are designed such that they must be disabled to activate the therapeutic laser. Activating the therapeutic laser automatically activates the imaging system shutter (if installed) while the laser is in operation, and deactivates the shutter when the laser is no longer in operation. The use of the therapeutic laser typically will destroy any contrast agent present in the treated region; therefore, an additional software function is provided to map the location of tumor positive areas, retain them, and present them overlaid onto the anatomical view, with proper registration. With this software feature, the therapeutic laser interlock is tied to the imaging system laser being in a tumor positive area and not actively detecting tumor.

Method of Use of Therapeutic Lasers Integrated with the Imaging System

As a baseline procedure, the patient typically is administered contrast agent such as indocyanine green before the procedure. In photodynamic therapy procedures, a photosensitizer such as porfimer sodium (Photofrin) or gold nanoparticles are also administered. This photosensitizer could be the same as the contrast agent or could be a separate agent. The physician would inspect the area of the cancerous lesion with the imaging device. If the physician intends to treat using the therapeutic laser, they will indicate to the system this intention through, for example, a foot pedal, button, switch, and the like. When the handheld or endoscopic probe is pointed at a cancerous lesion, determined by the imaging system, a pulse of energy from the therapeutic laser is emitted.

Example 6

Software Applicable to a Cancer Detection Device

This example describes a software protocol that can be used in the detection of cancer using the disclosed device. This example is divided among the various program loops and image processing tasks, as illustrated in this exemplary method.

As described, the imaging platform includes a high-resolution spectrometer (0.15 nm resolution) and a 200 mW, 785 nm diode laser (Class 3b) in a compact enclosure that is fiber-coupled by a 5 m cable and terminating in a 1 cm×5 cm handheld wand or "probe". Remotely controlled optical probes can be used in place of a handheld probe, as disclosed herein. The other half of the imaging platform is a widefield imaging system consisting of an 8 cm×10 cm aluminum breadboard to which 2 NIR-sensitive black and white CCD sensors, 1 color CCD sensor, a downward-facing C-mount objective lens, and 90° silver-mirror are mounted. A finite/infinite-conjugate relay lens system and multiple dichroic mirrors; bandpass and longpass filters are used to both direct light collected by the objective lens to all cameras and to confer wavelength selectivity to each camera. The color camera is used to display the surgical field, one NIR camera is used to display any detected NIR contrast agent, and the second NIR camera is used to track the position of the laser excitation source. Data acquired by the NIR cameras is used to composite a virtual overlay of contrast agent and laser position onto the surgical field view. Spectrographic data is combined with the laser position information is used to create a spectrographic overlay. Use of both the fluorescence and spectrographic overlays is complementary; the fluorescence overlay operates at real-time (30 fps) frame rate but is incapable of distinguishing contrast agent fluorescence from endogenous fluorescence sources or light scatter, whereas the spectrographic acquisition time is 1-2 fps in standard usage but has far greater discrimination of fluorescence sources.

This cancer detection device includes a strong local (i.e. focused) excitation source for fluorophore excitation that is coupled to a high-resolution spectrometer. The locally excited fluorescence emission is then overlaid onto a view of the surgical field. Some of the features or advantages achieved by this design include the following.

(1) Using a local excitation source allows for lower sensitivity (and lower cost) detectors to be used without sacrificing the sensitivity or utility of the system.

(2) The spectrometer allows for NIR contrast agents to be distinguished from endogenous NIR-emitting fluorophores, thus, the "NIR window" has a low but non-zero autofluorescence background.

(3) A local excitation source gives an intuitive sense for the location of detected contrast agent as the definition the contrast agent is detected wherever the spectrometer "pen" or optical probe is pointing.

(4) The strong local excitation used by this platform overcomes the limited sensitivity problems inherent in continuous wave imaging modalities.

(5) The use of a spectrometer in this platform prototype allows not only for NIR contrast agents to be discriminated against the biological background through deconvolution, but also allows for SERS Raman contrast agents to be used (not possible in any other imaging system).

Thus, this cancer imaging platform uses focused excitation to increase the detection limit of optical contrast agents. Complimentary wide-field imaging and local spectroscopy of the probe emission provides accurate intra-operative detection of the contrast agent, and spectral deconvolution from background or multiple probes.

Figure 17:
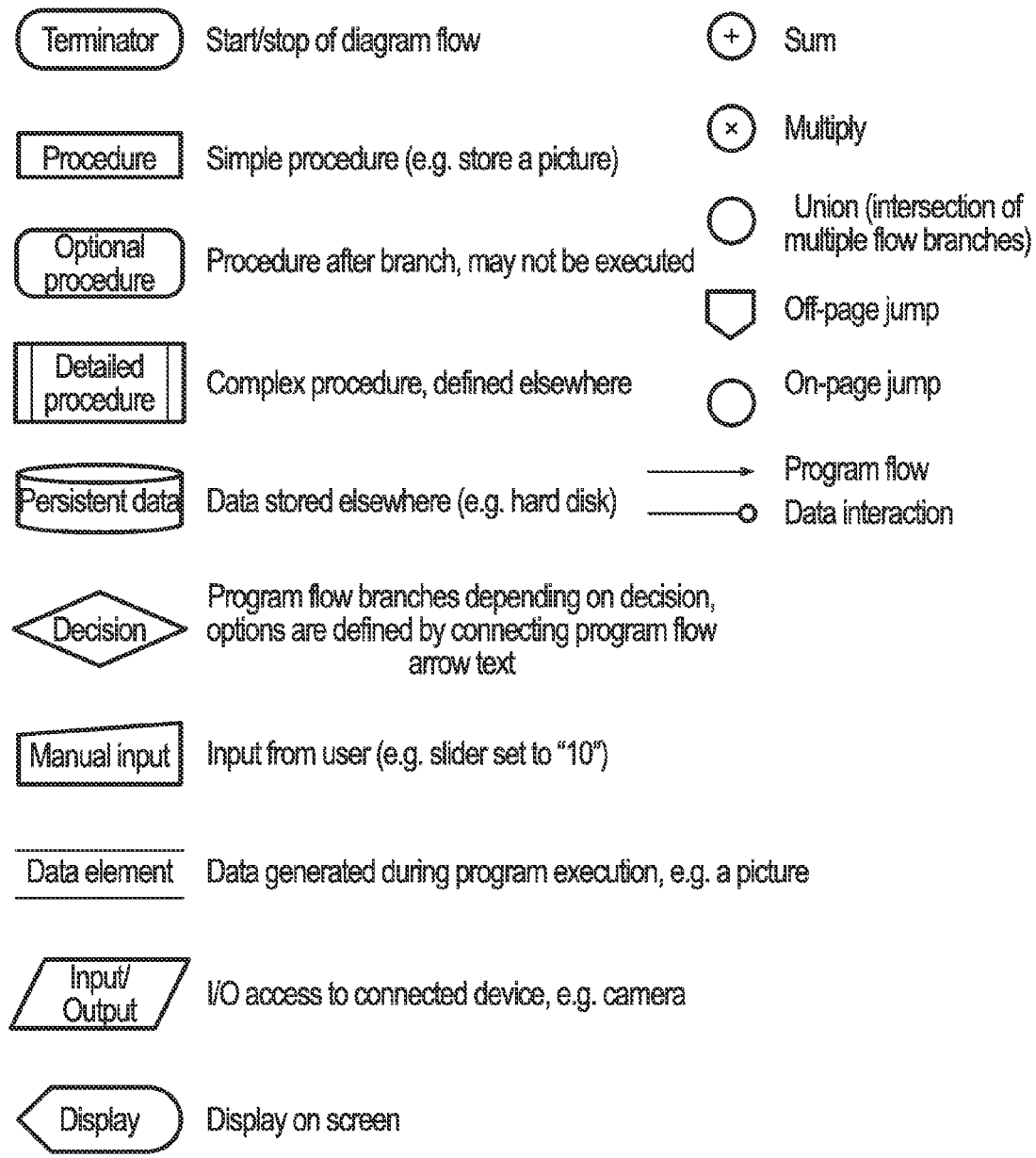
FIG. 17 provides a Flowchart Key that serves as a reference for FIGS. 18-27 in the discussion of the software and processing aspects of this example.

Reference is made to FIG. 17 for the Flowchart Key that serves as a reference for FIGS. 18-27 in the discussion of the software and processing aspects of this example.

Example 6A

Figure 18:
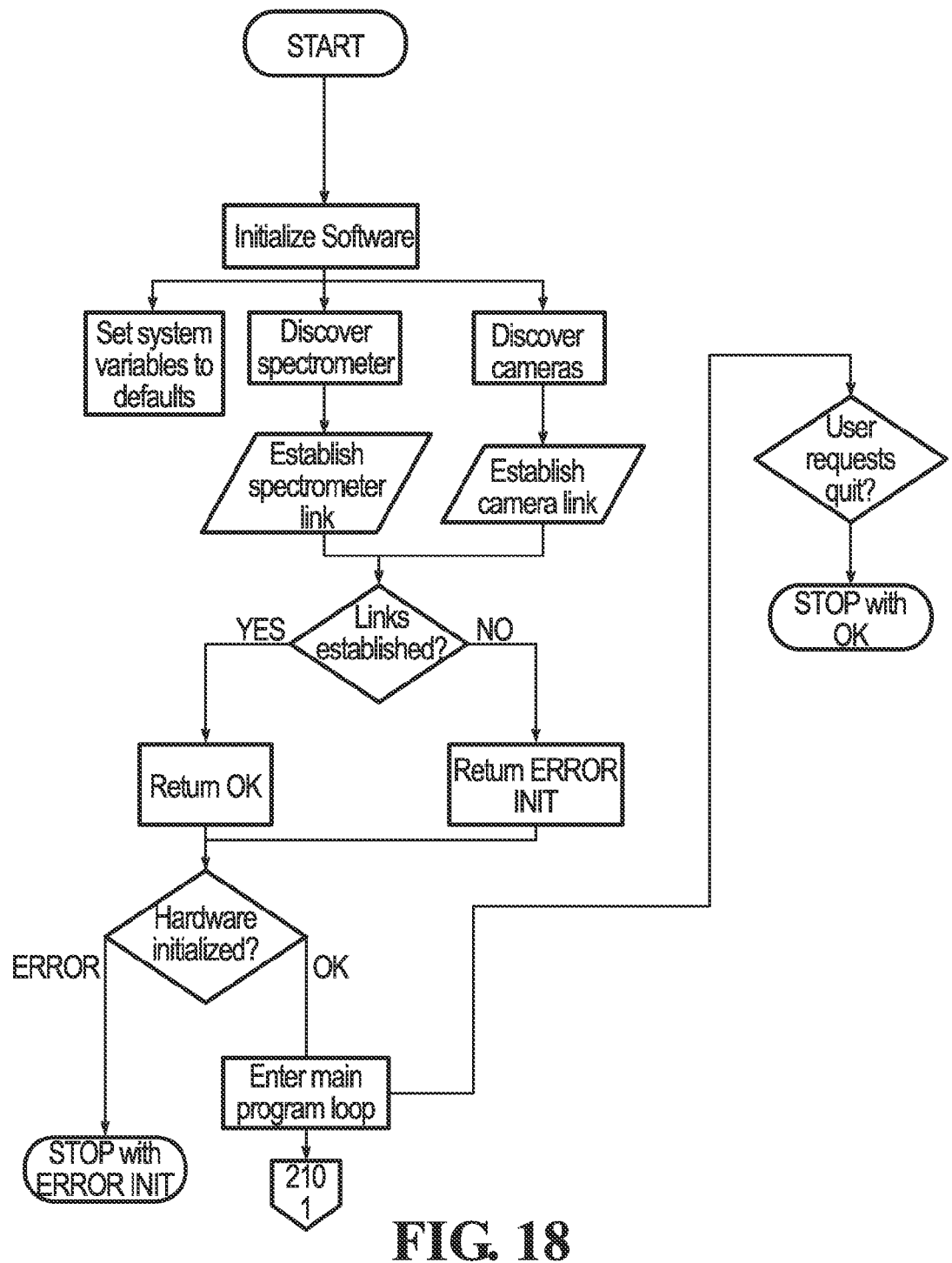
FIG. 18 provides a flowchart for a software startup method (200) as disclosed in the examples.

Software Startup (200, FIG. 18). Software was initialized and a check that peripherals such as cameras, spectrometer are connected is carried out. Load the default values for software configuration (like camera shutter speeds and gain). If any errors occur, stop the program and inform the user why; if no errors occur then execution continues to the main program loop (210) until the user closes the program.

Example 6B

Figure 19:
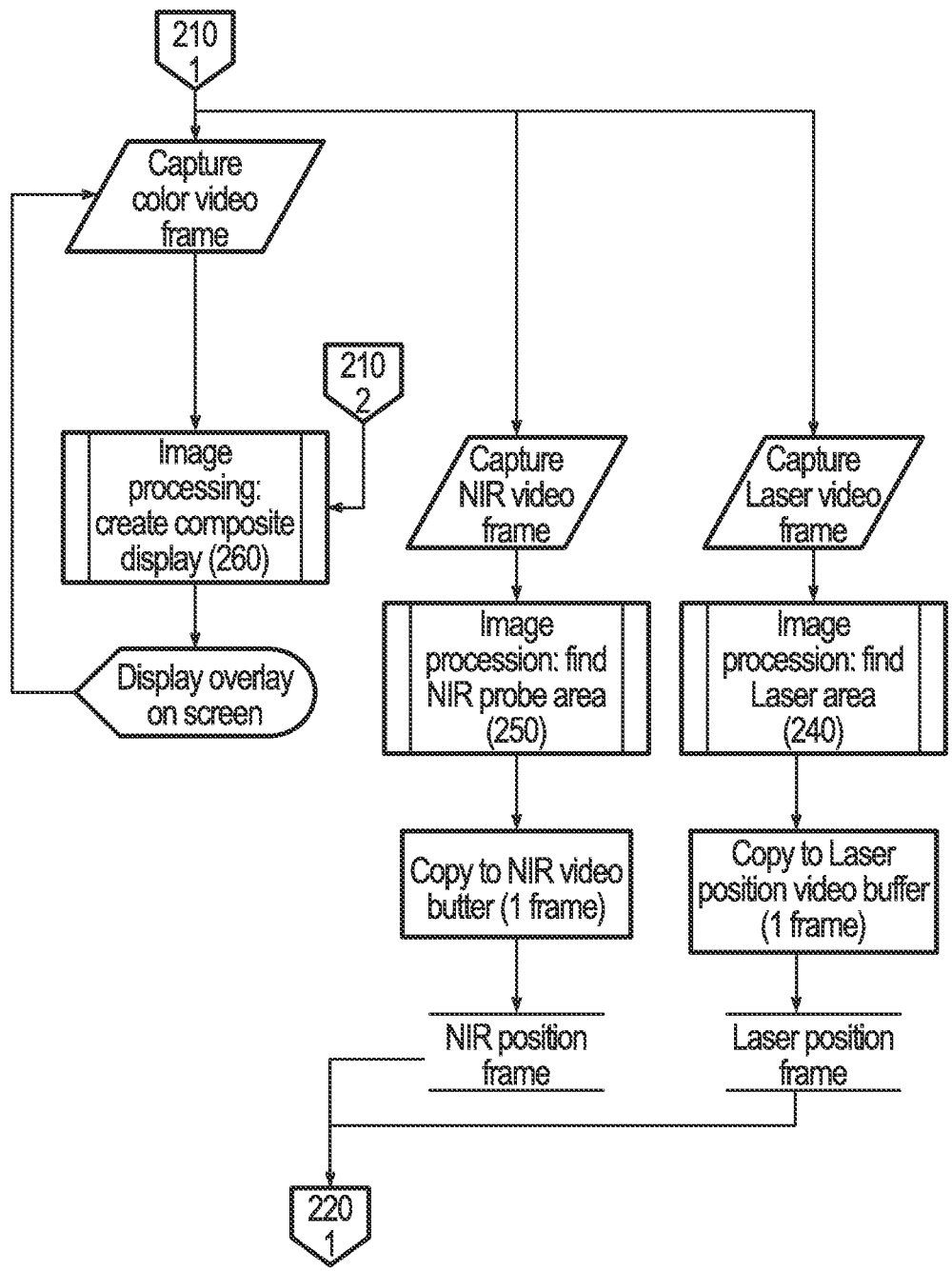
FIG. 19 provides a flowchart for a main program loop (210) as disclosed in the examples.

Main Program Loop (210, FIG. 19). Video frames from the cameras are continuously acquired and displayed to the user so long as the program is running. For every exposure of the NIR camera and Laser camera, the frames are processed to find the location of the probe and laser signal (250 for NIR, 240 for laser). The resulting masks showing the location of the probe or laser signal are then sent to the display mode selector procedure (220) which generates the overlay to be displayed based on the preferences set by the user. The overlay generated is sent to another procedure (260) to create the composite image. Not shown: the user can save the displayed images as single snapshots or as a video file—the data saved is exactly what is displayed on screen. Not shown: if the spectrometer is running, the resulting spectral data acquired can be shown on screen.

Example 6C

Figure 20:
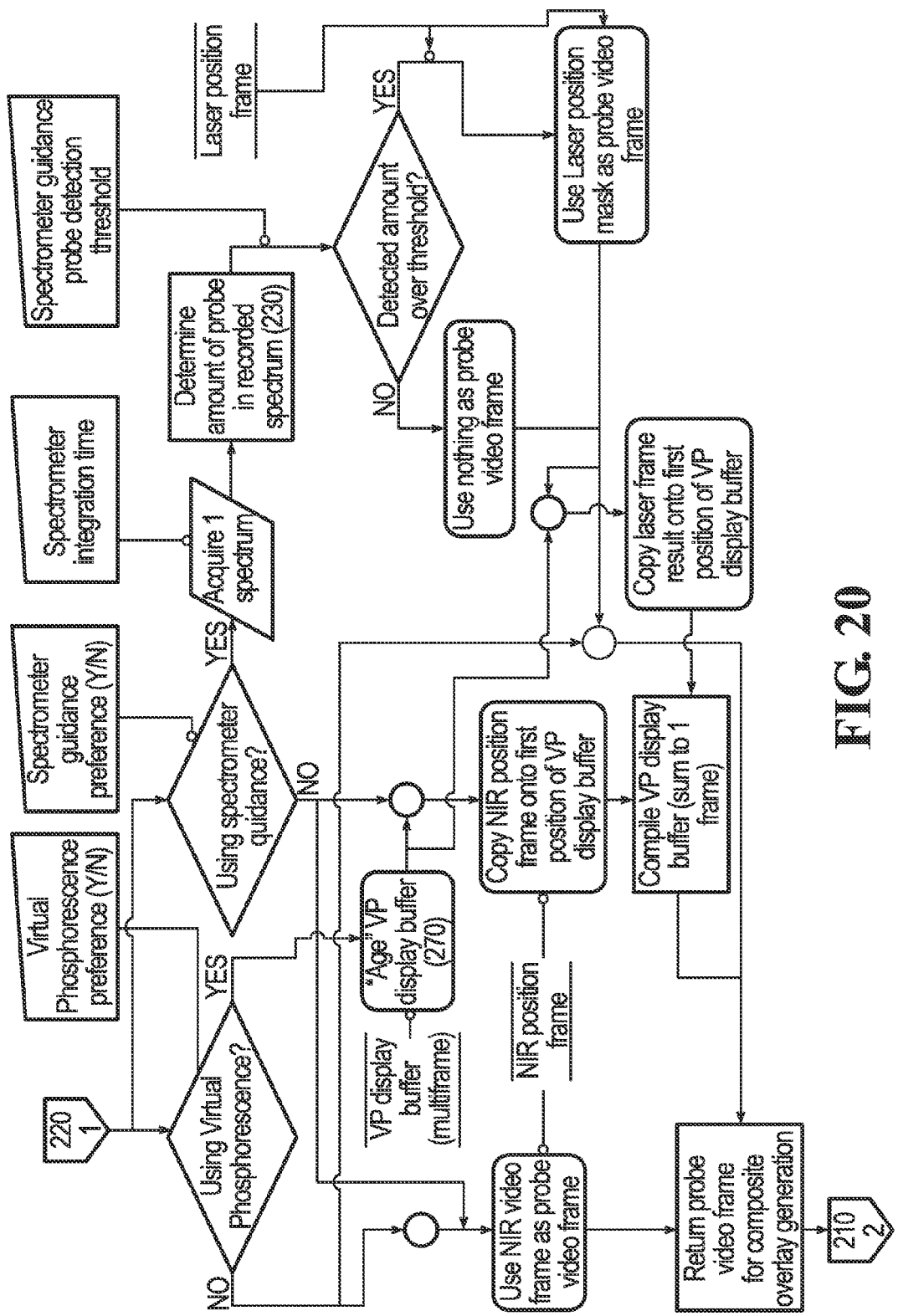
FIG. 20 provides a flowchart for a display mode selector component of image processing (220) as disclosed in the examples.

Image processing: display mode selector (220, FIG. 20). The user is able to enable overlay of data from the NIR camera or spectrometer for guidance; the user is also able to enable the "Virtual Phosphorescence" display that assists in determining the boundaries of the probe area.

If the NIR camera is used for guidance, the NIR video frame will be used as the probe mask (this data was already processed by 250).

If the spectrometer is used for guidance, then 1 spectrum will be acquired (the user sets the integration time), this spectrum will then be processed to determine if the probe is in the detection volume (230). If the amount of probe detected is greater than the set user threshold the laser position mask will be treated as the probe mask, otherwise no mask will be used.

For whichever mask is used, the position mask is returned to the main program loop (210) for overlay unless "Virtual Phosphorescence" is used. If Virtual Phosphorescence is used, then the VP display buffer is "aged" (270) and whichever probe mask is selected is placed on top of the buffer. This buffer is then compiled (summed into one resultant mask) and then returned to the main program loop (210) as one mask.

Not shown: if the spectrometer is being used for guidance, then the shutter speed of the laser camera is matched to the spectrometer. Not shown: the NIR camera can be reconfigured as a new laser position camera so that the laser position can still be shown.

Example 6D

Figure 21:
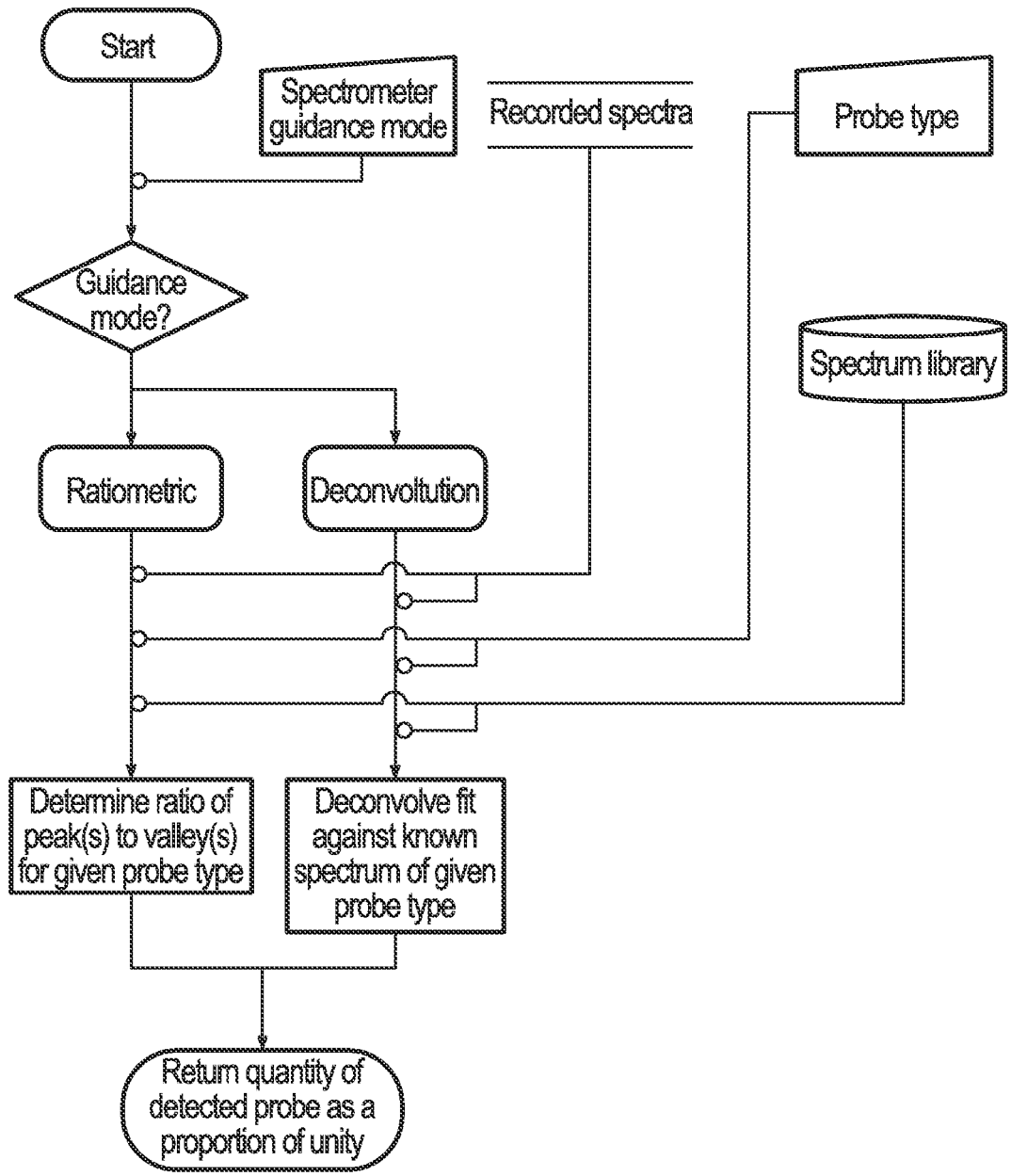
FIG. 21 provides a flowchart for determining the amount of probe in the recorded spectrum component of image processing (230) as disclosed in the examples.

Image processing: determine amount of probe in recorded spectrum (230, FIG. 21). The user is able to select a "guidance mode" for the spectrometer that determines by what methodology the recorded spectrum will be analyzed to quantify the amount of detected probe. For ratiometric guidance, the ratio of one or many pairs of points of the recorded spectra (typically peaks and valleys) are calculated—larger values denote larger amounts of detected probe. For deconvolution guidance, the recorded spectra is compared against known-good spectrum using an algorithm such as non-negative least squares—larger values denote a better match between the recorded and reference spectra and roughly correlate to the amount of probe in the detected volume.

Example 6E

Figure 22:
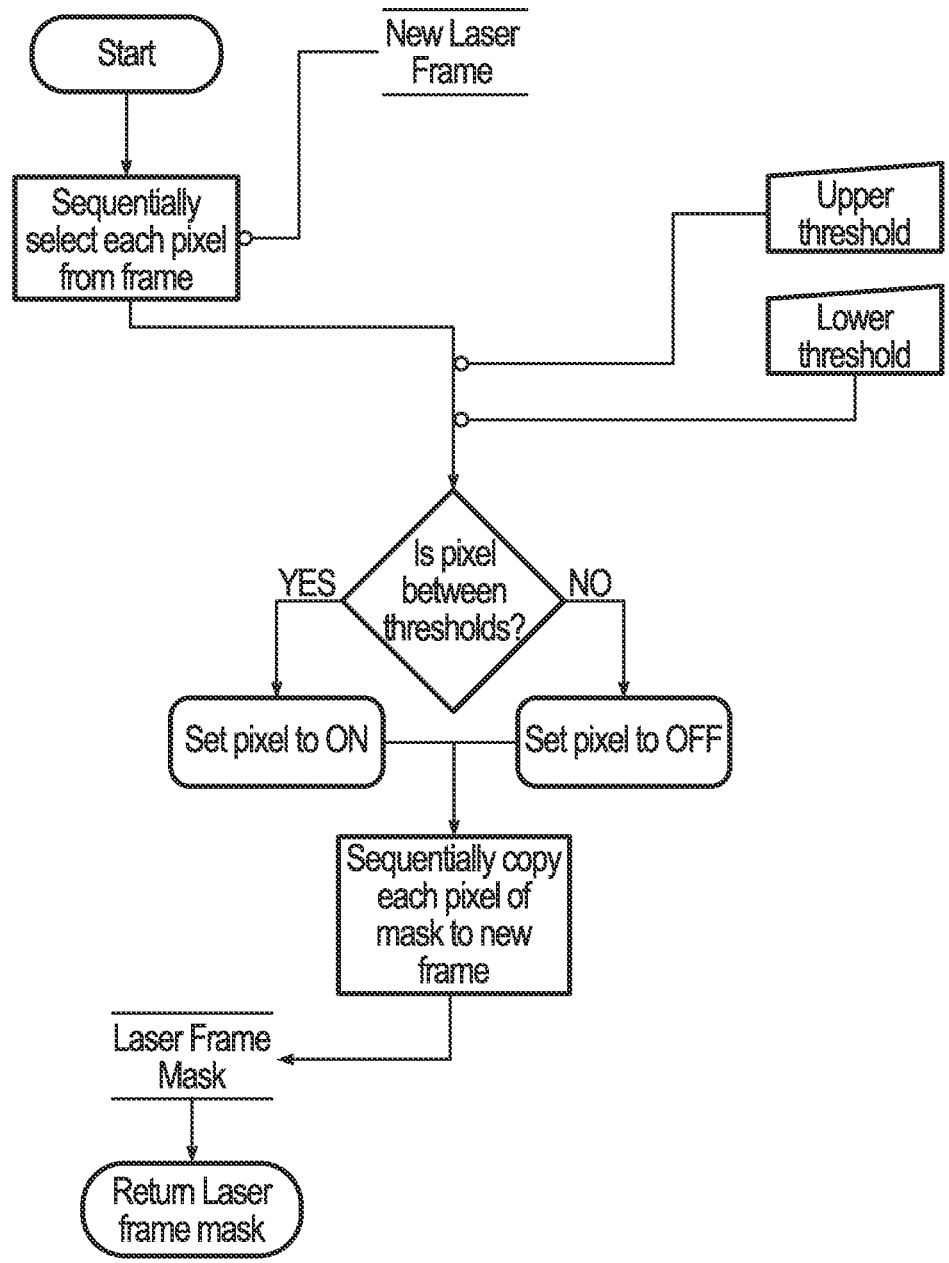
FIG. 22 provides a flowchart for finding the laser position component of image processing (240) as disclosed in the examples.

Image processing: find laser position (240, FIG. 22). The Laser camera frame is analyzed on a pixel-by-pixel basis. If the pixel in question is between a user set threshold pair (lower and upper), then the pixel of a mask to be generated is set to ON; if the pixel in question is outside of the threshold range, the pixel for the corresponding pixel on the mask is set to OFF. This process makes the laser mask appear as a ring around the laser position. Not shown; if the spectrometer is being used for display guidance, then the upper threshold is set to the maximum value—the laser position is then shown as a filled circle instead of a ring.

Example 6F

Figure 23:
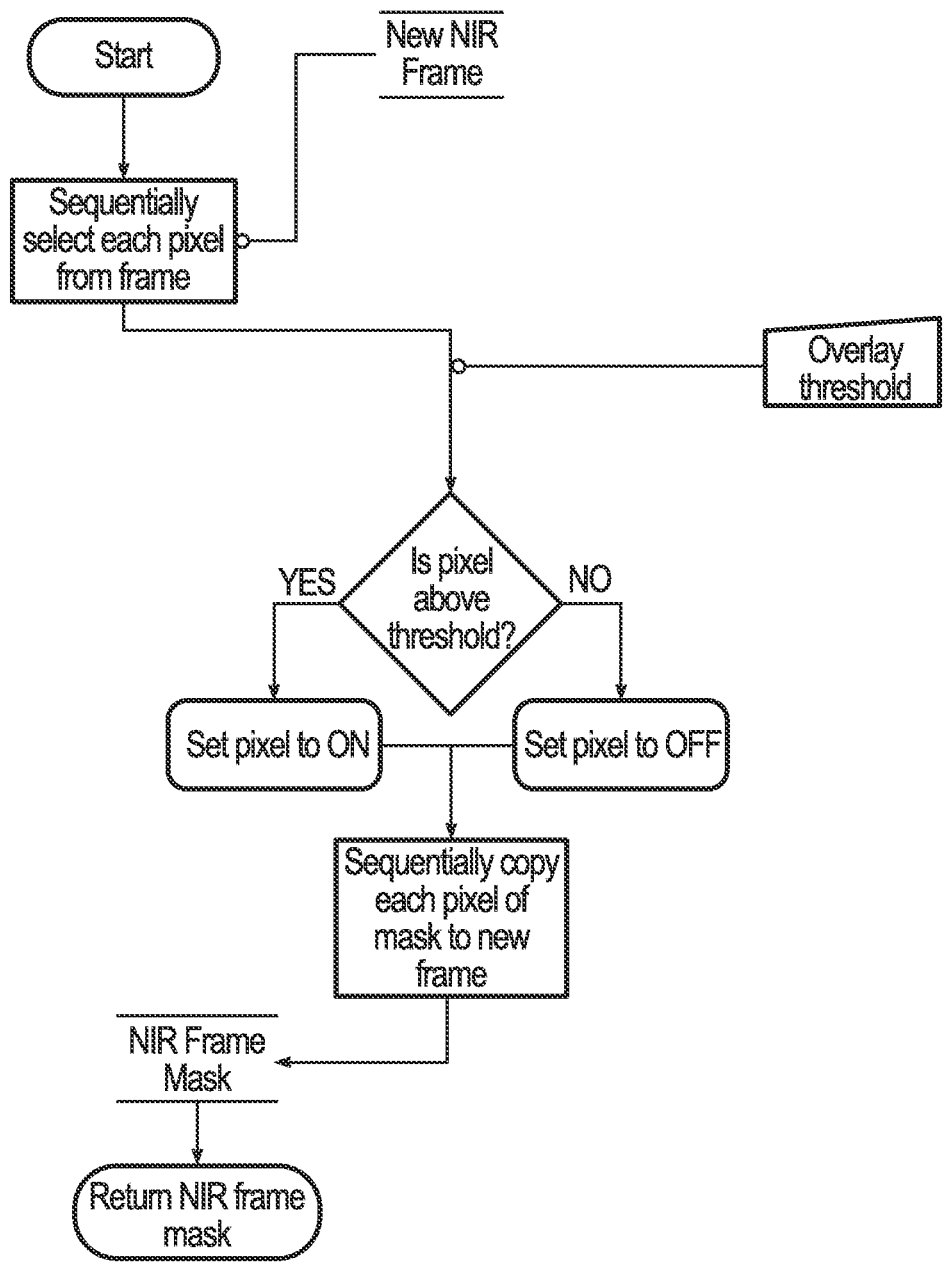
FIG. 23 provides a flowchart for finding NIR probe position component of image processing (250) as disclosed in the examples.

Image processing: find NIR probe position (250, FIG. 23). The NIR camera frame is analyzed on a pixel-by-pixel basis. If the pixel in question is above a set user threshold, then the pixel mask to be generated is set to ON, otherwise the pixel for the mask is get to OFF. The resulting mask corresponds to the area where detected NIR probe is concentrated above a given quantity.

Example 6G

Figure 24:
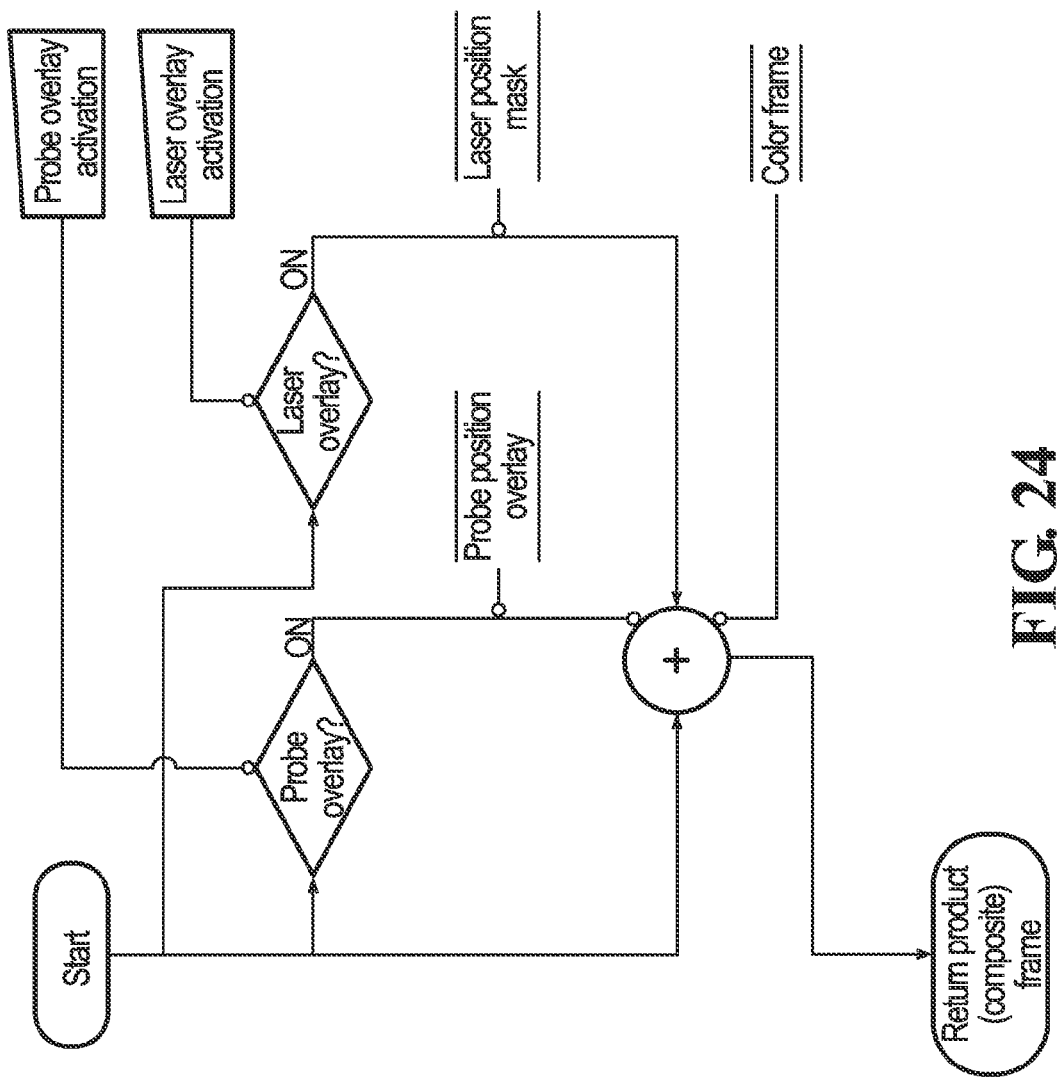
FIG. 24 provides a flowchart for creating a composite display component of image processing (260) as disclosed in the examples.
Figure 25:
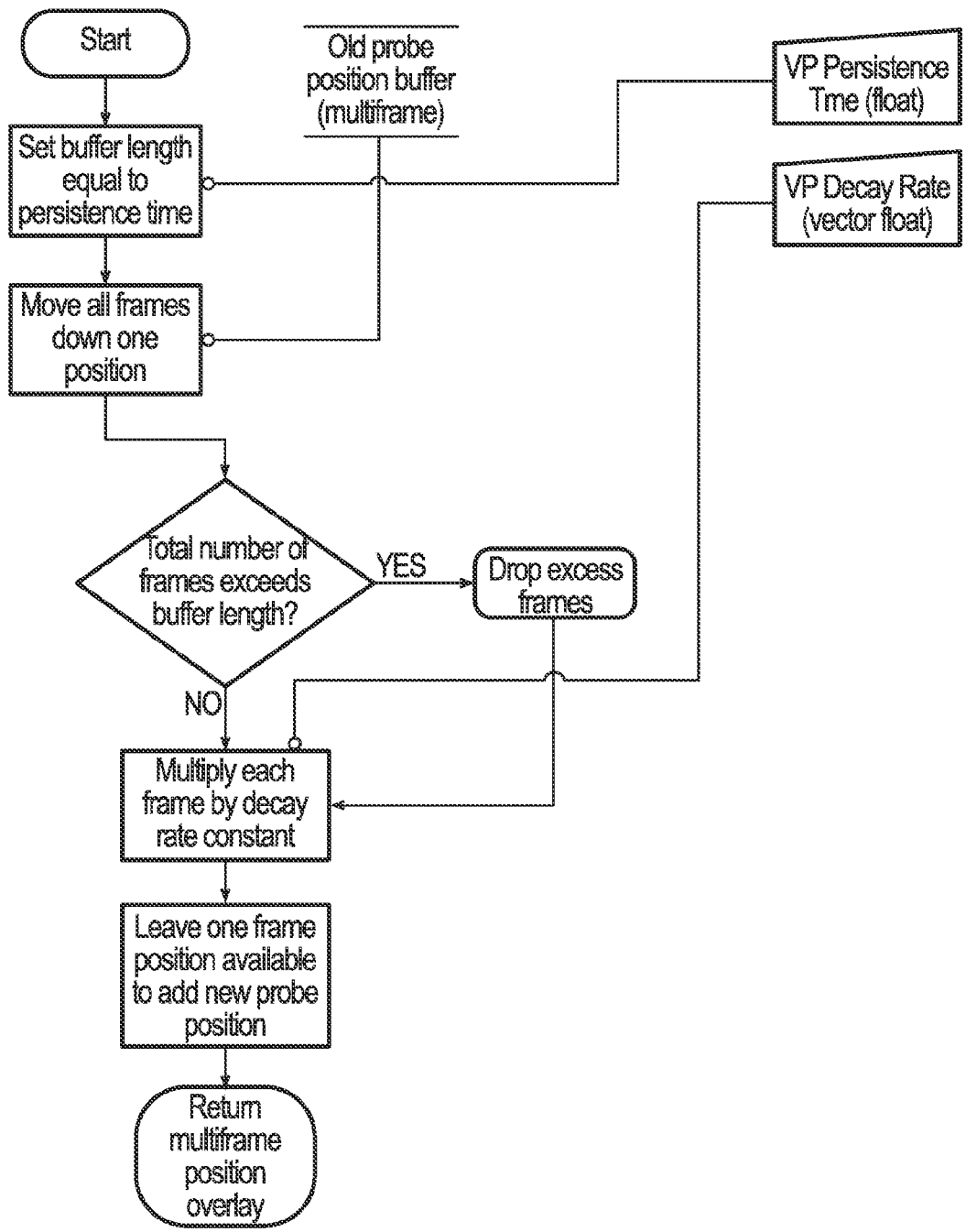
FIG. 25 provides a flowchart for the "age" probe buffer (for Virtual Phosphorescence) component of image processing (270) as disclosed in the examples.

Image processing: create composite display (260, FIG. 24). The user is able to enable the overlay of either probe or laser position. If either or both are enabled, the masks are summed opaquely with the widefield color video frame using a false color that contrasts well with the surroundings: typically cyan for detected probe and magenta for the laser position. When "Virtual Phosphorescence" display is used (selected in 220 and processed in 27), the overlay is done translucently, with the opacity corresponding to newer probe masks.

Example 6H

Figure 26:
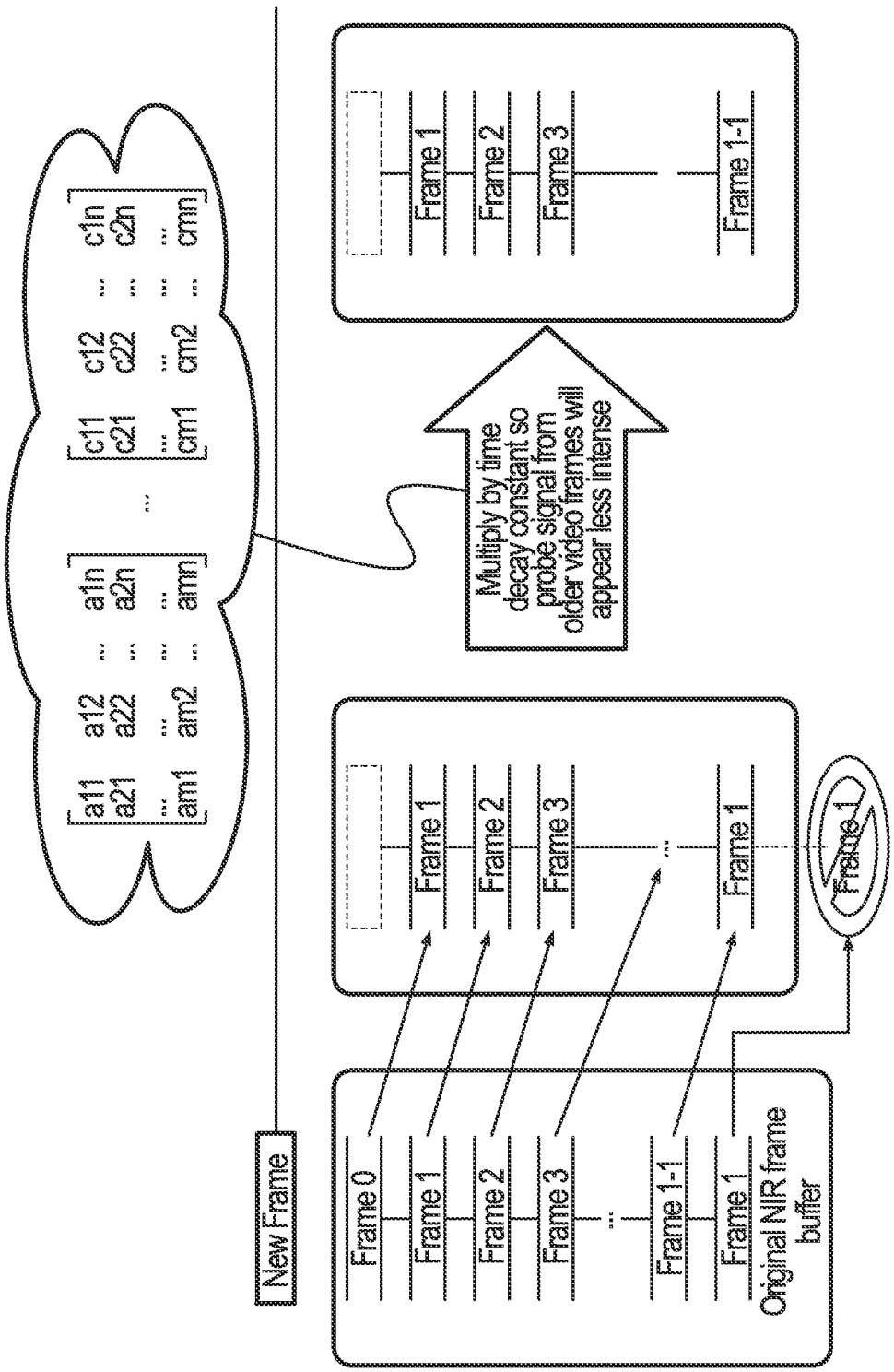
FIG. 26 illustrates a flowchart of the processing algorithm for the Virtual Phosphorescence (VP) component of image processing as disclosed in the examples.

Image processing: "age" probe buffer (for VP) (270, FIG. 25). The "Virtual Phosphorescence" display mode is in effect an analog time-delay and decay filter. When enabled, a buffer of probe mask frames is created with a length equal to the user set persistence time (the maximum time that the phosphorescence effect can be seen). Each iteration of the aging algorithm shifts each frame down one position in the buffer. Then, each frame is multiplied by a decay constant: this makes the contents of each frame appear "dimmer" after each iteration. The decay constant can be a single value (e.g. 0.9 for a 10% intensify decrease every iteration) or an array of values (e.g. 0 9 to 0.5 for a 10% to 50% intensity decrease every iteration, with older frames dimming much faster), these values can range linearly, logarithmically, or by another distribution. FIG. 26 illustrates a graphical flowchart of the processing algorithm for the Virtual Phosphorescence (VP) component of image processing as disclosed in the examples. The resulting multiframe structure is returned to 220 where the newest probe frame is pushed onto the top position of the buffer and compiled into one frame to be overlaid (described in 220).

Figure 27:
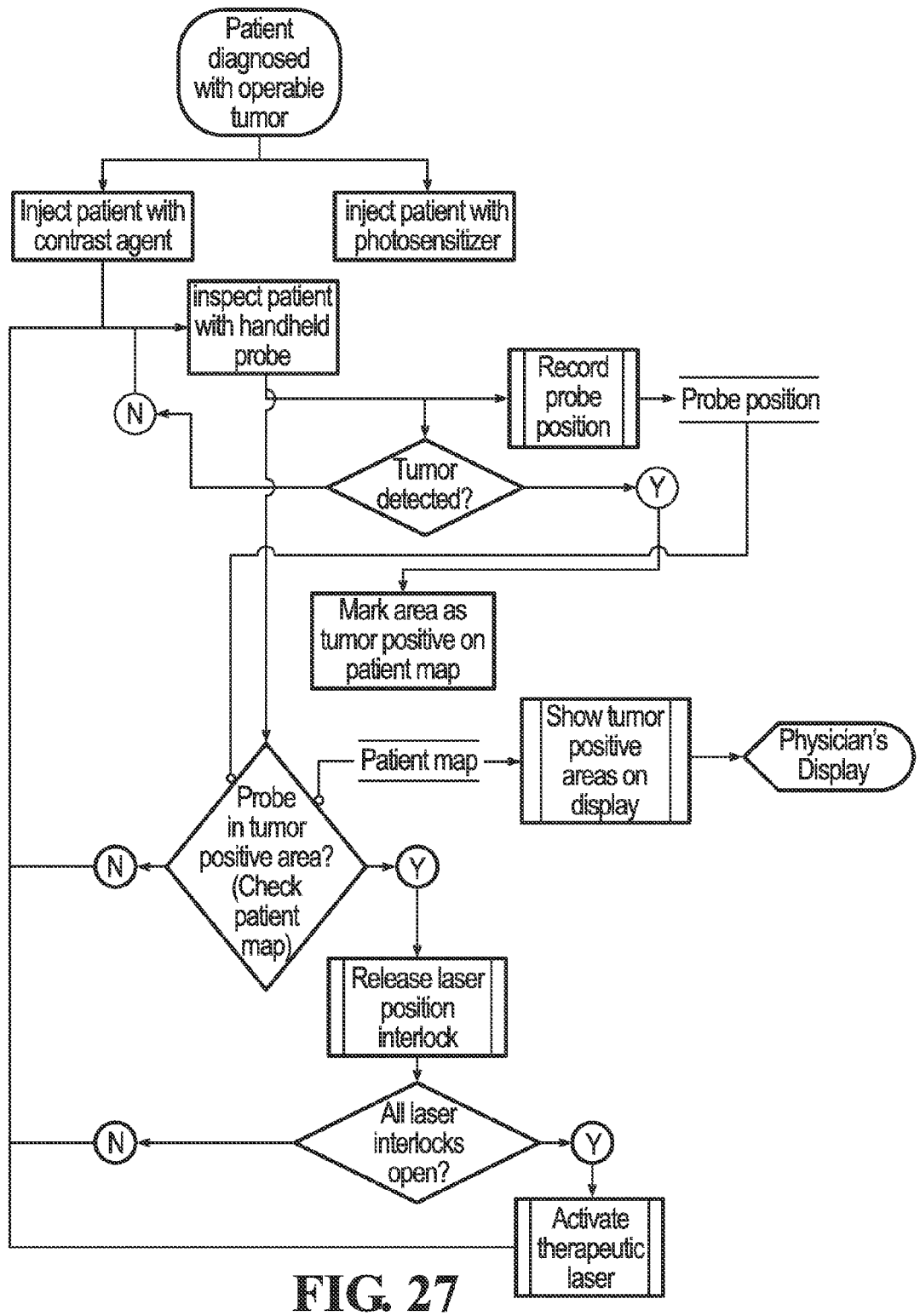
FIG. 27 provides a flowchart for one embodiment for using the disclosed therapeutic laser system.

Finally, FIG. 27 illustrates a flowchart for one embodiment for using the disclosed therapeutic laser.

Example 8

Detection of Murine GI Polyps

This example describes the detection of polyps in the murine FAP model, Apcmin/+. This study was conducted in two mice. Two mice were injected with 2 mg/kg ICG. One mouse received ICG intravenously via a tail vein. The other mouse was administered ICG intraperitoneally. After ICG had circulated for 20 h, the mice were euthanized, the lower GI was removed, washed extensively, sectioned roughly into four segments; duodenum, jejunum, ilium, and cecum and colon, and formalin fixed. The mice were then imaged using the integrated imaging and spectroscopy imaging system as provided in this disclosure.

Figure 28:
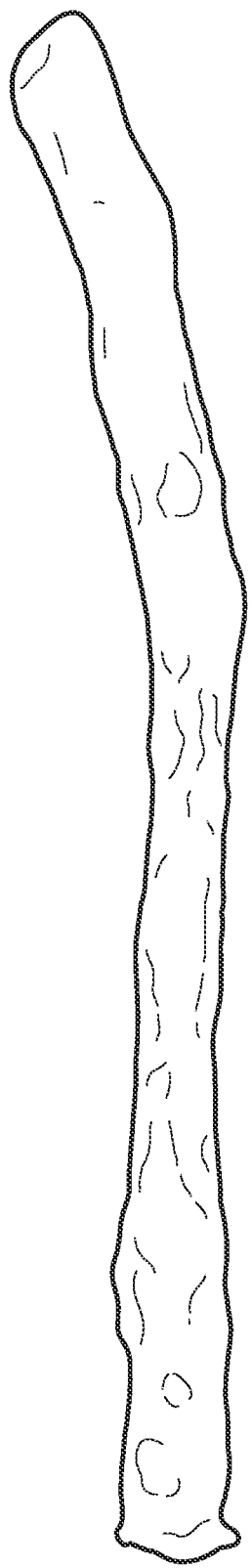
FIG. 28 provides an image of the jejunum lumen from $Apc^{min/+}$. The intestinal segment was cut lengthwise so it can be placed flat on the dissection pad for imaging.

The following imaging protocol was used:
1. Intestinal segments were rinsed with PBS. The segments were placed on a dissection pad such that the luminal side of the intestine was facing up (see FIG. 28).
2. Next the "SpectroPen" handheld probe was placed 1 cm above the intestinal tissue and clamped into that position for consistent repetitive acquisitions. The 1 cm space between the SpectroPen and the tissue correlates roughly to a 1 mm laser spot size.
3. Spectra were acquired and recorded from apparently healthy sections of the intestine (considered background signal), and polyps. An integration time of 1 s was utilized.
4. When the background signal (signal from healthy intestine) was low enough, wide-field color imaging with directed excitation provided by the SpectroPen was used.

General Observations

The mouse that receive a 2 mg/kg dose of ICG via a tail vein had approximately 22 polyps in its small intestine as detected by a dissection microscope and 1 large polyp in the colon. Since these doses were at the maximum recommended dose, the internal organs were briefly inspected for any aberrant signs of toxicity. In this mouse the organs appeared healthy. The liver, kidney and spleen were normal color and size. Also, no dramatic behavioral changes in the mouse were observed. These findings are consistent with this dose being within the safe limits of ICG.

The mouse that received the 2 mg/kg dose of ICG intraperitoneally had approximately 44 polyps in the small intestine and none in the cecum or colon. Upon observation of the internal organs, a pale color was immediately noticed, especially in the liver and kidneys, and the spleen was dark red, nearly black. In addition, these organs were stiff and inflexible. These observations were likely due to anemia since the polyps in this mouse were numerous and large.

Comparison of Polyp and Background Signal

For both mice, a polyp of 1-2 mm in diameter generally was needed, the subject polyp being in relative isolation from other polyps, for the polyp to be imaged without microscope assistance. Therefore, for the mouse with i.v. ICG the signal from 15 polyps was acquired and for i.p. mouse the signal from 14 polyps was acquired, and in each mouse, 1-3 background spectral readings were recorded from each segment.

The I.V. Injected Mouse

Figure 29:
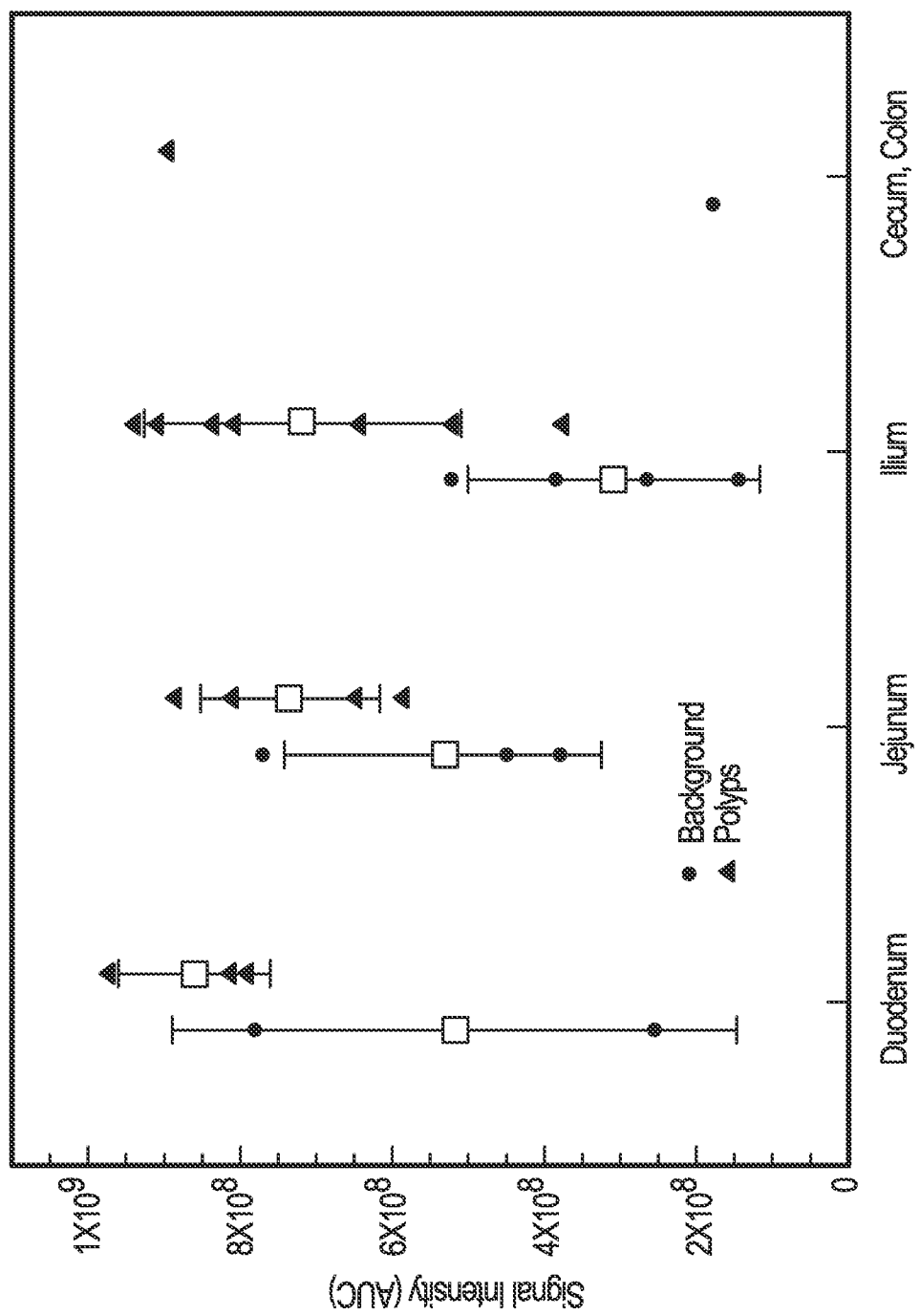
FIG. 29 illustrates signal intensity data from the GI tract of mouse injected with 2 mg/kg indocyanine green (ICG) intravenously. Closed circles represent individual polyps and background measurements and open squares are the average values for the background or polyps in the corresponding intestinal section. In each of the four sets (pairs) of measurements, the black or left hand set of data represents background measurements and red or right hand set of data represents polyp measurements.

The mouse intravenously with ICG appeared to have higher signal in polyps then in the background tissue as shown in FIG. 29. There was considerable variation in the signal intensity between different polyps and different background readings. Polyps found on the ilium had ICG signal statistically significant from background signal ($p=0.0252$). There were not enough data points to perform a statistical analysts for the colon. However, there was a large difference in the signal between the polyp and background.

Figure 30:
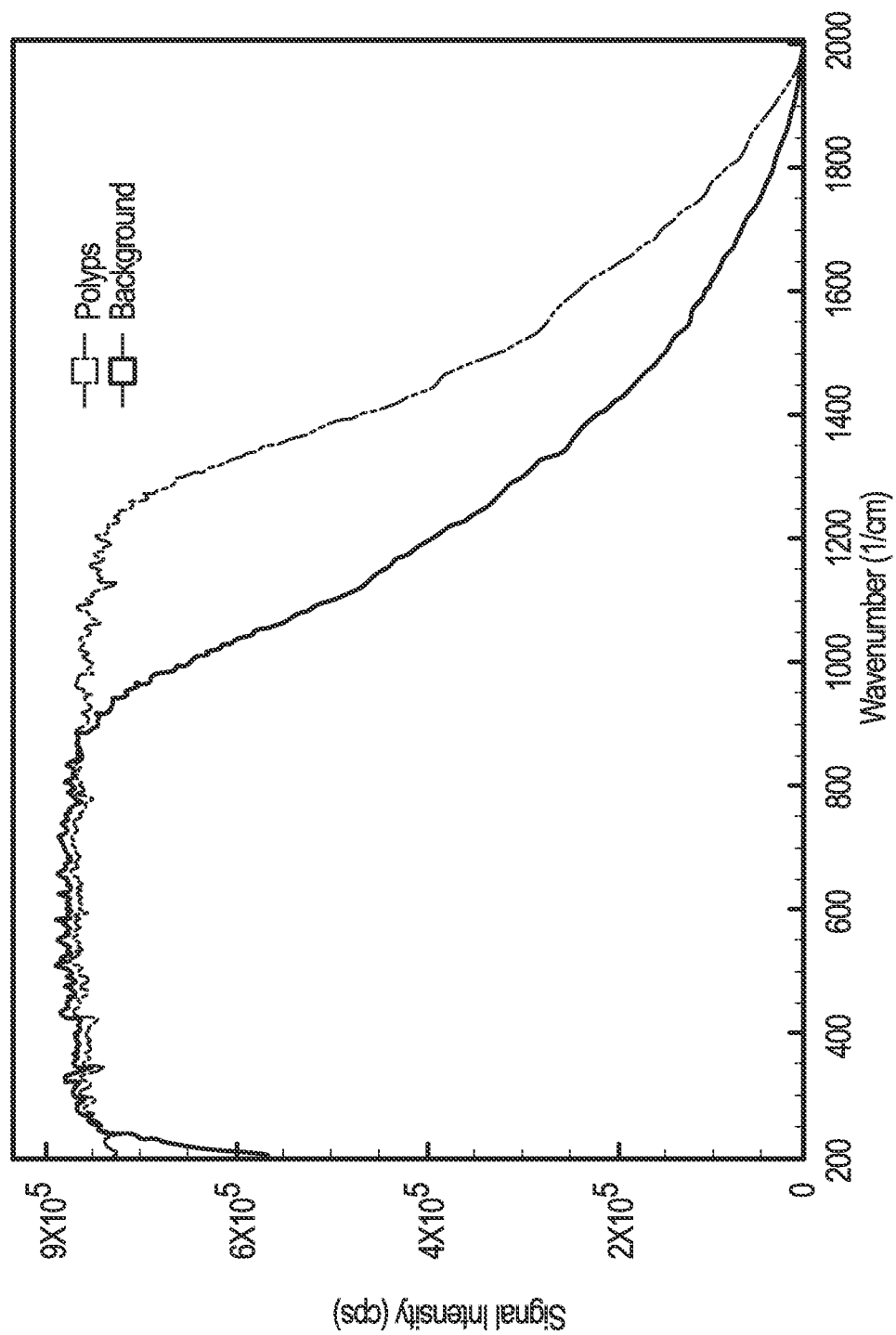
FIG. 30 demonstrates how indocyanine green (ICG) emission spectra from background (blue or left curve) and polyp (red or right curve) can saturate the detector at the dose used for the study of the intestinal lumen from $Apc^{min/+}$ described in the examples. This feature can alter the signal calculated for a given background or polyp measurement.

To quantify the emission signal, the AUC of the curve was calculated. Therefore, the signal intensity values in FIG. 29 are not fully representative of the ICG signal being emitted from either the background in some cases or the polyp since the emission detector was saturated at this dose. For example, in FIG. 30, spectra of the background and a polyp in the i.v. mouse's duodenum are shown. It is apparent from these curves that although the polyp does emit more signal, this difference is not fully represented because the spectra from the polyp from 300-1300 wavenumbers is out of the range of the detector. The same is also true for background spectra that saturate the detector in that this case may over-represent the contrast.

I.P. Injected Mouse

Figure 31:
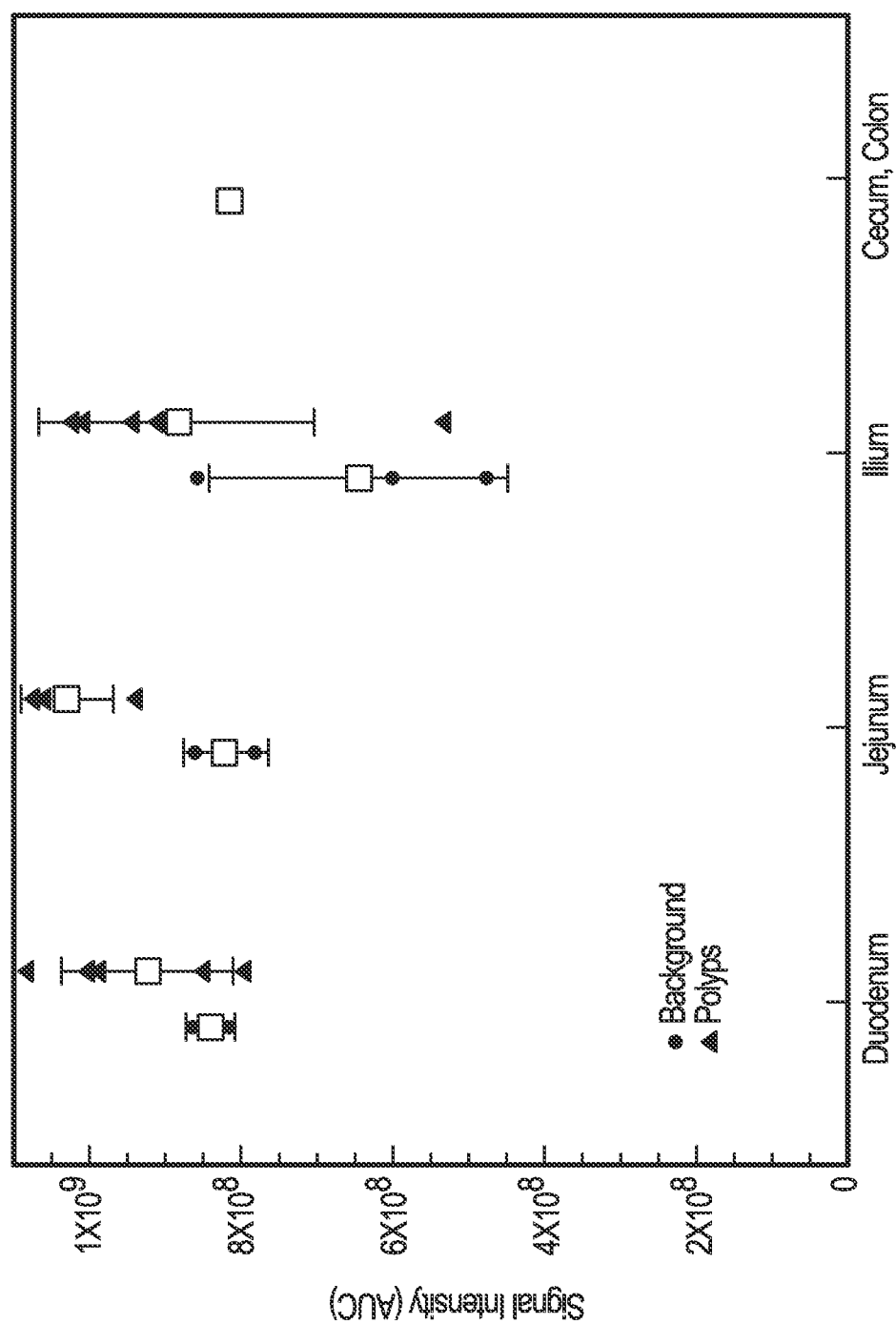
FIG. 31 illustrates signal intensity data from the GI tract or mouse injected with 2 mg/kg indocyanine green (ICG) Intraperitoneally. Closed circles represent individual polyps background measurements and open squares are the average values for the background or polyps in the corresponding intestinal section. In each set of measurements, the black or left hand set of data represents background measurements and red or right hand set of data represents polyp measurements.

Again in the GI tract of the mouse injected intraperitoneally with ICG, the signal from ICG in the polyps was greater than in the background as shown in FIG. 31. In the jejunum this difference was significant ($p=0.0016$). Like the i.v. injected mouse, these differences in the signal are not completely known since the signal was saturated. In fact, the relatively smaller variation observed for the polyps in the i.p. mice compared to the i.v. injected mouse in FIG. 29 is likely due to the signal being so strong in the i.p. injected mouse that the detector was saturated except at the longest wavelengths in the duodenum and jejunum.

Route of Administration and Effect on Background Signal

Figure 32:
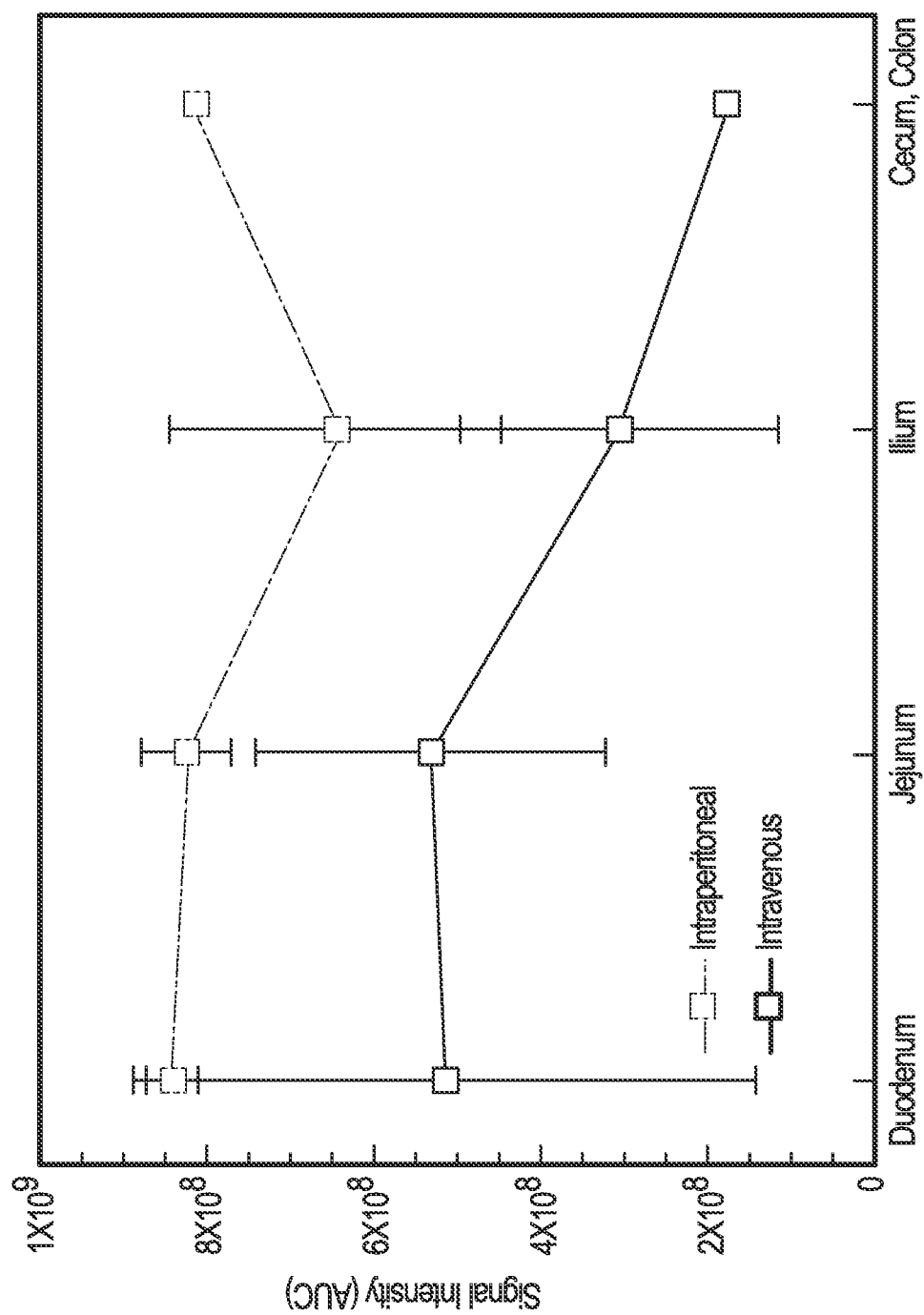
FIG. 32 Signal Intensity data from various sections of the GI tract of mouse injected with indocyanine green (ICG) either intraperitoneally (red, top line) or Intravenously (black, lower line).

With respect to the imaging time that was used after injection, i.e. 20, and the dose, 2 mg/kg, the route of administration has an effect on the background signal and thus the contrast enhancement. As illustrated in FIG. 32, it is apparent that the mouse injected intraperitoneally had a larger signal in the GI tract compared to mouse injected i.v. with ICG. Further, there appears, at least after i.v. injection, that the background signal decreases as one images towards the colon. While not intending to be bound by theory, it is believed that this is related to the hepatobiliary clearance of ICG. It is known that ICG is secreted entirely into bile. The bile duct empties into the duodenum and thus ICG may be associated with the intestinal mucosa. Thus, it is observed that background signal is lowest in the colon after i.v. administration.

Colon Polyp Detection

Figure 33:
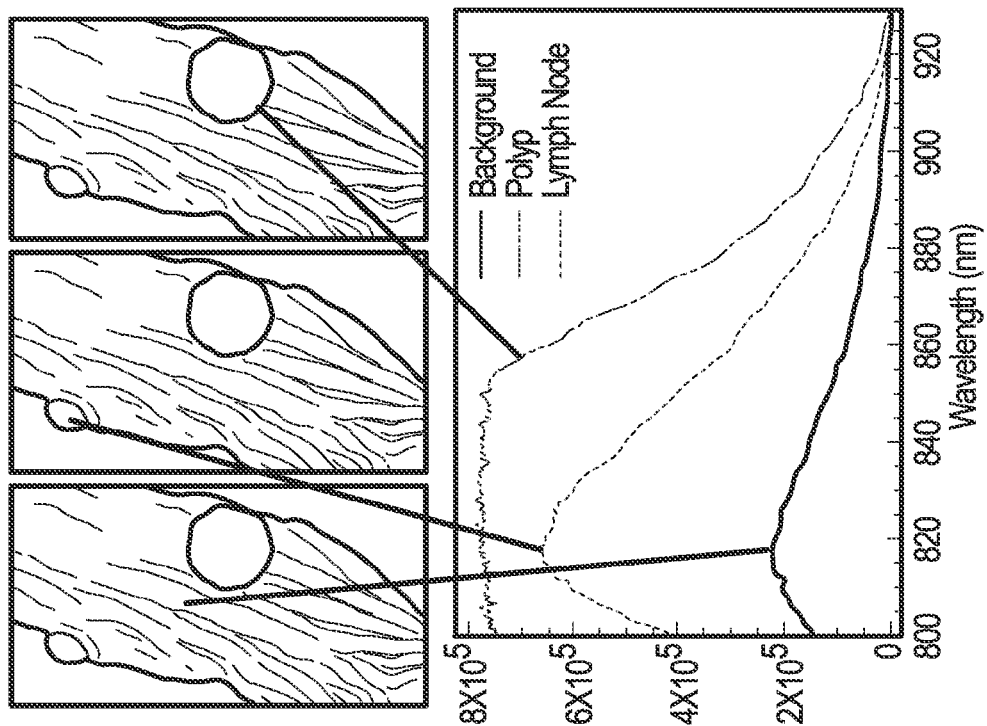
FIG. 33 (Left) Photograph of colon in $Apc^{min/+}$ mouse. A lymph node was also observed in close proximity to the polyp. (Right, top) Imaging provided by the integrated Imaging and local, focused excitation system shows no contrast enhancement in the healthy colon and strong contrast enhancement (blue false color) in the lymph node and polyp. (Right, bottom) Spectra from the background, lymph node, and polyp, recorded with the SpectroPen show at least a 5 fold greater signal from the polyp compared to the background.
Figure 33:
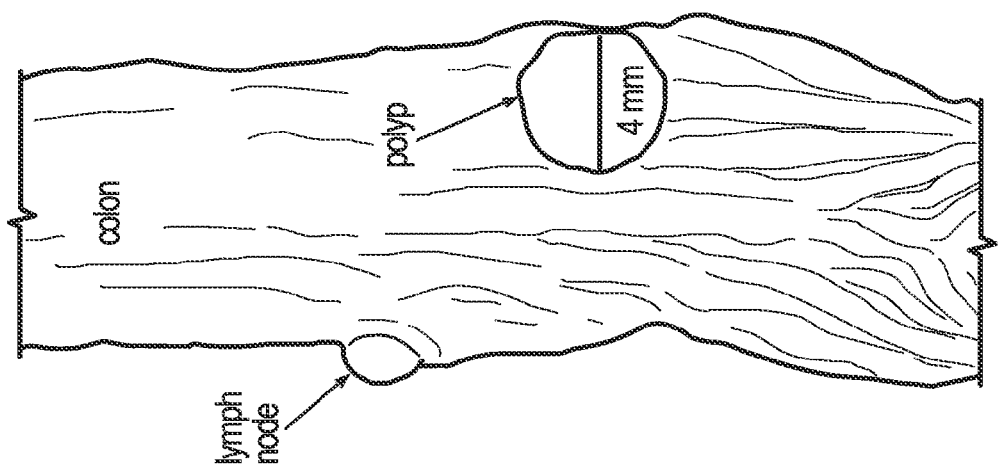

In the mouse injected with ICG via a tail vain, after harvesting the tissues, a colonic polyp was observed. A detailed investigation was performed on this polyp since polyp identification during colonoscopy is of significant interest. The polyp was approximately 4 mm in diameter and was thus easy to identify without further visual aid, FIG. 33. The ICG emission intensity of this polyp was similar to polyps observed in the small intestine sections. However, since the background ICG signal in the colon was lower compared to other sections, the signal difference between the polyp and healthy colon was dramatic and allowed segmentation for integrated wide-field imaging. In addition to the polyp, a strong signal in a lymph node in close spatial proximity to the polyp also was observed. Thus, the ability to readily detect an adenoma in this mouse model provides a significant advantage over conventional technologies.

In summary, in this example, an investigation of two mice was carried out in which a higher signal in polyps compared to healthy intestinal signal was clearly observed. This difference was significant in three segments. Based on the signal intensity data collected, a high background signal decreases the contrast enhancement. When the background signal decreases in the ilium and colon, the polyps were readily detected against background tissue.

While there have been shown several and alternate embodiments of the present disclosure, it is to be understood that certain changes can be made as would be known to one skilled in the art without departing from the underlying scope of the disclosure as is discussed and set forth above. Furthermore, the embodiments described above are only intended to illustrate the principles of the disclosure and are not intended to limit the scope of the disclosure to the disclosed elements.

Unless indicated otherwise in this disclosure, when a range of any type is disclosed or claimed, for example a range of distance, wavelength, percent, or the like, it is intended to disclose or claim individually each possible number that such a range could reasonably encompass, including any sub-ranges encompassed therein. For example, when the Applicants disclose or claim a range in time duration from about 0.1 to about 1 second, Applicants' intent is to disclose or claim individually every possible number that such a range could encompass, consistent with the disclosure herein. Thus, by the disclosure that a time adjustment can range from about 0.1 to about 1 seconds, Applicants intent is to recite that the time adjustment can be about 0.1, about 0.2, about 0.3, about 0.4, about 0.5, about 0.6, about 0.7, about 0.8, about 0.9, or about 1 second, including any ranges, sub-ranges, or combinations thereof between any disclosed times. Accordingly, Applicants reserve the right to proviso out or exclude any individual members of any such group, including any sub-ranges or combinations of sub-ranges within the group, that can be claimed according to a range or in any similar manner, if for any reason Applicants choose to claim less than the full measure of the disclosure, for example, to account for a reference that Applicants are unaware of at the time of the filing of the application.

Unless otherwise stated, all publications and patents mentioned in the disclosure are incorporated herein by reference in pertinent part, for the purpose of describing and disclosing, for example, the constructs and methodologies that are described in the publications, which might be used in connection with the present disclosure. The publications discussed above and throughout the text are provided solely for their disclosure prior to the filing date of the present application. Nothing herein is to be construed as an admission that the inventors are not entitled to antedate such disclosure by virtue of prior invention. Should the usage or terminology used in any reference that is incorporated by reference conflict with the usage or terminology used in this disclosure, the usage and terminology of this disclosure controls. The Abstract of the disclosure is provided herewith to satisfy the requirements of 37 C.F.R. §1.72 and the purpose stated in 37 C.F.R. §1.72(b) "to enable the United States Patent and Trademark Office and the public generally to determine quickly from a cursory inspection the nature and gist of the technical disclosure." The Abstract is not intended to be used to construe the scope of the appended claims or to limit the scope of the subject matter disclosed herein. Any use of the past tense to describe an example otherwise indicated as constructive or prophetic is not intended to reflect that the constructive or prophetic example has actually been carried out.

CHART 1

Parts list for the fundamental integrated imaging device and method.

| Part No. | Part | Manufacturer | Description/Function |
|---|---|---|---|
| 100 | "White" LED lamp | Lights of America | Provides wide-field illumination for target area. White LEDs do not have any emission in the near infrared (NIR) range |
| 102 | Laser excitation source/spectrometer | Delta Nu | Houses 200 mW 785 nm laser diode for focused optical excitation. Also houses spectrophotometer for fluorescence and/or Raman emission from target area. |
| 104 | Handheld wand | Delta Nu | Used to guide the focus excitation to the specific location of interest within the target area. |
| 106 | Fiber optic cable | Delta Nu | Transmits excitation laser light to handheld probe(104) and collects emission light or scattered light for spectroscopy (102) |
| 108 | UV-NIR compact lens | Schneider Optics | Main lens; F1.9/35 mm, 216 mm working distance, ⅔" sensor format, focuses on and collects all light emission from target field. |
| 110 | Correction lens | Melles-Griot | (a) Achromatic lens that infinity corrects the image focused by the main lens; (b, c) achromatic lens that focuses the infinity corrected image into the NIR and laser camera's, respectively; (d)achromatic lens that focuses infinity corrected image into the color camera. Achromatic lenses 110a. 110b, and 110c are HEBBAR multilayer 700-1100 nm coated and 110d is $MgF_2$-400-700 nm coated. |

CHART 1-continued

Parts list for the fundamental integrated imaging device and method.

| Part No. | Part | Manufacturer | Description/Function |
|---|---|---|---|
| 112 | Silver mirror | Thor | The silver protected morrow reflects the infinity corrected image 90 into image system casing that contains filtering components and cameras; >96% reflectivity from 400-2000 nm. |
| 114 | Short pass dichroic filter | Melles-Griot | 800 nm short pass dietectric dichroic filter, reflects light greater than 800 nm towards NIR camera (122a), white light less than 800 nm passes through the dichroic to be further filtered for the laser and color video channels. |
| 116 | Short pass dichroic filter | Melles-Griot | 650 nm short pass dietectric dichroic reflects light less than 800 nm (because of first dietectric filter, part 114) and greater than 650 nm towards the laser channel (122b). Light less than 650 nm goes directly into the color channel camera (126) |
| 118 | Long pass filter | Chroma | Long pass filter that artenuates light below 810 nm and passes light great than 810 nm to the NIR camera (122a), this filter is mostly needed to block bleed through excitation light from the 785 nm laser. |
| 120 | Band pass filter | Omega | Band pass filter that further defines that wavelength of light that passes to the NIR camera (122a), allows a range of light that is matched with the optical probe of choice |
| 122 | NIRCCD video camera | AlliedVision Tec | Real time (40 frame/sec) C-mount NIR video camera with ½' Sony interfaced HAD CCD sensor to spatially detect (a) fluorescence or Raman emission and (b) localized laser excitation. Produces 492 × 768 pixel images with 8-bit resolution. |
| 124 | OD1 neutral density filter | Thor | Neutral density filter that allows 10% light transmittance; is located immediately before the laser channel NIR video camera (1226). Antireflection coated for 650-1050 nm. |
| 126 | Color CCD video camera | Allied VisionTec | Real time (40 frame/sec) C-mount color video camera with ½' Sony interlaced HAD CCD sensor to provide operator with spatial relativity for NIR and laser channels. Produces 492 × 768 pixel images with 8-bit resolution. |
| 128 | Casing | Thor | 10" × 12" optical bread board and casing for the wide-field optical imaging components |
| 130 | Computer | TBD | Computer for importing of data from spectrophotometer (102) and the three video cameras (122a, 122b, 126) Processes signals and images and integrates into a single software package specifically developed for this application. |

CHART 2

Parts list and Figures Labels for FIGS. 14-16

| Number | Description |
|---|---|
| 200 | Video processor |
| 201 | Widefield imaging system electronic connection |
| 210 | Widefield imaging system |
| 211 | Camera sensor |
| 213 | Optical filters and mirrors |
| 215 | Collimating lens(es) |
| 220 | Optomechanical coupler |
| 221 | Mechanical coupler, fiberscope eyepiece side |
| 222 | Mechanical coupler, widefield imaging side |
| 225 | Optical elements of coupler |
| 230 | Fiberscope handpiece |
| 231 | Fiberscope |
| 233 | Fiberscope eyepiece |
| 235 | Fiberscope lens, remote end |
| 300 | Video processor |
| 301 | Video endoscope electronic connection |
| 310 | Widefield imaging system |
| 312 | Multispectral camera sensor |
| 315 | Widefield imaging system lens |
| 330 | Video endoscope handpiece |
| 331 | Video endoscope |
| 335 | Video endoscope, remote end |
| 400 | Video processor |
| 401 | Video endoscope electronic connection |
| 410 | Widefield imaging system |
| 411 | Camera sensor |
| 413 | Optical filters and mirrors |
| 415 | Widefield imaging system lens |
| 430 | Video endoscope handpiece |
| 431 | Video endoscope |
| 435 | Video endoscope, remote end |

We claim:

1. A system for intra-operatively providing anatomical guidance in a diagnostic or therapeutic procedure, comprising:

(a) a lamp configured to emit a beam of visible light to an area of interest of a living subject;

(b) a laser configured to emit a beam of near-infrared light to the area of interest;

(c) an optical probe optically coupled to the laser but not optically coupled to the lamp, comprising an optical fiber configured to deliver the emitted beam of near-infrared light to illuminate the area of interest and configured to collect light that is scattered or emitted from a contrast agent introduced into target tissues in the area of interest, in response to illumination by the laser;

(d) a spectrometer optically coupled to the optical probe and configured to detect the collected light and to generate a corresponding signal that comprises collected light data, and wherein the optical probe is further configured to transmit the collected light to the spectrometer through the optical fiber;

(e) a first CCD or CMOS camera configured to detect visible light that is emitted from the area of interest in response to illumination by the lamp and to generate a corresponding signal comprising visible light data;

(f) a second CCD or CMOS camera configured to detect near-infrared light having a first predetermined wavelength that is emitted from the area of interest in response to illumination by the laser and to generate a corresponding signal comprising a first set of near-infrared light data;

(g) a third CCD or CMOS camera configured to detect near-infrared light having a second predetermined wavelength that is different from the first predetermined wavelength and that is emitted from the area of interest in response to illumination by the laser, and to generate a corresponding signal comprising a second set of near-infrared light data;
(h) a display for displaying at least one visual representation of data; and
(i) a central processing unit, a processor, or a microprocessor in communication with each of the lamp, laser, spectrometer, first CCD or CMOS camera, second CCD or CMOS camera, third CCD or CMOS camera, and display, and programmed to generate at least one real-time integrated visual representation of the area of interest from each of the collected light data, visible light data, first set of near-infrared light data, and second set of near-infrared light data and to display the at least one real-time visual representation on the display, for guidance during the diagnostic or therapeutic procedure.

2. A system according to claim 1, further comprising a speaker, wherein the programmer is further programmed to generate at least one real-time aural representation of the area of interest from each of the collected light data, first set of near-infrared light data, and second set of near-infrared light data and to emit a sound for the at least one real-time aural representation through the speaker, for guidance during the diagnostic or therapeutic procedure.

3. A system according to claim 1, wherein the optical probe is integral to an endoscopic device or a therapeutic laser system.

4. A system according to claim 1, wherein the optical probe is integral to an endoscopic device selected from an endoscope, a colonoscope, a microscope, a surgical microscope, an arthroscope, a laparoscope, a thoracoscope, a mediastinan endoscope, a hysteroscope, a cyctoscope, a ureteroscope, a stereomicroscope, a colposcope, a fiber-optical system, or a rigid optical systems.

5. A system according to claim 1, wherein the optical probe is integral to a borescope or a video endoscope endoscopic device.

6. A system according to claim 1, wherein the contrast agent comprises at least one of a Raman probe and a fluorescence probe and the collected light data comprises at least one of Raman data and fluorescence data, respectively.

7. A system according to claim 6, wherein the at least one integrated visual representation comprises a wide-field image of the area of interest generated from the visible light data, a laser excitation image of a selected area of the area of interest defined within the wide-field image and generated from at least one of the generated first set of near-infrared light data and the generated second set of near-infrared light data, and at least one of a Raman image generated from the Raman data and a fluorescence image generated from the fluorescence data, wherein the at least one of the Raman image and fluorescence image is defined within the wide-field image and the laser excitation image.

8. A system according to claim 7, wherein the at least one of the Raman image and the fluorescence image is an overlay image on the laser excitation image.

9. An imaging system using integrated bright-field imaging, near-infrared imaging, and at least one of Raman imaging and fluorescence imaging for intra-operatively evaluating target tissues in an area of interest of a living subject, comprising:
(a) a lamp for delivering a beam of visible light to the area of interest and a laser for delivering a beam of near-infrared light to the area of interest;
(b) a Raman and fluorescence imaging device, comprising:
(i) an optical probe optically coupled to the laser but not optically coupled to the lamp for delivering the near infrared light to illuminate target tissues of the area of interest and for collecting at least one of scattered light and emitted light from a corresponding at least one of a Raman probe and a fluorescence probe that is introduced into the target tissues and illuminated by the laser; and
(ii) a spectrometer in communication with the optical probe for obtaining at least one of Raman data from the collected scattered light and fluorescence data from the collected emitted light, respectively; and
(c) a bright-field imaging system, comprising:
(i) a first CCD or CMOS camera for obtaining visible light data from visible light emitted from the area of interest in response to illumination by the lamp;
(ii) a second CCD or CMOS camera for obtaining a first set of near-infrared data from light having a first predetermined wavelength that is emitted from the area of interest in response to illumination by the laser;
(iii) a third CCD or CMOS camera for obtaining a second set of near infrared data from light having a second predetermined wavelength that is different from the first predetermined wavelength and that is emitted from the area of interest in response to illumination by the laser;
(iv) an optical port;
(v) a system lens comprising a UV-NIR compact lens and a first focusing lens group;
(vi) a trichroic prism or a pair of dichroic mirrors;
(vii) a first laser attenuating filter;
(viii) a bandpass filter;
(ix) a second laser attenuating filter;
(x) a second focusing lens group, a third focusing lens group, and a fourth focusing lens group;
wherein the optical port and the first CCD or CMOS camera define a first optical path therebetween having the trichroic prism or the pair of dichroic mirrors and the second focusing lens group, wherein the optical port and the second CCD or CMOS camera define a second optical path therebetween having the trichroic prism or dichroic mirror, the second laser attenuating filter, bandpass filter, and fourth focusing lens group, and wherein the optical port and the third CCD or CMOS camera define a third optical path therebetween having the trichroic prism or the pair of dichroic mirrors, first laser attenuating filter, and third focusing lens group.

10. An imaging system according to claim 9, wherein the optical probe is integral to an endoscopic device or a therapeutic laser system.

11. An imaging system according to claim 9, wherein the optical probe is integral to an endoscopic device selected from an endoscope, a colonoscope, a microscope, a surgical microscope, an arthroscope, a laparoscope, a thoracoscope, a mediastinan endoscope, a hysteroscope, a cyctoscope, a ureteroscope, a stereomicroscope, a colposcope, a fiber-optical system, or a rigid optical systems.

12. An imaging system according to claim 9, wherein the optical probe is integral to a borescope or a video endoscopeendoscopic device.

13. An imaging system according to claim 9, further comprising:
(d) a display for displaying at least one visual representation of data;
(e) a speaker for emitting at least one aural representation of data; and
(f) a central processing unit, a processor, or a microprocessor in communication with each of the lamp, laser, spectrometer, first CCD or CMOS camera, second CCD or CMOS camera, third CCD or CMOS camera, display, and speaker, and programmed for generating in real-time at least one integrated visual representation and the at least one aural representation of the area of interest from the visible light data, first set of near-infrared data, second set of near-infrared data, and at least one of the Raman data and fluorescence data and displaying the integrated visual representation on the display and emitting the at least one aural representation through the speaker, to provide guidance for performing a diagnostic or therapeutic procedure.

14. An imaging system according to claim 9, wherein the at least one real-time integrated visual representation of the area of interest comprises a wide-field image of the area of interest generated from the visible light data, a laser excitation image of a predetermined area defined within the wide-field image that is generated from at least one of the first set of near-infrared data and the second set of near-infrared data, and at least one of a Raman image and a fluorescence image that is generated from a corresponding at least one of the Raman data and fluorescence data.

15. An imaging system according to claim 9, wherein:
(a) the laser excitation image is an overlay image on the wide-field image and represents the location of the delivered beam of near-infrared light within the area of interest;
(b) the at least one of the Raman data and fluorescence data is represented by a signal that, when exceeding a predefined threshold level, signifies disease in the target tissues;
(c) the at least one of the Raman image and the fluorescence image is a color overlay image on the laser excitation image, having an opacity representative of the level of the signal exceeding the predefined threshold level; and
(d) the opacity of the color overlay image decays over time to be progressively more translucent relative to the laser excitation image.

16. An imaging system according to claim 9, wherein
(a) at least one of the Raman data and fluorescence data is represented by a signal that, when exceeding a predefined threshold level, signifies disease in the target tissues; and
(b) at least one of the Raman data and fluorescence data is an aural signal, having a representation that is proportional to the level of the signal exceeding the predefined threshold level.

17. A method for intra-operatively providing anatomical guidance in a diagnostic or therapeutic procedure, comprising the steps of:
(a) introducing at least one contrast agent into target tissues in an area of interest of a living subject;
(b) emitting a beam of visible light to the area of interest, using a lamp;
(c) emitting a beam of near-infrared light to the area of interest, using a laser;
(d) delivering the emitted beam of near-infrared light to illuminate the area of interest, using an optical fiber of an optical probe that is optically coupled to the laser but not optically coupled to the lamp;
(e) collecting at least one of scattered light and emitted light from the contrast agent in response to illumination by the laser, using the optical fiber of the optical probe, wherein the contrast agent comprises at least one of a Raman probe and a fluorescence probe;
(f) detecting the collected light and generating a corresponding signal that comprises collected light data, using a spectrometer that is optically coupled to the optical fiber, and wherein the optical fiber is further configured to deliver the collected light to the spectrometer;
(g) detecting visible light that is emitted from the area of interest in response to illumination by the lamp and generating a corresponding signal comprising visible light data, using a first CCD or CMOS camera;
(h) detecting near-infrared light having a first predetermined wavelength that is emitted from the area of interest in response to illumination by the laser and generating a corresponding signal comprising a first set of near-infrared light data, using a second CCD or CMOS camera;
(i) detecting near-infrared light having a second predetermined wavelength that is different from the first predetermined wavelength and that is emitted from the area of interest in response to illumination by the laser and generating a corresponding signal comprising a second set of near-infrared light data, using a third CCD or CMOS camera;
(j) generating at least one real-time integrated visual representation of the area of interest from the collected light data, visible light data, first set of near-infrared data, and second set of near-infrared data, using a central processing unit, a processor, or a microprocessor in communication with each of the spectrometer, first CCD or CMOS camera, second CCD or CMOS camera, and third CCD or CMOS camera; and
(k) displaying the at least one real-time integrated visual representation generated by the central processing unit, processor, or microprocessor, for guidance during a diagnostic or therapeutic procedure, using a display in communication with the central processing unit, processor, or microprocessor.

18. A method according to claim 17, further comprising the steps of
(l) generating at least one real-time aural representation of the area of interest from the collected light data, first set of near-infrared data, and second set of near-infrared data, using a central processing unit, a processor, or a microprocessor in communication with each of the spectrometer, first CCD or CMOS camera, second CCD or CMOS camera, and third CCD or CMOS camera; and
(m) emitting the at least one real-time aural representation generated by the central processing unit, processor, or microprocessor, for guidance during a diagnostic or therapeutic procedure, using a speaker in communication with the central processing unit, processor, or microprocessor.

19. A method according to claim 17, wherein the optical probe is integral to an endoscopic device or a therapeutic laser system.

20. A method according to claim 17, wherein the optical probe is integral to an endoscopic device selected from an endoscope, a colonoscope, a microscope, a surgical microscope, an arthroscope, a laparoscope, a thoracoscope, a mediastinan endoscope, a hysteroscope, a cyctoscope, a ureteroscope, a stereomicroscope, a colposcope, a fiber-optical system, or a rigid optical systems.

21. A method according to claim 17, wherein the optical probe is integral to a borescope or a video endoscope endoscopic device.

22. A non-transitory computer-readable storage medium having stored thereon computer-executable instructions which, when executed by a central processing unit, a processor, or a microprocessor, cause a computer to perform functions for intra-operatively providing anatomical guidance in a surgical procedure, the functions comprising:

(a) causing a lamp in communication with the central processing unit, processor, or microprocessor to emit a beam of visible light to an area of interest of a living subject;

(b) causing a laser optically coupled to an optical fiber of an optical probe and in communication with the central processing unit, processor, or microprocessor to emit a beam of near-infrared light to the area of interest through the optical fiber;

(c) causing the optical fiber of the optical probe to collect at least one of light scattered from a Raman probe introduced into the target tissues in response to illumination by the laser and light emitted from fluorescence probe introduced into the target tissues in response to illumination by the laser, the optical probe is integral to an endoscopic device or a therapeutic laser system;

(d) causing a spectrometer in communication with the central processing unit, processor, or microprocessor and the optical fiber to detect at least one of light that is scattered from the Raman probe and light that is emitted from the fluorescence probe, and collected through the optical fiber, in response to illumination from the laser;

(e) causing the spectrometer to generate at least one of a signal from the detected scattered light that comprises Raman data and a signal from the detected emitted light that comprises fluorescence data, respectively;

(f) causing a first CCD or CMOS camera that is in communication with the central processing unit, processor, or microprocessor to detect visible light that is emitted from the area of interest in response to illumination by the lamp, and causing the first CCD or CMOS camera to generate a corresponding signal comprising visible light data;

(g) causing a second CCD or CMOS camera that is in communication with the central processing unit, processor, or microprocessor to detect near-infrared light having a first predetermined wavelength that is emitted from the area of interest in response to illumination by the laser and causing the second CCD or CMOS camera to generate a corresponding signal comprising a first set of near-infrared light data;

(h) causing a third CCD or CMOS camera that is in communication with the central processing unit, processor, or microprocessor to detect near-infrared light having a second predetermined wavelength that is different from the first predetermined wavelength and that is emitted from the area of interest in response to illumination by the laser, and causing the third CCD or CMOS camera to generate a corresponding signal comprising a second set of near-infrared light data;

(i) generating at least one real-time integrated visual representation of the area of interest from the visible light data, first set of near-infrared data, second set of near-infrared data, and at least one of the Raman data and fluorescence data; and (j) causing a display in communication with the central processing unit, processor, or microprocessor to display the generated at least one real-time integrated visual representation for guidance during a diagnostic or therapeutic procedure.

23. A non-transitory computer-readable storage medium according to claim 22, wherein the functions further comprise:

(k) generating at least one real-time aural representation of the area of interest from at least one of the Raman data and fluorescence data; and (l) causing a speaker in communication with the central processing unit, processor, or microprocessor to emit a the generated at least one real-time aural representation for guidance during a diagnostic or therapeutic procedure.

24. A method for intra-operatively identifying disease in target tissues in an area of interest of a living subject, to be resected in a diagnostic or therapeutic procedure, comprising the steps of:

(a) introducing at least one of a Raman probe and a fluorescence probe into the area of interest until the at least one probe has accumulated in the target tissues;

(b) preparing the living subject and the area of interest for a diagnostic or therapeutic procedure;

(c) initializing an imaging system for integrated brightfield imaging, near-infrared imaging, and at least one of Raman imaging and fluorescence imaging;

(d) beginning the diagnostic or therapeutic procedure in the area of interest;

(e) using a first real-time integrated visual representation of the area of interest and the target tissues, generated by the imaging system, to identify a boundary of the target tissues that are diseased;

(f) performing a surgical resection of the identified diseased target tissues within the boundary;

(g) after the surgical resection, using a second displayed at least one real-time integrated visual representation of the area of interest and the target tissues, generated by the imaging system, to identify any remaining diseased target tissues within the boundary; and (h) if any remaining diseased target tissues are identified, performing a series of further surgical resections on identified remaining diseased target tissues corresponding to a respective series of real-time integrated visual representations generated by the imaging system, until the area of interest is free from diseased target tissues;

wherein the imaging system is a system according to claim 1; and the optical probe is integral to an endoscopic device, or a therapeutic laser system.

25. A method according to claim 24, wherein the step of identifying the boundary of the target tissues that are diseased and the step of identifying any remaining diseased target tissues within the boundary comprise identifying visual representations of the first set of near-infrared light data, second set of near-infrared light data, and collected light data that are displayed in a selected area of the integrated visual representation.

26. A method according to claim 24, wherein:

(a) the visual representation of the first set of near-infrared data and second set of near-infrared data is a laser excitation image that represents the location of the delivered beam of near-infrared light within the area of interest, and that is displayed as a color overlay image on the wide-field image;

(b) the signal representing the collected light data that is generated by the g spectrometer, when exceeding a predetermined threshold level, signifies disease in the target tissues;

(c) the visual representation of the collected light data is a color overlay image on the laser excitation image, having an opacity representative of the level of the signal exceeding the predefined threshold level; and (d) the opacity of the color overlay image that represents the collected light data decays over time to be progressively more translucent relative to the laser excitation image.

* * * * *